(12) United States Patent
Boerjan et al.

(10) Patent No.: US 10,006,041 B2
(45) Date of Patent: Jun. 26, 2018

(54) MEANS AND METHODS FOR ALTERING THE LIGNIN PATHWAY IN PLANTS

(71) Applicants: VIB VZW, Ghent (BE); Universiteit Gent, Ghent (BE)

(72) Inventors: Wout Boerjan, Kalken (BE); Ruben Vanholme, Destelbergen (BE); Lisa Sundin, Ghent (BE)

(73) Assignees: VIB VZW, Ghent (BE); UNIVERSITEIT GENT, Ghent (BE)

( * ) Notice: Subject to any disclaimer, the term of this patent is extended or adjusted under 35 U.S.C. 154(b) by 180 days.

(21) Appl. No.: 14/421,796

(22) PCT Filed: Aug. 14, 2013

(86) PCT No.: PCT/EP2013/066984
§ 371 (c)(1),
(2) Date: Feb. 13, 2015

(87) PCT Pub. No.: WO2014/027021
PCT Pub. Date: Feb. 20, 2014

(65) Prior Publication Data
US 2015/0232872 A1 Aug. 20, 2015

Related U.S. Application Data

(60) Provisional application No. 61/684,019, filed on Aug. 16, 2012.

(51) Int. Cl.
*C12N 15/82* (2006.01)
(52) U.S. Cl.
CPC ............... *C12N 15/8255* (2013.01)
(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,034,323 A | 7/1991 | Jorgensen et al. | |
| 5,283,184 A | 2/1994 | Jorgensen et al. | |
| 5,565,350 A | 10/1996 | Kmiec | |
| 5,731,181 A | 3/1998 | Kmiec et al. | |
| 5,756,325 A | 5/1998 | Kmiec | |
| 5,759,829 A | 6/1998 | Shewmaker et al. | |
| 5,760,012 A | 6/1998 | Kmiec et al. | |
| 5,795,972 A | 8/1998 | Kmiec | |
| 5,871,984 A | 2/1999 | Kmiec | |
| 5,942,657 A | 8/1999 | Bird et al. | |
| 5,962,764 A | 10/1999 | Briggs et al. | |
| 6,453,242 B1 | 9/2002 | Eisenberg et al. | |
| 6,635,805 B1 | 10/2003 | Baulcombe et al. | |
| 7,985,890 B2 * | 7/2011 | Basu | C12N 9/1007 435/320.1 |
| 8,637,290 B2 | 1/2014 | O'Donoghue | |
| 2003/0037355 A1 | 2/2003 | Barbas, III et al. | |
| 2003/0188343 A1 * | 10/2003 | Bowen | C07K 14/415 800/287 |
| 2004/0181830 A1 | 9/2004 | Kovalic et al. | |
| 2007/0061916 A1 | 3/2007 | Kovalic et al. | |
| 2010/0017916 A1 | 1/2010 | Pappan et al. | |
| 2011/0154530 A1 | 6/2011 | Bläsing et al. | |
| 2012/0005770 A1 | 1/2012 | Hertzberg et al. | |

FOREIGN PATENT DOCUMENTS

| | | |
|---|---|---|
| EP | 1033405 A2 | 9/2000 |
| EP | 1198985 A1 | 4/2002 |
| WO | 9949029 A1 | 9/1999 |
| WO | 9953050 A1 | 10/1999 |
| WO | 9961631 A1 | 12/1999 |
| WO | 0049035 A1 | 8/2000 |
| WO | 0200904 A2 | 1/2002 |
| WO | 2009146464 A2 | 12/2009 |
| WO | 2010020654 A2 | 2/2010 |
| WO | 2010062240 A1 | 6/2010 |
| WO | 2010141928 A2 | 12/2010 |
| WO | 2011112570 A1 | 9/2011 |
| WO | 2013167902 A1 | 11/2013 |
| WO | 2014027021 A1 | 2/2014 |

OTHER PUBLICATIONS

Coleman et al 2008 PNAS 105:4501-4506.*
Moehs et al 1996 Plant Molecular Biology 32:447-452.*
McClellan et al., Genetic screening for genes in *Arabidopsis thaliana* that improve sugar release from plant ignocellulose, Internet Citation, Jan. 1, 2010, p. 1, retrieved from the Internet: URL:http://gcep.stanford.edu/pdfs/v15Z1pJh8XCevgvx1PJO-g/Christopher_McClellan_Poster2010.pdf.
Vanholme et al., Potential of *Arabidopsis* systems biology to advance the biofuel field, Trends in Biotechnology, Nov. 1, 2010, pp. 543-547, vol. 28, No. 11.
Usadel et al., Co-expression tools for plant biology: opportunities for hypothesis generation and caveats, Plant, Cell & Environment, Dec. 1, 2009, pp. 1633-1651, vol. 32, No. 12.
Jung et al., Modifying crops to increase cell wall digestibility, Plant Science, Apr. 1, 2012, pp. 65-77, vol. 185-86.
Kavousi et al., Consequences of antisense down-regulation of a lignification-specific peroxidase on leaf and vascular tissue in tobacco lines demonstrating enhanced enzymic saccharification, Phytochemistry, Apr. 1, 2010, pp. 531-542, vol. 71, No. 5-6.

(Continued)

*Primary Examiner* — Brent T Page
(74) *Attorney, Agent, or Firm* — TraskBritt, P.C.

(57) ABSTRACT

The disclosure generally relates to the field of molecular biology, specifically the field of agricultural biology. In particular, the disclosure relates to means and methods for modifying the lignin flu and composition in plants. In particular, the disclosure provides chimeric genes comprising transaldolase sequences, which can be used in the context of this disclosure.

13 Claims, 23 Drawing Sheets
(13 of 23 Drawing Sheet(s) Filed in Color)

(56) References Cited

OTHER PUBLICATIONS

Abramson et al., Plant cell wall reconstruction toward improved lignocellulosic production and processability, Plant Science, Feb. 1, 2010, pp. 61-72, vol. 178, No. 2, Elsevier Ireland Ltd, IE.

Buanafina et al., Targeting expression of a fungal ferulic acid esterase to the apoplast, endoplasmic reticulum or golgi can disrupt feruloylation of the growing cell wall and increase the biodegradability of tall fescue (*Festucs arundinacea*), Plant Biotechnology Journal, Apr. 1, 2010, vol. 8, No. 3.

PCT International Search Report, PCT/EP2013/066984, dated Oct. 22, 2013.

Maxime et al., New insights into plant transaldolase, The Plant Journal, Jul. 2, 2005, pp. 1-16, vol. 43, No. 1.

Moehs et al., Cloning and expression of transaldolase from potato, Plant Molecular Biology, 1996, pp. 447-452, vol. 32, No. 3.

Shadle et al., Hydroxylation Pathways and Essential Roles for Phenolic Precursors in Cell Expansion and Plant Growth, Plant Physiology, Jan. 2006, vol. 140, pp. 30-48, American Society of Plant Biologists.

Coleman et al., Perturbed Lignification Impacts Tree Growth in Hybrid Popla☐ A Function of Sink Strength, Vascular Integrity, and Photosynthetic Assimilation, Plant Physiology, Nov. 2008, vol. 148, pp. 1229-1237, American Society of Plant Biologists.

Voelker et al., Antisense Down-Regulation of 4CL Expression Alters Lignification, Tree Growth, and Saccharification Potential of Field-Grown Poplar Plant Physiology®, Oct. 2010, vol. 154, pp. 874-886, American Society of Plant Biologists.

Abdulrazzak et al., Reveals the Existence of Nonredundant meta-Hydroxylation Pathways and Essential Roles for Phenolic Precursors in Cell Expansion and Plant Growth, Plant Physiology, Jan. 2006, vol. 140, pp. 30-48, American Society of Plant Biologists.

* cited by examiner

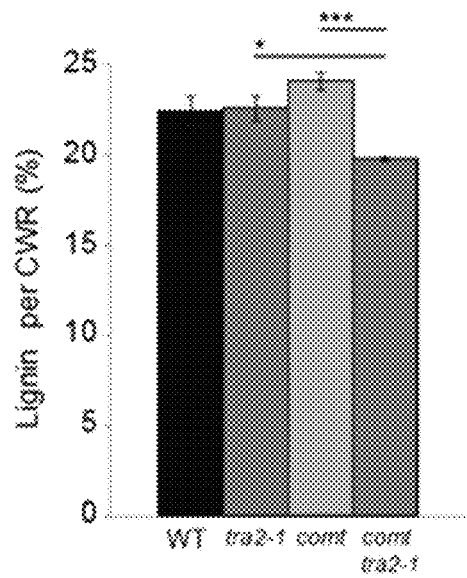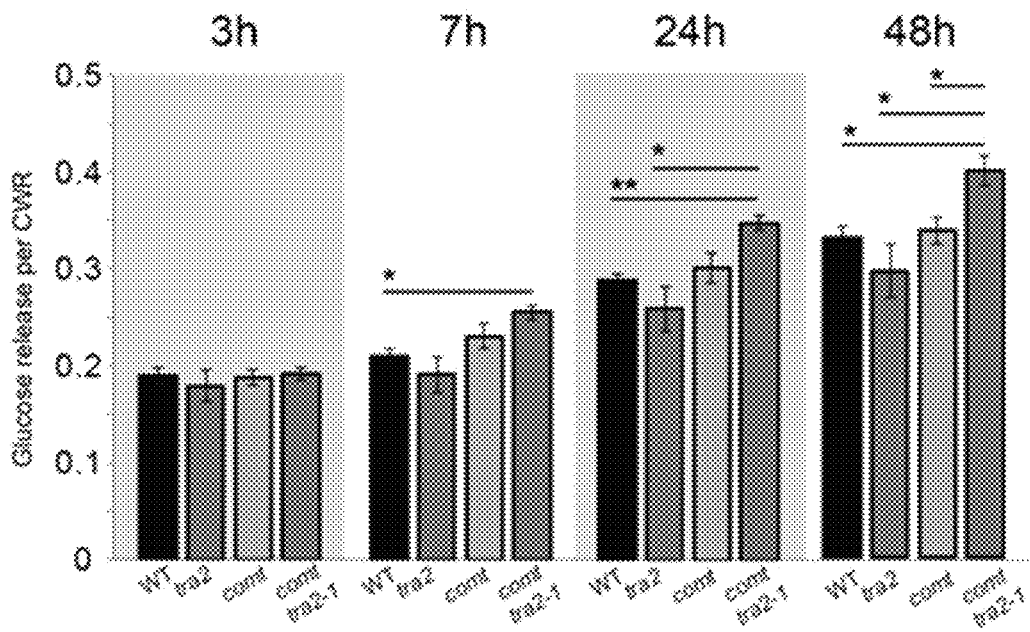
FIG. 11

| gene | AGI-code | mutant allele | growth characteristics | |
|---|---|---|---|---|
| | | | growth rate | final height |
| PAL1 | At2g37040 | pal1-2 (SALK_000357) | - | - |
| | | pal1-3 (SALK_022804) | - | - |
| PAL2 | At3g53260 | pal2-2 (SALK_092252) | - | - |
| | | pal2-3 (GABI_692H09) | - | - |
| C4H | At2g30490 | c4h-2 (ref3-2) | reduced** | ± 75% of WT |
| | | c4h-3 (ref3-3) | - | - |
| 4CL1 | At1g51680 | 4cl1-1 (SALK_142526) | - | - |
| | | 4cl1-2 (SM_3_27345) | - | - |
| 4CL2 | At3g21240 | 4cl2-1 (SLAT 02_14_04) | - | - |
| | | 4cl2-3 (GABI_353A11) | - | - |
| CCoAOMT1 | At4g34050 | ccoaomt1-3 (SALK_151507) | reduced* | - |
| | | ccoaomt1-5 (GABI_007F02) | - | - |
| CCR1 | At1g15950 | ccr1-3 (SALK_123689) | reduced** | ± 20% of WT |
| | | ccr1-6 (GABI_622C01) | reduced** | ± 65% of WT |
| F5H1 | At4g36220 | f5h1-2 (fah1-2) | - | - |
| | | f5h1-4 (SALK_063792) | - | - |
| COMT | At5g54160 | comt-1 (SALK_002373) | - | - |
| | | comt-4 (SALK_050030) | - | - |
| CAD6 | At4g34230 | cad6-1 (SALK_040062) | enhanced* | - |
| | | cad6-4 (SAIL_776_B06) | - | - |

FIG. 12

| gene name | AGI | pal1 | pal2 | c4h | 4cl1 | 4cl2 | ccoa-omt1 | ccr1 | f5h1 | comt | cad6 | WT 8cm | 16cm | 24cm | 32cm |
|---|---|---|---|---|---|---|---|---|---|---|---|---|---|---|---|
| genes involved in the general phenylpropanoid pathway ||||||||||||||||
| PAL1 | At2g37040 | -4.9 | 0.1 | 0.2 | | 0.1 | | | 0.1 | | 0.0 | | -0.1 | 0.0 | |
| PAL2 | At3g53260 | 0.0 | -3.4 | | | -0.1 | | 0.7 | | | | | 0.2 | 0.0 | |
| PAL3 | At5g04230 | 0.1 | 0.1 | 0.6 | 0.3 | 0.1 | | | 0.2 | 0.0 | -0.1 | | | 0.0 | |
| PAL4 | At3g10340 | 0.1 | -0.1 | | | -0.1 | | 0.3 | | | | | | 0.0 | |
| C4H | At2g30490 | 0.1 | -0.1 | 0.8 | 0.7 | -0.2 | | | | | -0.2 | | -0.1 | 0.0 | |
| 4CL1 | At1g51680 | | | 0.0 | -6.0 | | | | | | | | -0.1 | 0.0 | |
| 4CL2 | At3g21240 | | 0.1 | | | -1.8 | | | 0.0 | -0.1 | 0.0 | | | 0.0 | |
| HCT | At5g48930 | | -0.1 | -0.1 | 0.1 | | | | | | -0.1 | | -0.1 | 0.0 | |
| C3H1 | At2g40890 | -0.1 | -0.1 | | | 0.1 | | | | | -0.2 | | | 0.0 | |
| CCoAOMT1 | At4g34050 | 0.0 | 0.0 | | | -0.1 | -5.6 | | | | -0.2 | | | 0.0 | |
| genes involved in the monolignol specific pathway ||||||||||||||||
| CCR1 | At1g15950 | -0.1 | 0.0 | 0.1 | | -0.2 | 0.0 | -2.9 | -0.2 | | -0.1 | | | 0.0 | |
| CCR2 | At1g80820 | | 0.1 | | | -0.2 | | | 0.1 | 0.1 | -0.1 | | | 0.0 | |
| F5H1 | At4g36220 | -0.1 | 0.0 | | | | -0.1 | | -3.4 | | 0.0 | | 0.2 | 0.0 | |
| COMT | At5g54160 | -0.1 | 0.0 | 0.1 | | 0.0 | 0.1 | 0.1 | | -1.4 | 0.0 | | | 0.0 | |
| CAD2 | At3g19450 | | -0.1 | | 0.6 | -0.1 | | -0.1 | | | | | -0.1 | 0.0 | |
| CAD6 | At4g34230 | 0.1 | 0.0 | 0.2 | 0.2 | | 0.0 | | 0.0 | 0.1 | -7.3 | | | 0.0 | -0.1 |

FIG. 13

| gene name | AGI | pal1 | pal2 | c4h | 4cl1 | 4cl2 | ccoa-omt1 | ccr1 | f5h1 | comt | cad6 | WT 8cm | 16cm | 24cm | 32cm |
|---|---|---|---|---|---|---|---|---|---|---|---|---|---|---|---|
| laccases | | | | | | | | | | | | | | | |
| LAC4 | At2g38080 | | -0.2 | -0.1 | 0.1 | 0.1 | -0.1 | 0.2 | 0.6 | | -0.2 | 1.1 | 0.0 | 0.0 | 1.2 |
| LAC16 | At5g58910 | | -0.1 | -0.1 | 0.0 | -0.1 | -0.1 | 0.2 | | | -0.1 | 0.7 | 0.1 | 0.0 | 0.7 |
| LAC11 | At5g03260 | 0.0 | 0.0 | 0.2 | | | 0.6 | 0.6 | 0.2 | 0.0 | 0.0 | | 0.2 | 0.0 | 1.0 |
| LAC17 | At5g60020 | 0.7 | -0.2 | | 0.2 | 0.1 | | 0.6 | 0.7 | | -0.2 | 0.0 | | 0.0 | 1.7 |
| LAC2 | At2g29130 | 0.2 | -0.1 | 0.1 | 0.7 | 0.3 | 0.2 | 0.7 | | | 0.3 | 0.1 | | 0.0 | 1.4 |
| LAC5 | At2g40370 | 0.2 | -0.1 | | 0.3 | 0.1 | 0.1 | 0.1 | | 0.0 | -0.1 | 0.9 | 1.2 | 0.0 | 1.2 |
| LAC12 | At5g05390 | -0.2 | -0.2 | 0.2 | | 0.2 | -0.1 | | | | -0.1 | 0.9 | 1.1 | 0.0 | 1.6 |
| LAC10 | At5g01190 | | -0.1 | 0.5 | | 0.3 | 0.0 | | | -0.2 | 0.0 | 2.6 | 1.5 | 0.0 | 1.6 |
| class III peroxidases | | | | | | | | | | | | | | | |
| PER50 | At4g37520 | -0.1 | 0.0 | | 0.2 | 0.0 | | 0.2 | | -0.2 | 0.2 | 1.9 | -0.2 | 0.0 | 0.8 |
| PER52 | At5g05340 | | | | -1.2 | 0.3 | | -0.9 | 0.1 | | -0.2 | -1.9 | | 0.0 | |
| PER51 | At4g37530 | -0.1 | 0.0 | 0.0 | -0.1 | 0.2 | 0.2 | | -0.1 | 0.3 | 0.0 | 1.7 | | 0.0 | 0.9 |
| PER42 | At4g21960 | 0.1 | 0.0 | | 0.3 | 0.0 | | 0.0 | 0.1 | -0.1 | -0.1 | 1.5 | 0.6 | 0.0 | 0.7 |
| PER25 | At2g41480 | 0.3 | 0.1 | -0.2 | | -0.1 | -0.2 | 0.4 | 0.2 | 0.2 | | 1.4 | 0.8 | 0.0 | |
| PER49 | At4g36430 | -0.2 | 0.0 | 0.0 | | 0.1 | 0.0 | 0.2 | 1.1 | 1.2 | 0.2 | 1.3 | 1.3 | 0.0 | |
| PER12 | At1g71695 | | -0.1 | 0.0 | | 0.1 | 0.6 | | -0.2 | | 0.0 | 1.0 | 0.0 | 0.0 | 1.0 |
| PER37 | At4g08770 | 0.3 | 0.1 | | | 0.1 | 0.1 | 0.9 | | | 0.1 | 0.9 | 0.9 | 0.0 | 0.5 |
| PER58 | At5g19880 | -0.1 | -0.1 | | | 0.0 | 0.1 | | 0.3 | -0.1 | -0.2 | 0.7 | 0.8 | 0.0 | |
| PER29 | At3g17070 | 0.0 | -0.1 | -0.1 | 0.3 | 0.1 | 0.0 | | 0.0 | -0.1 | 0.2 | 0.2 | 0.0 | 0.0 | 1.2 |
| PER35 | At3g49960 | -0.1 | 0.0 | 0.0 | 0.0 | 0.1 | 0.0 | 0.0 | 0.0 | 0.0 | 0.0 | 0.8 | 0.2 | 0.0 | -0.1 |
| PER63 | At5g40150 | -0.2 | -0.1 | -0.1 | 0.0 | 0.1 | -0.2 | 0.2 | -0.1 | -0.2 | -0.2 | 1.7 | | 0.0 | -0.1 |
| PER66 | At5g51890 | 0.3 | 0.2 | | 0.7 | | 1.5 | 1.6 | 0.1 | 0.7 | 0.3 | 1.7 | 0.1 | 0.0 | |
| PER53 | At5g06720 | -0.2 | 0.0 | 0.0 | -0.2 | 0.1 | 0.0 | 1.4 | | | 0.0 | 1.6 | 0.1 | 0.0 | 0.7 |
| PER64 | At5g42180 | | -0.2 | 0.3 | | 0.4 | 0.2 | 0.0 | 0.7 | | -0.3 | 2.2 | 1.4 | 0.0 | 1.6 |
| PER3 | At1g05260 | -0.1 | 0.1 | | 0.5 | 0.6 | | | | 0.1 | 0.1 | 2.5 | 1.7 | 0.0 | 1.0 |

FIG. 14

| gene name | AGI | pal1 | pal2 | c4h | 4cl1 | 4cl2 | ccoa-omt1 | ccr1 | f5h1 | comt | cad6 | WT 8cm | 16cm | 24cm | 32cm |
|---|---|---|---|---|---|---|---|---|---|---|---|---|---|---|---|
| glycosyltransferases | | | | | | | | | | | | | | | |
| UGT72E2 | At5g66690 | | -0.1 | -1.4 | -0.9 | 0.0 | -0.7 | -1.5 | 0.7 | -0.3 | -0.3 | -0.8 | -1.0 | 0.0 | -1.0 |
| UGT72E3 | At5g26310 | -0.2 | -0.1 | | -0.2 | 0.0 | -0.2 | | 0.3 | 0.1 | 0.1 | 0.0 | -0.1 | 0.0 | -0.1 |
| β-glucosidases | | | | | | | | | | | | | | | |
| BGLU45 | At1g61810 | 0.0 | -0.1 | 0.6 | | 0.0 | | 0.1 | -0.1 | | 0.0 | | 0.1 | 0.0 | -0.2 |
| BGLU46 | At1g61820 | | 0.0 | 0.7 | 0.9 | 0.2 | 0.6 | 0.1 | 0.1 | 0.0 | 0.0 | -1.0 | | 0.0 | 1.0 |
| BGLU47 | At4g21760 | 0.0 | 0.0 | 0.2 | | 0.0 | 0.1 | 0.1 | 0.2 | | -0.1 | -0.1 | | 0.0 | 2.0 |

FIG. 15

| gene name | AGI | pal1 | pal2 | c4h | 4cl1 | 4cl2 | ccoa-omt1 | ccr1 | f5h1 | comt | cad6 | WT 8cm | 16cm | 24cm | 32cm |
|---|---|---|---|---|---|---|---|---|---|---|---|---|---|---|---|
| HCALDH/REF1 | At3g24503 | 0.1 | 0.0 | -0.1 | | -0.1 | | 0.6 | 0.2 | 0.1 | 0.1 | 1.7 | 1.5 | 0.9 | |
| SGT, UGT84A2/BRT1 | At3g21560 | -0.2 | 0.0 | 0.0 | | -0.2 | | | | 0.0 | 0.1 | | | 0.9 | |
| SGT, UGT84A3 | At4g15490 | 0.2 | 0.1 | 0.0 | | 0.0 | 0.0 | | | 0.0 | | -0.1 | | 0.0 | 0.2 |
| SST | At2g22980 | -0.1 | 0.0 | | 0.6 | | 0.7 | 0.0 | | 0.2 | 0.0 | 1.1 | 1.5 | 0.0 | 0.5 |
| SST | At2g23010 | | 0.0 | -0.2 | | 0.2 | 0.0 | | | | 0.0 | 0.1 | 0.2 | 0.0 | |
| SMT/SNG1 | At2g22990 | 0.1 | 0.2 | -1.0 | | -0.9 | -1.1 | | | -0.2 | 0.1 | 1.3 | 1.3 | 0.0 | 1.0 |

FIG. 16

| name | AGI | WT 8cm | 16cm | 24cm | 32cm |
|---|---|---|---|---|---|
| shikimate biosynthesis | | | | | |
| DHS1 | At4g39980 | -1.0 | -0.1 | 0.0 | 0.6 |
| DHS3 | At1g22410 | -1.8 | -0.2 | 0.0 | 1.0 |
| DQS | At5g66120 | -0.8 | -0.1 | 0.0 | 0.5 |
| EPSPS1 | At2g45300 | | 0.2 | 0.0 | -0.2 |
| CS | At1g48850 | | 0.2 | 0.0 | 0.6 |
| CM1 | At3g29200 | -0.8 | 0.2 | 0.0 | 1.0 |
| SK2 | At4g39540 | | 0.1 | 0.0 | 0.2 |
| ADT3 | At2g27820 | 0.6 | 0.2 | 0.0 | 0.7 |
| phenylpropanoid biosynthesis | | | | | |
| C4H | At2g30490 | -1.4 | -0.1 | 0.0 | 0.9 |
| PAL2 | At3g53260 | | 0.2 | 0.0 | 0.9 |
| PAL4 | At3g10340 | -2.3 | 0.3 | 0.0 | 0.7 |
| C3H | At2g40890 | | -0.4 | 0.0 | -1.3 |
| CCoAOMT1 | At4g34050 | -1.6 | | 0.0 | -1.1 |
| CAD2 | At3g19450 | -1.4 | -0.1 | 0.0 | -1.2 |
| methyldonor biosynthesis | | | | | |
| S-adenosyl-L-homocysteine hydrolase | At4g13940 | 0.1 | | 0.0 | -0.1 |
| S-adenosyl-L-homocysteine hydrolase 2 (SAH2) | At3g23810 | 0.1 | 0.1 | 0.0 | 1.4 |
| methionine synthase 2 | At3g03780 | -1.0 | -0.1 | 0.0 | 0.7 |
| SAM2 | At4g01850 | -0.7 | 0.2 | 0.0 | 0.0 |
| SAM3 | At2g36880 | -0.3 | 0.0 | 0.0 | 0.7 |
| methylenetetrahydrofolate reductase 1 | At3g59970 | 0.9 | | 0.0 | 0.0 |
| methylenetetrahydrofolate reductase 2 | At2g44160 | -1.2 | -0.2 | 0.0 | 1.0 |
| serine hydroxymethyltransferase 4 | At4g13930 | | 0.0 | 0.0 | -1.0 |
| transcription factors and signalling | | | | | |
| MYB58 | At1g16490 | | 0.7 | 0.0 | -2.1 |
| MYB123 | At5g35550 | 0.0 | 0.3 | 0.0 | |
| CCCH-type zinc finger | At1g66810 | 1.1 | 1.1 | 0.0 | 1.3 |
| WOX4 | At1g46480 | 0.8 | 0.7 | 0.0 | -0.9 |
| leucine-rich repeat protein kinase | At2g15300 | 1.2 | | 0.0 | |
| ralf-like 24 | At3g23805 | 1.3 | 1.0 | 0.0 | 1.3 |
| protein kinase superfamily protein | At1g70430 | -0.3 | | 0.0 | -0.9 |
| haloacid dehalogenase-like hydrolase (HAD) | At1g35910 | -0.7 | | 0.0 | -2.4 |

FIG. 17A

| name | AGI | WT 8cm | 16cm | 24cm | 32cm |
|---|---|---|---|---|---|
| transporters | | | | | |
| PHT4;2 | At2g38060 | -0.9 | 0.3 | 0.0 | -1.4 |
| PHT2;1 | At3g26570 | -1.0 | 0.8 | 0.0 | 0.7 |
| lipid transport | At1g24010 | -0.3 | 0.0 | 0.0 | -0.3 |
| other and unknown | | | | | |
| pinoresinol reductase 1 | At1g32100 | -1.5 | 0.3 | 0.0 | -1.3 |
| ASP4 | At1g62800 | 0.7 | 0.8 | 0.0 | 0.1 |
| AAT | At2g22250 | -0.8 | 0.2 | 0.0 | -1.3 |
| enolase 1 | At1g74030 | 0.1 | 0.2 | 0.0 | -1.1 |
| GDSL-like lipase/acylhydrolase | At1g28610 | 0.3 | 0.3 | 0.0 | 0.0 |
| GDSL-like lipase/acylhydrolase | At1g09390 | -1.2 | 0.7 | 0.0 | 0.0 |
| alpha/beta-hydrolase | At1g19190 | -1.4 | 0.7 | 0.0 | -0.7 |
| alpha/beta-hydrolase | At4g18550 | -2.0 | 0.1 | 0.0 | -1.2 |
| chalcone-flavanone isomerase | At5g05270 | 0.9 | 0.2 | 0.0 | -1.3 |
| hydratase/crotonase | At1g06550 | -0.9 | 0.3 | 0.0 | -0.8 |
| GroES-like zinc-binding dehydrogenase | At5g24760 | -1.4 | 0.3 | 0.0 | -1.5 |
| aldolase | At5g13420 | -1.4 | 0.3 | 0.0 | -2.3 |
| lysophospholipase 2 | At1g52760 | 1.7 | -0.2 | 0.0 | -0.8 |
| adenylate kinase family protein | At5g50370 | -1.3 | -1.1 | 0.0 | -0.6 |
| UDP-glucosyl transferase (UGT) 78D2 | At5g17050 | 0.1 | 0.4 | 0.0 | -0.7 |
| auxin-responsive GH3 | At5g54510 | -1.3 | 0.9 | 0.0 | -0.2 |
| terpenoid cyclase/Protein prenyltransferase | At1g66020 | -0.6 | 0.3 | 0.0 | 0.3 |
| cytochrome B5 isoform B | At2g32720 | -1.1 | 0.2 | 0.0 | -0.9 |
| phosphofructokinase | At1g76550 | 0.2 | 0.3 | 0.0 | -0.2 |
| tetraspanin15 | At5g57810 | 0.2 | 0.2 | 0.0 | -1.4 |
| glutathione S-transferase TAU 18 | At1g10360 | 0.9 | 0.7 | 0.0 | -1.1 |
| unknown | At1g52565 | 0.7 | 0.9 | 0.0 | -0.6 |
| unknown | At4g30230 | -1.0 | 0.1 | 0.0 | -0.7 |
| unknown | At5g03670 | -1.2 | 0.8 | 0.0 | -1.0 |
| unknown | At5g42690 | -0.2 | 0.3 | 0.0 | -0.9 |
| unknown | At5g45530 | 0.9 | 0.4 | 0.0 | -0.6 |
| unknown | At5g47870 | 0.0 | 0.7 | 0.0 | -0.5 |
| unknown | At5g54530 | 0.8 | 0.8 | 0.0 | -1.5 |
| unknown | At2g14520 | 0.9 | 0.7 | 0.0 | 0.8 |

SEQUENCE LISTING

<160> NUMBER OF SEQ ID NOS: 28

<210> SEQ ID NO 1
<211> LENGTH: 1317
<212> TYPE: DNA
<213> ORGANISM: Arabidopsis Thaliana

<400> SEQUENCE: 1

```
atggcaacca tttcgaatct cgctaatctt ccccgcgcca cctgcgtcga ctccaaatct      60
tcttcctctt cctccgtctt acctagatcc ttcgtcaatt tccgcgcttt gaatgcaaag     120
ctttcctctt ctcagctttc tcttcgttat aaccaacgat caataccttc cctctctgtg     180
aggtgttcag tgtctggtgg aaatggaact gctggaaaga gaacgactct tcatgatcta     240
tatgagaagg aaggtcagag tccttggtat gataatcttt gccgtccagt cacagatctt     300
ctcccgttga ttgctcgtgg tgttagaggt gttactagca accctgcgat cttccaaaaa     360
gccatttcca cttcaaatgc ttataatgat caattcagga cacttgtgga atcgggaaag     420
```

```
gacattgaaa gtgcgtattg ggaacttgtg gtgaaggata ttcaggatgc ctgcaaactt    480
tttgagccaa tctatgacca gacagaaggt gcggatggct atgtctctgt tgaagtttca    540
cctaggcttg ctgatgatac ccaaggaact gttgaagctg ctaaatatct tagcaaggtt    600
gtcaaccgtc gtaatgtcta cattaagatt cctgctactg ctccatgcat tccttccatc    660
agggatgtca ttgcagctgg aataagtgtc aatgtcacgc ttatattctc aatcgccaga    720
tatgaagcag tgatcgatgc atatttggat ggcctcgagg cgtctggact tgatgacctc    780
tcaagagtta ccagtgttgc ttccttcttt gtcagtcggg tggatactct catggacaag    840
atgcttgagc aaattggtac ccctgaagcc ttagatctcc gtgggaaggc ggctgtggct    900
caagctgcat tagcatacaa gctataccag cagaaattct ctggcccaag atgggaagct    960
ctggtaaaga aggtgccaa gaaacagaga cttctctggg catcaacaag tgtaaagaac    1020
ccagcttact ctgacacctt atatgtcgct cctctcatcg acctgacac tgtatcaacc    1080 atgccggatc aagccctgga agcattcgca gatcatggaa tagtgaagag acaatagat    1140 gcgaatgtgt cagaagcaga agggatttac agtgcactag agaagctggg aatagactgg    1200
aacaaagtag gagaacagtt ggaagacgaa ggagtagatt ccttcaagaa gagtttcgag    1260
agtctgctcg gtacactgca agacaaggcc aacactctca aactagccag ccattga      1317
```

<210> SEQ ID NO 2
<211> LENGTH: 438
<212> TYPE: PRT
<213> ORGANISM: Arabidopsis Thaliana

<400> SEQUENCE: 2

```
Met Ala Thr Ile Ser Asn Leu Ala Asn Leu Pro Arg Ala Thr Cys Val
1               5                   10                  15

Asp Ser Lys Ser Ser Ser Ser Ser Val Leu Pro Arg Ser Phe Val
            20                  25                  30

Asn Phe Arg Ala Leu Asn Ala Lys Leu Ser Ser Ser Gln Leu Ser Leu
        35                  40                  45

Arg Tyr Asn Gln Arg Ser Ile Pro Ser Leu Ser Val Arg Cys Ser Val
    50                  55                  60

Ser Gly Gly Asn Gly Thr Ala Gly Lys Arg Thr Thr Leu His Asp Leu
65                  70                  75                  80

Tyr Glu Lys Glu Gly Gln Ser Pro Trp Tyr Asp Asn Leu Cys Arg Pro
                85                  90                  95

Val Thr Asp Leu Leu Pro Leu Ile Ala Arg Gly Val Arg Gly Val Thr
            100                 105                 110

Ser Asn Pro Ala Ile Phe Gln Lys Ala Ile Ser Thr Ser Asn Ala Tyr
        115                 120                 125

Asn Asp Gln Phe Arg Thr Leu Val Glu Ser Gly Lys Asp Ile Glu Ser
    130                 135                 140

Ala Tyr Trp Glu Leu Val Val Lys Asp Ile Gln Asp Ala Cys Lys Leu
145                 150                 155                 160

Phe Glu Pro Ile Tyr Asp Gln Thr Glu Gly Ala Asp Gly Tyr Val Ser
                165                 170                 175

Val Glu Val Ser Pro Arg Leu Ala Asp Asp Thr Gln Gly Thr Val Glu
            180                 185                 190

Ala Ala Lys Tyr Leu Ser Lys Val Val Asn Arg Arg Asn Val Tyr Ile
        195                 200                 205

Lys Ile Pro Ala Thr Ala Pro Cys Ile Pro Ser Ile Arg Asp Val Ile
```

```
               210                 215                 220
Ala Ala Gly Ile Ser Val Asn Val Thr Leu Ile Phe Ser Ile Ala Arg
225                 230                 235                 240

Tyr Glu Ala Val Ile Asp Ala Tyr Leu Asp Gly Leu Glu Ala Ser Gly
                245                 250                 255

Leu Asp Asp Leu Ser Arg Val Thr Ser Val Ala Ser Phe Phe Val Ser
                    260                 265                 270

Arg Val Asp Thr Leu Met Asp Lys Met Leu Glu Gln Ile Gly Thr Pro
            275                 280                 285

Glu Ala Leu Asp Leu Arg Gly Lys Ala Ala Val Ala Gln Ala Ala Leu
        290                 295                 300

Ala Tyr Lys Leu Tyr Gln Gln Lys Phe Ser Gly Pro Arg Trp Glu Ala
305                 310                 315                 320

Leu Val Lys Lys Gly Ala Lys Lys Gln Arg Leu Leu Trp Ala Ser Thr
                325                 330                 335

Ser Val Lys Asn Pro Ala Tyr Ser Asp Thr Leu Tyr Val Ala Pro Leu
                    340                 345                 350

Ile Gly Pro Asp Thr Val Ser Thr Met Pro Asp Gln Ala Leu Glu Ala
            355                 360                 365

Phe Ala Asp His Gly Ile Val Lys Arg Thr Ile Asp Ala Asn Val Ser
        370                 375                 380

Glu Ala Glu Gly Ile Tyr Ser Ala Leu Glu Lys Leu Gly Ile Asp Trp
385                 390                 395                 400

Asn Lys Val Gly Glu Gln Leu Glu Asp Glu Gly Val Asp Ser Phe Lys
                405                 410                 415

Lys Ser Phe Glu Ser Leu Leu Gly Thr Leu Gln Asp Lys Ala Asn Thr
                    420                 425                 430

Leu Lys Leu Ala Ser His
            435

<210> SEQ ID NO 3
<211> LENGTH: 1284
<212> TYPE: DNA
<213> ORGANISM: Arabidopsis Thaliana

<400> SEQUENCE: 3
atgccactct cgttgcaatc tccgccttgt gcaactctct ctgcttcaat ccgaaaggga      60
cgatggaaga cgctcgccgc cggattctcc gttactcctc ttcccgccgt taacttcagt     120
cttcggcgat cgattcctcg gattcttgct tccgctagtt cctcctcctc tcctgcgtct     180
tcgtctctcg aagctggtga gaacaatgag ctaaatgctg tttcagcttt tagtgagatt     240
gttcctgata ctgtcgtttt cgatgacttt gagagttttt ctctggatcg aggatacaag     300
aaagaaatta gcttaagatg taaaaactca ctccctcaca gtttccgcc gactgcagct     360 actgttagct ctgctcttct tctgggtatc tgtggtctac ctgataccat tttccgcaat     420
gctgtggaca tggctttggc ggattcttct tgtgcagggc ttgaaaccac agaatctcga     480
ctctcttgct ttttcaataa ggctattgtc aacgtaggtg gcgatcttgt caaactcgtt     540
ccaggtcgag tttctactga agtggatgca cgtcttgctt atgacacaaa tggcattatc     600
cgcaaggttc atgatctgct gagactatac aatgaaatcg atgtaccaca cgaccggctc     660
ctattcaaaa tccctgcaac ttggcaaggt attgaagctg caagattgtt ggaatcagag     720
ggaatccaaa cgcatatgac ctttgtttac agctttgcac aagctgcagc agcttctcaa     780
gccggtgctt ctgtcattca gattttcgtc ggtcgcctca gggattgggc gcgtaatcat     840
```

```
tcgggagata ccgagattga atctgctatt aaatcgggag aagatcctgg tttggccttg    900
gtcaaaagat catataacta cattcacaag tatggttaca agtccaagct gatggctgct    960
gctgtccgga acaaacaaga cttgttcagt cttctcgggg tcgattatgt cattgcacca   1020
ttaaaggtac tgcaatctct taaagattca cccgccattc ccgatgatga aaaatactca   1080
tttgttcgga aacttactcc tgaaactgca acacattacc acttcaccaa caaagagctg   1140
gtcaatgggg accagctaag cttggcttca tctatgggtc ctgcatcagt ggagctttta   1200
tcagccggtg ttgaaggtta tgcgaaccaa gcgaaacgtg ttgaagagct tttcgggaag   1260
atttggccac ctcctaatgt ctaa                                          1284
```

<210> SEQ ID NO 4
<211> LENGTH: 427
<212> TYPE: PRT
<213> ORGANISM: Arabidopsis Thaliana

<400> SEQUENCE: 4

Met Pro Leu Ser Leu Gln Ser Pro Pro Cys Ala Thr Leu Ser Ala Ser
1               5                   10                  15

Ile Arg Lys Gly Arg Trp Lys Thr Leu Ala Ala Gly Phe Ser Val Thr
            20                  25                  30

Pro Leu Pro Ala Val Asn Phe Ser Leu Arg Arg Ser Ile Pro Arg Ile
        35                  40                  45

Leu Ala Ser Ala Ser Ser Ser Ser Pro Ala Ser Ser Ser Leu Glu
    50                  55                  60

Ala Gly Glu Asn Asn Glu Leu Asn Ala Val Ala Phe Ser Glu Ile
65                  70                  75                  80

Val Pro Asp Thr Val Val Phe Asp Phe Glu Ser Phe Ser Leu Asp
                85                  90                  95

Arg Gly Tyr Lys Lys Glu Ile Ser Leu Arg Cys Lys Asn Ser Leu Pro
            100                 105                 110

His Lys Phe Pro Pro Thr Ala Ala Thr Val Ser Ser Ala Leu Leu Leu
        115                 120                 125

Gly Ile Cys Gly Leu Pro Asp Thr Ile Phe Arg Asn Ala Val Asp Met
    130                 135                 140

Ala Leu Ala Asp Ser Ser Cys Ala Gly Leu Glu Thr Thr Glu Ser Arg
145                 150                 155                 160

Leu Ser Cys Phe Phe Asn Lys Ala Ile Val Asn Val Gly Gly Asp Leu
                165                 170                 175

Val Lys Leu Val Pro Gly Arg Val Ser Thr Glu Val Asp Ala Arg Leu
            180                 185                 190

Ala Tyr Asp Thr Asn Gly Ile Ile Arg Lys Val His Asp Leu Leu Arg
        195                 200                 205

Leu Tyr Asn Glu Ile Asp Val Pro His Asp Arg Leu Leu Phe Lys Ile
    210                 215                 220

Pro Ala Thr Trp Gln Gly Ile Glu Ala Ala Arg Leu Leu Glu Ser Glu
225                 230                 235                 240

Gly Ile Gln Thr His Met Thr Phe Val Tyr Ser Phe Ala Gln Ala Ala
                245                 250                 255

Ala Ala Ser Gln Ala Gly Ala Ser Val Ile Gln Ile Phe Val Gly Arg
            260                 265                 270

Leu Arg Asp Trp Ala Arg Asn His Ser Gly Asp Thr Glu Ile Glu Ser
        275                 280                 285

```
Ala Ile Lys Ser Gly Glu Asp Pro Gly Leu Ala Leu Val Lys Arg Ser
    290                 295                 300

Tyr Asn Tyr Ile His Lys Tyr Gly Tyr Lys Ser Lys Leu Met Ala Ala
305                 310                 315                 320

Ala Val Arg Asn Lys Gln Asp Leu Phe Ser Leu Leu Gly Val Asp Tyr
                325                 330                 335

Val Ile Ala Pro Leu Lys Val Leu Gln Ser Leu Lys Asp Ser Pro Ala
            340                 345                 350

Ile Pro Asp Asp Glu Lys Tyr Ser Phe Val Arg Lys Leu Thr Pro Glu
        355                 360                 365

Thr Ala Thr His Tyr His Phe Thr Asn Lys Glu Leu Val Lys Trp Asp
370                 375                 380

Gln Leu Ser Leu Ala Ser Ser Met Gly Pro Ala Ser Val Glu Leu Leu
385                 390                 395                 400

Ser Ala Gly Val Glu Gly Tyr Ala Asn Gln Ala Lys Arg Val Glu Glu
                405                 410                 415

Leu Phe Gly Lys Ile Trp Pro Pro Pro Asn Val
            420                 425
```

<210> SEQ ID NO 5
<211> LENGTH: 1323
<212> TYPE: DNA
<213> ORGANISM: Populus trichocarpa

<400> SEQUENCE: 5

```
atggctacaa tttcaaagct atcaaatcca agccctgctg cctctctacc agctccttct      60
tcttcttctt ctttgcctag agttttcctt ggtttcaata ccaaaacttc tttctccaaa     120
gttgcatcat cttcttctgg gttgtctttg acaaacaccc aaccttggag acctcctttt     180
gttgtcaggt gctctcaatc cagtggaaat ggtagtccga taagagaaac tacccttcat     240
gatctctatg aacgggaggg gcagagtcca tggtatgaca acctctgcag gcctgtgacg     300
gatctgattc ctctgatcga gagtggagtc agaggtgtaa cgagtaaccc agcgattttc     360
cagaaggcaa tatcatcttc aaatgcttac aatgaccaat tcagagaact tgtgcaagcg     420
ggaaaagaca ttgaaactgc ttactgggaa cttgtggtga aggacataca agacgcatgc     480
aaacttttcg agccaatata tgatcaaaca gatggtggtg atggctatgt ttctgttgaa     540
gtgtctccca gactagctga tgatactcaa gggactgttg aggctgcaaa gtggcttcat     600
aaagtggttg atcgccccaa cgtgtacatt aaaattcccg ctactgctcc ttgcatcccc     660
tcaatcaagg aagttatttc tcttggcatc agtgtcaatg tgactctgat attctctctc     720
accagatatg aagcggtcat tgatgcctac ttggatggcc ttgaggcatc tggactaagt     780
gacctctcca gagttacaag tgttgcttcc ttctttgtca gtagggtgga cactctcatt     840
gacaaaatgc tagaaaagat cggaaccccca gaagcccttg atctacgagg aaaggctgct     900
gtggctcaag caggcctagc atacaagctc taccaaagaa aattctcagg tccaagatgg     960
gaggctttgg tgaagaaagg tgctaagaag cagaggttgc tgtgggcatc aaccagtgtc    1020
aagaaccctg cctacccaga cactttatat gttgctcccc tcattggacc tgacacagtc    1080
tcaaccatgc ctgaccaagc tctccaagca tttgttgatc atggaagtgt tgcaaggaca    1140
atcgactcaa atgtttctga agctgaagga atttacaatg cacttgagaa gttgggaatt    1200
gattggggct acgtgggaga ccaacttgaa gttgaaggag tggattcttt caagaagagc    1260
ttcgatagtc tgcttgatac cctgcaagag aaggcaaatt ctctgaaatt ggttagcccg    1320
``` taa                                                                1323

<210> SEQ ID NO 6
<211> LENGTH: 440
<212> TYPE: PRT
<213> ORGANISM: Populus trichocarpa

<400> SEQUENCE: 6

```
Met Ala Thr Ile Ser Lys Leu Ser Asn Pro Ser Pro Ala Ala Ser Leu
1               5                   10                  15

Pro Ala Pro Ser Ser Ser Ser Leu Pro Arg Val Phe Leu Gly Phe
            20                  25                  30

Asn Thr Lys Thr Ser Phe Ser Lys Val Ala Ser Ser Ser Gly Leu
        35                  40                  45

Ser Leu Thr Asn Thr Gln Pro Trp Arg Thr Ser Phe Val Val Arg Cys
    50                  55                  60

Ser Gln Ser Ser Gly Asn Gly Ser Pro Ile Lys Arg Thr Thr Leu His
65                  70                  75                  80

Asp Leu Tyr Glu Arg Glu Gly Gln Ser Pro Trp Tyr Asp Asn Leu Cys
                85                  90                  95

Arg Pro Val Thr Asp Leu Ile Pro Leu Ile Glu Ser Gly Val Arg Gly
            100                 105                 110

Val Thr Ser Asn Pro Ala Ile Phe Gln Lys Ala Ile Ser Ser Ser Asn
        115                 120                 125

Ala Tyr Asn Asp Gln Phe Arg Glu Leu Val Gln Ala Gly Lys Asp Ile
    130                 135                 140

Glu Thr Ala Tyr Trp Glu Leu Val Val Lys Asp Ile Gln Asp Ala Cys
145                 150                 155                 160

Lys Leu Phe Glu Pro Ile Tyr Asp Gln Thr Asp Gly Gly Asp Gly Tyr
                165                 170                 175

Val Ser Val Glu Val Ser Pro Arg Leu Ala Asp Asp Thr Gln Gly Thr
            180                 185                 190

Val Glu Ala Ala Lys Trp Leu His Lys Val Val Asp Arg Pro Asn Val
        195                 200                 205

Tyr Ile Lys Ile Pro Ala Thr Ala Pro Cys Ile Pro Ser Ile Lys Glu
    210                 215                 220

Val Ile Ser Leu Gly Ile Ser Val Asn Val Thr Leu Ile Phe Ser Leu
225                 230                 235                 240

Thr Arg Tyr Glu Ala Val Ile Asp Ala Tyr Leu Asp Gly Leu Glu Ala
                245                 250                 255

Ser Gly Leu Ser Asp Leu Ser Arg Val Thr Ser Val Ala Ser Phe Phe
            260                 265                 270

Val Ser Arg Val Asp Thr Leu Ile Asp Lys Met Leu Glu Lys Ile Gly
        275                 280                 285

Thr Pro Glu Ala Leu Asp Leu Arg Gly Lys Ala Ala Val Ala Gln Ala
    290                 295                 300

Gly Leu Ala Tyr Lys Leu Tyr Gln Lys Lys Phe Ser Gly Pro Arg Trp
305                 310                 315                 320

Glu Ala Leu Val Lys Lys Gly Ala Lys Lys Gln Arg Leu Leu Trp Ala
                325                 330                 335

Ser Thr Ser Val Lys Asn Pro Ala Tyr Pro Asp Thr Leu Tyr Val Ala
            340                 345                 350

Pro Leu Ile Gly Pro Asp Thr Val Ser Thr Met Pro Asp Gln Ala Leu
        355                 360                 365
```

```
Gln Ala Phe Val Asp His Gly Ser Val Ala Arg Thr Ile Asp Ser Asn
        370                 375                 380

Val Ser Glu Ala Glu Gly Ile Tyr Asn Ala Leu Glu Lys Leu Gly Ile
385                 390                 395                 400

Asp Trp Gly Tyr Val Gly Asp Gln Leu Glu Val Glu Gly Val Asp Ser
                405                 410                 415

Phe Lys Lys Ser Phe Asp Ser Leu Leu Asp Thr Leu Gln Glu Lys Ala
            420                 425                 430

Asn Ser Leu Lys Leu Val Ser Pro
        435                 440

<210> SEQ ID NO 7
<211> LENGTH: 1311
<212> TYPE: DNA
<213> ORGANISM: Populus trichocarpa

<400> SEQUENCE: 7
```

| | | | | | |
|---|---|---|---|---|---|
| atggctacca | tttcaaagct | ctcaaatcca | agccccgcag | cctccctctc | agctccttct | 60 |
| agatcttctt | ccttgcctaa | agtcttcctc | ggtttcagta | ccaaaacttc | tctctccaaa | 120 |
| gttaggctgt | ccttgaagaa | cacccaaccg | tcccccagga | cctccttggt | tgtcaggtgt | 180 |
| tctcaatcca | gtggaaatgg | tagcccaata | aagagaacca | ctcttcatga | tctttatgaa | 240 |
| cgggaggggc | agagtccatg | gtatgacaac | tctctgcagg | ctgtgacgga | cctgattcct | 300 |
| ctgatcgaga | gtggagttag | aggcgtaaca | agcaacccag | cgattttcca | gaaggcaata | 360 |
| tcatcttcaa | atgcttacaa | tgaccaattc | agggaacttg | tgcaatcagg | aaaagacatt | 420 |
| gaaactgctt | actgggaact | tgtggtgaag | gacatacaag | atgcatgcaa | acttttgag | 480 |
| tcaatttatg | atcaaacaga | tggtggtgat | ggctatgttt | ctgttgaagt | gtctcccaga | 540 |
| ttagctgatg | acactcaagg | gactgttgag | gctgccaagt | ggcttcataa | agtggttgat | 600 |
| cgccccaatg | tgtacattaa | aatccctgct | actgctcctt | gcatcccctc | aatcaaggaa | 660 |
| gttatttcgc | ttggcatcag | tgtcaatgtg | actctgatat | tctctctcac | aagatacgaa | 720 |
| gcagtcattg | atgcctactt | ggatggcctt | gaggcatctg | gactaagtga | tctctccaga | 780 |
| gttacaagtg | ttgcttcctt | ctttgtcagc | agggtggaca | ctctcattga | caaaatgctg | 840 |
| gaaaagatcg | gaacccctga | agcccttgat | ctacgaggaa | aggctgcggt | ggctcaagca | 900 |
| gccctagcat | acaagctcta | ccaaaagaaa | ttctctggtc | aagatgggga | ggctttggtg | 960 |
| aaaaaaggtg | ctaagaagca | gaggttgctg | tgggcatcaa | ccagtgtcaa | gaaccctgcc | 1020 |
| tacccagaca | ctttatacgt | tgctcccctc | attggacctg | acactgtctc | aaccatgcct | 1080 |
| gaccaagctc | tccaagcatt | tgttgaccat | ggaattgttg | caaggacaat | cgactcaaat | 1140 |
| gtttctgaag | ccgaaggaat | ctacaacgca | cttgagaagt | tgggaattga | ttggggctac | 1200 |
| gtgggcaatc | agcttgaagt | tgaaggagtg | gattctttca | agaagagctt | tgatagtctg | 1260 |
| cttgatccc | tgcaagagaa | ggcaaattct | ctgaaactgg | ttagcctgta | a | 1311 |

```
<210> SEQ ID NO 8
<211> LENGTH: 436
<212> TYPE: PRT
<213> ORGANISM: Populus trichocarpa

<400> SEQUENCE: 8

Met Ala Thr Ile Ser Lys Leu Ser Asn Pro Ser Pro Ala Ala Ser Leu
1               5                   10                  15

Ser Ala Pro Ser Arg Ser Ser Ser Leu Pro Lys Val Phe Leu Gly Phe
```

```
            20                  25                  30
Ser Thr Lys Thr Ser Leu Ser Lys Val Arg Leu Ser Leu Lys Asn Thr
        35                  40                  45
Gln Pro Ser Pro Arg Thr Ser Leu Val Val Arg Cys Ser Gln Ser Ser
    50                  55                  60
Gly Asn Gly Ser Pro Ile Lys Arg Thr Thr Leu His Asp Leu Tyr Glu
65                  70                  75                  80
Arg Glu Gly Gln Ser Pro Trp Tyr Asp Asn Leu Cys Arg Pro Val Thr
                85                  90                  95
Asp Leu Ile Pro Leu Ile Glu Ser Gly Val Arg Gly Val Thr Ser Asn
            100                 105                 110
Pro Ala Ile Phe Gln Lys Ala Ile Ser Ser Asn Ala Tyr Asn Asp
        115                 120                 125
Gln Phe Arg Glu Leu Val Gln Ser Gly Lys Asp Ile Glu Thr Ala Tyr
    130                 135                 140
Trp Glu Leu Val Val Lys Asp Ile Gln Asp Ala Cys Lys Leu Phe Glu
145                 150                 155                 160
Ser Ile Tyr Asp Gln Thr Asp Gly Gly Asp Gly Tyr Val Ser Val Glu
                165                 170                 175
Val Ser Pro Arg Leu Ala Asp Asp Thr Gln Gly Thr Val Glu Ala Ala
            180                 185                 190
Lys Trp Leu His Lys Val Val Asp Arg Pro Asn Val Tyr Ile Lys Ile
        195                 200                 205
Pro Ala Thr Ala Pro Cys Ile Pro Ser Ile Lys Glu Val Ile Ser Leu
    210                 215                 220
Gly Ile Ser Val Asn Val Thr Leu Ile Phe Ser Leu Thr Arg Tyr Glu
225                 230                 235                 240
Ala Val Ile Asp Ala Tyr Leu Asp Gly Leu Glu Ala Ser Gly Leu Ser
                245                 250                 255
Asp Leu Ser Arg Val Thr Ser Val Ala Ser Phe Phe Val Ser Arg Val
            260                 265                 270
Asp Thr Leu Ile Asp Lys Met Leu Glu Lys Ile Gly Thr Pro Glu Ala
        275                 280                 285
Leu Asp Leu Arg Gly Lys Ala Ala Val Ala Gln Ala Ala Leu Ala Tyr
    290                 295                 300
Lys Leu Tyr Gln Lys Lys Phe Ser Gly Pro Arg Trp Glu Ala Leu Val
305                 310                 315                 320
Lys Lys Gly Ala Lys Lys Gln Arg Leu Leu Trp Ala Ser Thr Ser Val
                325                 330                 335
Lys Asn Pro Ala Tyr Pro Asp Thr Leu Tyr Val Ala Pro Leu Ile Gly
            340                 345                 350
Pro Asp Thr Val Ser Thr Met Pro Asp Gln Ala Leu Gln Ala Phe Val
        355                 360                 365
Asp His Gly Ile Val Ala Arg Thr Ile Asp Ser Asn Val Ser Glu Ala
    370                 375                 380
Glu Gly Ile Tyr Asn Ala Leu Glu Lys Leu Gly Ile Asp Trp Gly Tyr
385                 390                 395                 400
Val Gly Asn Gln Leu Glu Val Glu Gly Val Asp Ser Phe Lys Lys Ser
                405                 410                 415
Phe Asp Ser Leu Leu Asp Thr Leu Gln Glu Lys Ala Asn Ser Leu Lys
            420                 425                 430
Leu Val Ser Leu
        435
```

<210> SEQ ID NO 9
<211> LENGTH: 930
<212> TYPE: DNA
<213> ORGANISM: Oryza sativa ssp. indica

<400> SEQUENCE: 9

```
aggaagggcg cgacgtgct ggaggacgac ccgacgggga agctgaaggt gttcgtgtac      60
gagatgccac gcaagtacaa cctgaacctg ctggccaagg acagccggtg cctgcagcac    120
atgttcgcgg cggagatctt catgcaccag ttcctcctct cagcccctgc gatggcttct    180
gccaaggaag gaaatggtgc cccaacgaag aggacaaccc ttcatgatct ctatgatctc    240
cagggtcagt ccccgtggta cgacaacctc tgccgtcctg tcaccgattt gctgcccctt    300
attggcagcg cgtccgtgg agtcaccagc aacccatcag tacgctacac tacttatttc    360
ttttgctctc ttgcaccttg ttctgaacct gcaatcctca ttgctgactg tgtccctatg    420
gcaatgcaga ttttccagaa agccatctcg acttccaatg catacgatga ccagttcaag    480
cagcttatat tagctggaaa ggacgcagag agcgcttatt gggaacttgt catcaaggat    540
atccaagatg cgtgcaaact tttcgagcct atctatgacc agaccgatgg ggcagatggg    600
tatgtttctg tggaggtctc ccctaggctg gcaaatgata cccagggaac tgttgaagct    660
gcaaaatggt tgcacaaagt ggtcgacagg cccaatgtct acataaagat ccctgctacc    720
gcagaatgtg ttccttctat caaggaagtt attgctaatg gcattagtgt caacgtcaca    780
cttatcttct cgattgcaag atacgaggct gtgattgatg cttacattga tggacttgag    840
gcctctggtt tgagtgacct atcccgagtg accagtgtag cgtccttctt tgggggtaat    900
tcagacaacc gcgatagttc gggggtgtaa                                      930
```

<210> SEQ ID NO 10
<211> LENGTH: 416
<212> TYPE: PRT
<213> ORGANISM: Oryza sativa ssp. indica

<400> SEQUENCE: 10

```
Met Glu Arg Leu Ala Asp Pro His Leu Ala Leu Ser His Gly Thr Gly
 1               5                  10                  15

Thr Gln Ala Ser Arg Gln Lys Pro Asp Gly Glu Pro Gln Leu Gln Pro
            20                  25                  30

Gln Ile Ala Phe Arg Ser Ser Thr Asn Asn Ile Arg Glu Arg Ser Phe
        35                  40                  45

Gly Arg Ser Gly Gln Glu Pro Ala Ala Gly Arg Val Gly Trp Val Arg
    50                  55                  60

Gly Ala Pro Leu Thr Trp Leu Ser Ser Ala Gly Leu Gly Asp Gly Glu
65                  70                  75                  80

Leu Asp Val Ala Gly Gly His Arg Gly Gly Gly Ala Ala Arg Arg
                85                  90                  95

Gly Gly Gly Ser Gly Gly Ile Trp Gly Arg Arg Lys Gly Gly Asp
            100                 105                 110

Val Leu Glu Asp Asp Pro Thr Gly Lys Leu Lys Val Phe Val Tyr Glu
        115                 120                 125

Met Pro Arg Lys Tyr Asn Leu Asn Leu Leu Ala Lys Asp Ser Arg Cys
    130                 135                 140

Leu Gln His Met Phe Ala Ala Glu Ile Phe Met His Gln Phe Leu Leu
145                 150                 155                 160
```

Ser Ala Pro Ala Met Ala Ser Ala Lys Glu Gly Asn Gly Ala Pro Thr
              165                 170                 175

Lys Arg Thr Thr Leu His Asp Leu Tyr Asp Leu Gln Gly Gln Ser Pro
            180                 185                 190

Trp Tyr Asp Asn Leu Cys Arg Pro Val Thr Asp Leu Leu Pro Leu Ile
            195                 200                 205

Gly Ser Gly Val Arg Gly Val Thr Ser Asn Pro Ser Val Arg Tyr Thr
        210                 215                 220

Thr Tyr Phe Phe Cys Ser Leu Ala Pro Cys Ser Glu Pro Ala Ile Leu
225                 230                 235                 240

Ile Ala Asp Cys Val Pro Met Ala Met Gln Ile Phe Gln Lys Ala Ile
                245                 250                 255

Ser Thr Ser Asn Ala Tyr Asp Asp Gln Phe Lys Gln Leu Ile Leu Ala
                260                 265                 270

Gly Lys Asp Ala Glu Ser Ala Tyr Trp Glu Leu Val Ile Lys Asp Ile
            275                 280                 285

Gln Asp Ala Cys Lys Leu Phe Glu Pro Ile Tyr Asp Gln Thr Asp Gly
            290                 295                 300

Ala Asp Gly Tyr Val Ser Val Glu Val Ser Pro Arg Leu Ala Asn Asp
305                 310                 315                 320

Thr Gln Gly Thr Val Glu Ala Ala Lys Trp Leu His Lys Val Val Asp
                325                 330                 335

Arg Pro Asn Val Tyr Ile Lys Ile Pro Ala Thr Ala Glu Cys Val Pro
            340                 345                 350

Ser Ile Lys Glu Val Ile Ala Asn Gly Ile Ser Val Asn Val Thr Leu
            355                 360                 365

Ile Phe Ser Ile Ala Arg Tyr Glu Ala Val Ile Asp Ala Tyr Ile Asp
        370                 375                 380

Gly Leu Glu Ala Ser Gly Leu Ser Asp Leu Ser Arg Val Thr Ser Val
385                 390                 395                 400

Ala Ser Phe Phe Gly Gly Asn Ser Asp Asn Arg Asp Ser Ser Gly Val
                405                 410                 415

<210> SEQ ID NO 11
<211> LENGTH: 1235
<212> TYPE: DNA
<213> ORGANISM: Oryza sativa ssp. indica

<400> SEQUENCE: 11
atgcgatggc ttctgccaag gaaggaaatg gtgccccaac gaagaggaca acccttcatg      60
atctctatga tctccagggt cagtcccgt ggtacgacaa cctctgccgt cctgtcaccg     120
atttgctgcc ccttattggc agcggcgtcc gtggagtcac cagcaaccca tcagtacgct     180
acactactta tttcttttgc tctcttgcac cttgttctga acctgcaatc ctcattgctg     240
actgtgtccc tatggcaatg cagatttttc agaaagccat ctcgacttcc aatgcatacg     300
atgaccagtt caagcagctt atattagctg gaaaggacgc agagagcgct tattgggaac     360
ttgtcatcaa ggatatccaa gatgcgtgca aacttttcga gcctatctat gaccagaccg     420
atggggcaga tggtatgtt tctgtggagg tctcccctag gctggcaaat gatacccagg     480
gaactgttga agctgcaaaa tggttgcaca agtggtcga caggcccaat gtctacataa     540
agatccctgc taccgcagaa tgtgttcctt ctatcaagga agttattgct aatggcatta     600
gtgtcaacgt cacacttatc ttctcgattg caagatacga ggctgtgatt gatgcttaca     660
ttgatggact tgaggcctct ggtttgagtg acctatcccg agtgaccagt gtagcgtcct     720

```
tctttgtcag ccgagttgac acacttattg acaaaatgct cgagaagatc ggaacacctg    780
aggcacttgc cctcagagga aaggctgctg tagcacaggc aaagctagcc aaccagcttt    840
accagaagaa attctctggc ccgaggtggg aggctttggt caagaaaggt gccaagaagc    900
agaggttgtt gtgggcatct accagtgtga agaaccctgc atacccagac actctttacg    960
tggatcctct catcggacct gacaccgttt ctaccatgcc cgaccaagct ctgctggcat   1020
tcatcgacca cggcacagtt tcgaggacaa tcgacgcaaa cgtttcggat gctgaaggtg   1080
tatacagtgc cctggagaag ctgggtatag attgggatga ggttggcaag cagctagagc   1140
tggaaggtgt ggactccttc aagaaggcct tcgacagcct gcttgggagc ttggaggaga   1200
agggcaattc cctcaagaag accgtgagcc tgtag                              1235
```

<210> SEQ ID NO 12
<211> LENGTH: 462
<212> TYPE: PRT
<213> ORGANISM: Oryza sativa ssp. indica

<400> SEQUENCE: 12

Met Thr Gly Ala Val Ser Lys Leu Ala Ala Pro Arg Pro Ala Ala Ala
1               5                   10                  15

Ala Pro Leu Pro Pro Ala Ser Val Arg Ser Ala Phe Leu Ala Ser Ala
            20                  25                  30

Pro Ser Pro Arg Arg Phe Ser Val Ser Ile Ala Ala Gly Arg Ala Arg
        35                  40                  45

Ser Pro Ile Ile Ala Met Ala Ser Ala Lys Glu Gly Asn Gly Ala Pro
    50                  55                  60

Thr Lys Arg Thr Thr Leu His Asp Leu Tyr Asp Leu Gln Gly Gln Ser
65                  70                  75                  80

Pro Trp Tyr Asp Asn Leu Cys Arg Pro Val Thr Asp Leu Leu Pro Leu
                85                  90                  95

Ile Gly Ser Gly Val Arg Gly Val Thr Ser Asn Pro Ser Val Arg Tyr
            100                 105                 110

Thr Thr Tyr Phe Phe Cys Ser Leu Ala Pro Cys Ser Glu Pro Ala Ile
        115                 120                 125

Leu Ile Ala Asp Cys Val Pro Met Ala Met Gln Ile Phe Gln Lys Ala
    130                 135                 140

Ile Ser Thr Ser Asn Ala Tyr Asp Asp Gln Phe Lys Gln Leu Ile Leu
145                 150                 155                 160

Ala Gly Lys Asp Ala Glu Ser Ala Tyr Trp Glu Leu Val Ile Lys Asp
                165                 170                 175

Ile Gln Asp Ala Cys Lys Leu Phe Glu Pro Ile Tyr Asp Gln Thr Asp
            180                 185                 190

Gly Ala Asp Gly Tyr Val Ser Val Glu Val Ser Pro Arg Leu Ala Asn
        195                 200                 205

Asp Thr Gln Gly Thr Val Glu Ala Ala Lys Trp Leu His Lys Val Val
    210                 215                 220

Asp Arg Pro Asn Val Tyr Ile Lys Ile Pro Ala Thr Ala Glu Cys Val
225                 230                 235                 240

Pro Ser Ile Lys Glu Val Ile Ala Asn Gly Ile Ser Val Asn Val Thr
                245                 250                 255

Leu Ile Phe Ser Ile Ala Arg Tyr Glu Ala Val Ile Asp Ala Tyr Ile
            260                 265                 270

Asp Gly Leu Glu Ala Ser Gly Leu Ser Asp Leu Ser Arg Val Thr Ser

```
            275                 280                 285
Val Ala Ser Phe Phe Val Ser Arg Val Asp Thr Leu Ile Asp Lys Met
            290                 295                 300

Leu Glu Lys Ile Gly Thr Pro Glu Ala Leu Ala Leu Arg Gly Lys Ala
305                 310                 315                 320

Ala Val Ala Gln Ala Lys Leu Ala Asn Gln Leu Tyr Gln Lys Lys Phe
                325                 330                 335

Ser Gly Pro Arg Trp Glu Ala Leu Val Lys Lys Gly Ala Lys Lys Gln
            340                 345                 350

Arg Leu Leu Trp Ala Ser Thr Ser Val Lys Asn Pro Ala Tyr Pro Asp
        355                 360                 365

Thr Leu Tyr Val Asp Pro Leu Ile Gly Pro Asp Thr Val Ser Thr Met
    370                 375                 380

Pro Asp Gln Ala Leu Leu Ala Phe Ile Asp His Gly Thr Val Ser Arg
385                 390                 395                 400

Thr Ile Asp Ala Asn Val Ser Asp Ala Glu Gly Val Tyr Ser Ala Leu
                405                 410                 415

Glu Lys Leu Gly Ile Asp Trp Asp Glu Val Gly Lys Gln Leu Glu Leu
            420                 425                 430

Glu Gly Val Asp Ser Phe Lys Lys Ala Phe Asp Ser Leu Leu Gly Ser
        435                 440                 445

Leu Glu Glu Lys Gly Asn Ser Leu Lys Lys Thr Val Ser Leu
    450                 455                 460

<210> SEQ ID NO 13
<211> LENGTH: 477
<212> TYPE: DNA
<213> ORGANISM: Zea Mays

<400> SEQUENCE: 13
atgaccggca cggtgtccaa gctggcgggc gccccggcct gcggcgccac cgctccggcc    60
ggcgtccctc cgcgccgccg caatcgcctt cgccccctcc ccgcgccggg tgggaggcgt   120
tggccaagaa aggtgccaag aaacagaggt tgttgtgggc atccaccggg tgtcaagaac   180
ccagcttatc ccgacactct ttacatcgac agtctcattg acctgacac ggtcaacacg    240 atgcccgacc aagcttttgca cgcattcata gaccacggca ctgtctcgag acagttgat   300 gcgaatgtgt ccgaggcgga aggtgtatac agcgccttgg agaagcttgg cattgactgg   360
ggcgaggtcg gaaagcagct tgagctggaa ggtgtggact ccttcaagaa gagctttgac   420
agcctactcg tgagcctaca ggagaagggc aacagcctca agacggcaac tgtgtaa     477

<210> SEQ ID NO 14
<211> LENGTH: 158
<212> TYPE: PRT
<213> ORGANISM: Zea Mays

<400> SEQUENCE: 14

Met Thr Gly Thr Val Ser Lys Leu Ala Gly Ala Pro Ala Cys Gly Ala
1               5                   10                  15

Thr Ala Pro Ala Gly Val Pro Pro Arg Arg Arg Asn Arg Leu Arg Pro
            20                  25                  30

Leu Pro Ala Pro Gly Gly Arg Arg Trp Pro Arg Lys Val Pro Arg Asn
        35                  40                  45

Arg Gly Cys Cys Gly His Pro Pro Gly Val Lys Asn Pro Ala Tyr Pro
    50                  55                  60
```

Asp Thr Leu Tyr Ile Asp Ser Leu Ile Gly Pro Asp Thr Val Asn Thr
65                  70                  75                  80

Met Pro Asp Gln Ala Leu His Ala Phe Ile Asp His Gly Thr Val Ser
                85                  90                  95

Arg Thr Val Asp Ala Asn Val Ser Glu Ala Glu Gly Val Tyr Ser Ala
            100                 105                 110

Leu Glu Lys Leu Gly Ile Asp Trp Gly Glu Val Gly Lys Gln Leu Glu
        115                 120                 125

Leu Glu Gly Val Asp Ser Phe Lys Lys Ser Phe Asp Ser Leu Leu Val
    130                 135                 140

Ser Leu Gln Glu Lys Gly Asn Ser Leu Lys Thr Ala Thr Val
145                 150                 155

<210> SEQ ID NO 15
<211> LENGTH: 1290
<212> TYPE: DNA
<213> ORGANISM: Zea Mays

<400> SEQUENCE: 15
atgaccggca cggtgtctaa gctggcggcg ccccgtccgg cggcaccgcc gctccggccg      60
gcgtccctcc gcaccgccgc cctcgccttc gcccctccg cgcgccgggt ccgcgtctcc     120
gtcgccgggc gagccaggag ccccatcatt gcgatggctt cggccaagga aggaaatggt     180
gcaccgacca gaggactgc gcttcatgat ctctacgagc tccagggcct gtccccgtgg     240
tacgacaacc tatgccgccc tgtcacagac ttgctgccca ttatcgccag cggcgtccgt     300
ggagtcacca gcaacccaac gattttccaa aaggccattt catcgtccag cgcatatgat     360
gatcagttca gcagctcat ttcggctgga aggacgcgg agagcgctta ctgggaactc     420
gttataaagg atatccaaga tgcgtgcaaa cttttttgagc ccatctacga tgagactgat     480
ggggctgatg ggtatgtctc cgtagaggtg tctcctaggt tggcaaatga cactcaagga     540
actgttgaag cggcaaagtg gttacacaaa gtggtcaacc gccccaatgt ctacataaag     600
atcccagcta ctgcagaatg tgttccttcc atccaggaag ttatcgctaa tggcattagc     660
gtcaacgtca cgcttatttt ctcaattgca agatatgagg ctgtgattga tgcttacctc     720
gatgggctag aggcttctgg cttgagtgac ttatcccgag ttactagcgt tgcatccttc     780
tttgtcagcc gagtggacac ccttattgac aaaatgcttg acaagattgg aacacctgag     840
gcccttgcct tgagaggaaa ggctgcagta gcacaggcca actagcaaa tcggctctac     900 cagaagaaat tctctggccc aaggtgggag gcgttggcca agaaaggtgc caagaaacaa     960
aggttgttgt gggcatccac cggtgtcaag aacccagctt atcctgacac tctttatgtg    1020
gacagtctca tcggacctga cacggtcaac acgatgcccg accaagcttt gcaagcattc    1080
atagaccacg gcaccgtttc aaggacagtt gatgcgaacg tgtctgaggc ggaaggtgta    1140
tacagtgcct tggagaagct tggcatcgac tgggaagagg ttggaaagca gcttgagctg    1200
gaaggcgtgg actccttcaa gaagagcttt gacagcctac tcgtgagcct gcaggagaag    1260
ggcaacagcc tcaagatggc gagtgtgtaa                                      1290

<210> SEQ ID NO 16
<211> LENGTH: 429
<212> TYPE: PRT
<213> ORGANISM: Zea Mays

<400> SEQUENCE: 16

Met Thr Gly Thr Val Ser Lys Leu Ala Ala Pro Arg Pro Ala Ala Pro

-continued

```
1               5                   10                  15
Pro Leu Arg Pro Ala Ser Leu Arg Thr Ala Ala Leu Ala Phe Ala Pro
                20                  25                  30
Ser Ala Arg Arg Val Arg Val Ser Val Ala Gly Arg Ala Arg Ser Pro
                35                  40                  45
Ile Ile Ala Met Ala Ser Ala Lys Glu Gly Asn Gly Ala Pro Thr Lys
            50                  55                  60
Arg Thr Ala Leu His Asp Leu Tyr Glu Leu Gln Gly Leu Ser Pro Trp
 65                 70                  75                  80
Tyr Asp Asn Leu Cys Arg Pro Val Thr Asp Leu Leu Pro Ile Ile Ala
                    85                  90                  95
Ser Gly Val Arg Gly Val Thr Ser Asn Pro Thr Ile Phe Gln Lys Ala
                100                 105                 110
Ile Ser Ser Ser Ala Tyr Asp Asp Gln Phe Lys Gln Leu Ile Ser
                115                 120                 125
Ala Gly Lys Asp Ala Glu Ser Ala Tyr Trp Glu Leu Val Ile Lys Asp
                130                 135                 140
Ile Gln Asp Ala Cys Lys Leu Phe Glu Pro Ile Tyr Asp Glu Thr Asp
145                 150                 155                 160
Gly Ala Asp Gly Tyr Val Ser Val Glu Val Ser Pro Arg Leu Ala Asn
                    165                 170                 175
Asp Thr Gln Gly Thr Val Glu Ala Ala Lys Trp Leu His Lys Val Val
                180                 185                 190
Asn Arg Pro Asn Val Tyr Ile Lys Ile Pro Ala Thr Ala Glu Cys Val
                195                 200                 205
Pro Ser Ile Gln Glu Val Ile Ala Asn Gly Ile Ser Val Asn Val Thr
210                 215                 220
Leu Ile Phe Ser Ile Ala Arg Tyr Glu Ala Val Ile Asp Ala Tyr Leu
225                 230                 235                 240
Asp Gly Leu Glu Ala Ser Gly Leu Ser Asp Leu Ser Arg Val Thr Ser
                    245                 250                 255
Val Ala Ser Phe Phe Val Ser Arg Val Asp Thr Leu Ile Asp Lys Met
                260                 265                 270
Leu Asp Lys Ile Gly Thr Pro Glu Ala Leu Ala Leu Arg Gly Lys Ala
            275                 280                 285
Ala Val Ala Gln Ala Lys Leu Ala Asn Arg Leu Tyr Gln Lys Lys Phe
            290                 295                 300
Ser Gly Pro Arg Trp Glu Ala Leu Ala Lys Lys Gly Ala Lys Lys Gln
305                 310                 315                 320
Arg Leu Leu Trp Ala Ser Thr Gly Val Lys Asn Pro Ala Tyr Pro Asp
                    325                 330                 335
Thr Leu Tyr Val Asp Ser Leu Ile Gly Pro Asp Thr Val Asn Thr Met
                340                 345                 350
Pro Asp Gln Ala Leu Gln Ala Phe Ile Asp His Gly Thr Val Ser Arg
                355                 360                 365
Thr Val Asp Ala Asn Val Ser Glu Ala Glu Gly Val Tyr Ser Ala Leu
                370                 375                 380
Glu Lys Leu Gly Ile Asp Trp Glu Glu Val Gly Lys Gln Leu Glu Leu
385                 390                 395                 400
Glu Gly Val Asp Ser Phe Lys Lys Ser Phe Asp Ser Leu Leu Val Ser
                    405                 410                 415
Leu Gln Glu Lys Gly Asn Ser Leu Lys Met Ala Ser Val
                420                 425
```

<210> SEQ ID NO 17
<211> LENGTH: 1200
<212> TYPE: DNA
<213> ORGANISM: Populus trichocarpa

<400> SEQUENCE: 17

```
atgtcactct ccttgcaatc tccgctctct tctgctctat cctccaaatc ctccttcctc      60
cagaaaggag gaggaggagg gagactgagg ttactcagtg gatcaccatc ttcaaatgct     120
attttttca  agctccataa cccttcattt cctcaaattc gtgcttcttc tcttgatgct     180
ggtgctagca ctgaattgga tgctgtgtct agcttgagtg agatcgtgcc tgatactgtc     240
gttttcgatg atttccagaa gtttcctcca actgctgcca ctgttagctc ttcacttctt     300
ttgggtatct gtagcctgcc cgatacaata ttcagaagtg ctgtggacac cgcattggca     360
gattcagggt gttcttctct tgaaaacgat gtgctgagat tgtcttgttt cgctaacaag     420
gctttggtga atgttggagg tgatttatct aaattggtac ccggccgagt ttcaactgaa     480
gtggatgcgc ggttggctta tgacacccat ggcattatta gaaggtgtgca tgacttgttg     540
aagtcatacg gtgaaattga tgttcctcct gagcgattgt tattcaaaat tccagcaact     600
tggcaaggaa tagaagcctc gagattgttg gagtctgagg gcatacagac gcatttgact     660
tttgtttaca gctttgttca agccgccgcc gccgctcaag ctggtgcttc tgttattcag     720
attttttgtgg acgccttag ggattggtcg cggaaccatt ctggtgaccc tgagattgaa     780
gctgctctga aaagaggaga ggatcctggg ttggcactgg tgacaaaggc ttacaattac     840
atccacaaat atgggtataa atcgaagttg atggctgctg cagttcgcaa caaacaagat     900
ttattcagtc tcttgggggt tgactatatc attgcaccat tgaaagtaat gcaatctctg     960
aaagagtctt taaccactcc tgatgagaag tactcttttg ttcggaggtt atcaccacat    1020
tctgctgctg cttacagttt cagtgaagaa gagcttatta atgggatca attaagcctt    1080
gcatcagcaa tggggcctgc atctgtggag cttctggctg ctggattgga tggttatgtt    1140
aatcaagcaa agcgagttga ggagttattt gccaagattt ggcctccccc aaatgtataa    1200
```

<210> SEQ ID NO 18
<211> LENGTH: 399
<212> TYPE: PRT
<213> ORGANISM: Populus trichocarpa

<400> SEQUENCE: 18

```
Met Ser Leu Ser Leu Gln Ser Pro Leu Ser Ala Leu Ser Ser Lys
1               5                   10                  15

Ser Ser Phe Leu Gln Lys Gly Gly Gly Gly Arg Leu Arg Leu Leu
            20                  25                  30

Ser Gly Ser Pro Ser Ser Asn Ala Ile Phe Phe Lys Leu His Asn Pro
        35                  40                  45

Ser Phe Pro Gln Ile Arg Ala Ser Ser Leu Asp Ala Gly Ala Ser Thr
    50                  55                  60

Glu Leu Asp Ala Val Ser Ser Leu Ser Glu Ile Val Pro Asp Thr Val
65                  70                  75                  80

Val Phe Asp Asp Phe Gln Lys Phe Pro Pro Thr Ala Ala Thr Val Ser
                85                  90                  95

Ser Ser Leu Leu Leu Gly Ile Cys Ser Leu Pro Asp Thr Ile Phe Arg
            100                 105                 110

Ser Ala Val Asp Thr Ala Leu Ala Asp Ser Gly Cys Ser Ser Leu Glu
```

|  |  |  |  | 115 |  |  |  | 120 |  |  |  | 125 |  |  |
|--|--|--|--|--|--|--|--|--|--|--|--|--|--|--|

Asn Asp Val Leu Arg Leu Ser Cys Phe Ala Asn Lys Ala Leu Val Asn
 130                 135                 140

Val Gly Gly Asp Leu Ser Lys Leu Val Pro Gly Arg Val Ser Thr Glu
145                 150                 155                 160

Val Asp Ala Arg Leu Ala Tyr Asp Thr His Gly Ile Ile Arg Lys Val
                165                 170                 175

His Asp Leu Leu Lys Ser Tyr Gly Glu Ile Asp Val Pro Pro Glu Arg
            180                 185                 190

Leu Leu Phe Lys Ile Pro Ala Thr Trp Gln Gly Ile Glu Ala Ser Arg
        195                 200                 205

Leu Leu Glu Ser Glu Gly Ile Gln Thr His Leu Thr Phe Val Tyr Ser
    210                 215                 220

Phe Val Gln Ala Ala Ala Ala Gln Ala Gly Ala Ser Val Ile Gln
225                 230                 235                 240

Ile Phe Val Gly Arg Leu Arg Asp Trp Ser Arg Asn His Ser Gly Asp
                245                 250                 255

Pro Glu Ile Glu Ala Ala Leu Lys Arg Gly Glu Asp Pro Gly Leu Ala
            260                 265                 270

Leu Val Thr Lys Ala Tyr Asn Tyr Ile His Lys Tyr Gly Tyr Lys Ser
        275                 280                 285

Lys Leu Met Ala Ala Ala Val Arg Asn Lys Gln Asp Leu Phe Ser Leu
    290                 295                 300

Leu Gly Val Asp Tyr Ile Ile Ala Pro Leu Lys Val Met Gln Ser Leu
305                 310                 315                 320

Lys Glu Ser Leu Thr Thr Pro Asp Glu Lys Tyr Ser Phe Val Arg Arg
                325                 330                 335

Leu Ser Pro His Ser Ala Ala Tyr Ser Phe Ser Glu Glu Glu Leu
            340                 345                 350

Ile Lys Trp Asp Gln Leu Ser Leu Ala Ser Ala Met Gly Pro Ala Ser
        355                 360                 365

Val Glu Leu Leu Ala Ala Gly Leu Asp Gly Tyr Val Asn Gln Ala Lys
    370                 375                 380

Arg Val Glu Glu Leu Phe Ala Lys Ile Trp Pro Pro Asn Val
385                 390                 395

```
<210> SEQ ID NO 19
<211> LENGTH: 318
<212> TYPE: DNA
<213> ORGANISM: Populus trichocarpa

<400> SEQUENCE: 19
atgaccgaaa gagtggactt gactttggc gggttaggga tgggggttgc tactgcccca      60
tctcctccca tgtgttccag acatttgct tggataaaag aagaagaaga agaagaaaga     120
agcaattttc tccgtctcaa tgagccgtct atagctgtta ctactagctg ctcttcccta    180
tctgcccagc ttattaaatg ggatcaatta tgccttgccc aagcaatggg gcctgcatct    240
gtggaggttc tggctgctgg atcggatgat tatgttaatc aagcaaagcg agctgaggag    300
ccttgcccaa atgtatag                                                  318

<210> SEQ ID NO 20
<211> LENGTH: 105
<212> TYPE: PRT
<213> ORGANISM: Populus trichocarpa
```

<400> SEQUENCE: 20

Met Thr Glu Arg Val Asp Leu Thr Phe Gly Gly Leu Gly Met Gly Val
1               5                   10                  15

Ala Thr Ala Pro Ser Pro Met Cys Ser Arg His Phe Ala Trp Ile
            20                  25                  30

Lys Glu Glu Glu Glu Arg Ser Asn Phe Leu Arg Leu Asn Glu
        35                  40                  45

Pro Ser Ile Ala Val Thr Thr Ser Cys Ser Ser Leu Ser Ala Gln Leu
    50                  55                  60

Ile Lys Trp Asp Gln Leu Cys Leu Ala Gln Ala Met Gly Pro Ala Ser
65              70                  75                  80

Val Glu Val Leu Ala Ala Gly Ser Asp Asp Tyr Val Asn Gln Ala Lys
            85                  90                  95

Arg Ala Glu Glu Pro Cys Pro Asn Val
            100                 105

<210> SEQ ID NO 21
<211> LENGTH: 1141
<212> TYPE: DNA
<213> ORGANISM: Oryza sativa ssp. indica

<400> SEQUENCE: 21
agtcggcagg tggagctcgt cggcggcgat gtcggccagg cctgtggcct ttagcctccg      60
gaggccggtt cttgcggccc gtgtagccgc cggcggcaac gcaccgtctt cctccgtgga    120
cgaggtggtc actgagctcg atgccgtggc cagcttcagc gagatcgtgc cggataccgt    180
cgtgttcgat gacttcgaga gtttgcgcc gaccgccgcc acggtgagct cgtcgctgct    240
gctcggtatc gctggcctcc cggatacaaa gttcaagagt gctatagata cagcattggc    300
agacggtgaa tgtaacacaa tggagaagcc cgaggaccgg atgtcctgtt cctaaccaa    360
ggccctggca atgttggag ctgaaatggc tcatctagtc cctggtcggg gtcgactga    420
aatagatgct cggttggctt atgatacca aggaattatc cagagggtgc atgagctttt    480
gaagctatac agtgatcatg atgtcttatc tgaacgcctg ctgttcaaaa ttccggctac    540
atggcaaggt atagaggcct cgaggttgct taatctgaa gggattcaaa cacatttaac    600
atttgtgtac agttttgccc aagcagcagc tgcagcacaa gccggtgcat ctgttgtaca    660
gatctttgtg ggacgtgttc gggattgggc aaggactcac tctggcgacc agagattga    720
tgaagctttg aagaaggag aagatgctgg gcttgctttg gtgaagaaag tgtatgccta    780
cattcacaaa aatgggtata aacaaagtt gatggctgct gccatacgca acaagcaaga    840
tgtgtttagc ctcctgggga ttgactacat cattgcacct ctgaagatat gcagtctttt    900
ggaagaatct gtcactgata ctgacgtgaa gtatggttat gtcccaaggc tgactcctgc    960
tcttggcaag acgtacaact tcactgaaga ggagcttgtg aagtgggacc aattgagtct   1020
agcagctgca atgggccag ctgcggaaga actacttgct tctgggttgg aaggatatgt   1080
gaaccaagca cgccgagtgg aggaactctt cgggaagatc tggcctcctc cgaatgtttg   1140
a                                                                   1141

<210> SEQ ID NO 22
<211> LENGTH: 399
<212> TYPE: PRT
<213> ORGANISM: Oryza sativa ssp. indica

<400> SEQUENCE: 22

```
Met Ala Leu Ser Ile Ser Thr Pro Pro Thr Ser Ser Leu Leu Pro
1               5                   10                  15

Ala Ser Leu Gln Val Gly Arg Trp Ser Ser Ala Ala Met Ser Ala
            20                  25                  30

Arg Pro Val Ala Phe Ser Leu Arg Arg Pro Val Leu Ala Ala Arg Val
            35                  40                  45

Ala Ala Gly Gly Asn Ala Pro Ser Ser Val Asp Glu Val Val Thr
        50                  55                  60

Glu Leu Asp Ala Val Ala Ser Phe Ser Glu Ile Val Pro Asp Thr Val
65                      70                  75                  80

Val Phe Asp Asp Phe Glu Lys Phe Ala Pro Thr Ala Ala Thr Val Ser
                85                  90                  95

Ser Ser Leu Leu Leu Gly Ile Ala Gly Leu Pro Asp Thr Lys Phe Lys
            100                 105                 110

Ser Ala Ile Asp Thr Ala Leu Ala Asp Gly Glu Cys Asn Thr Met Glu
            115                 120                 125

Lys Pro Glu Asp Arg Met Ser Cys Phe Leu Thr Lys Ala Leu Ala Asn
        130                 135                 140

Val Gly Ala Glu Met Ala His Leu Val Pro Gly Arg Val Ser Thr Glu
145                 150                 155                 160

Ile Asp Ala Arg Leu Ala Tyr Asp Thr Gln Gly Ile Ile Gln Arg Val
                165                 170                 175

His Glu Leu Leu Lys Leu Tyr Ser Asp His Asp Val Leu Ser Glu Arg
            180                 185                 190

Leu Leu Phe Lys Ile Pro Ala Thr Trp Gln Gly Ile Glu Ala Ser Arg
        195                 200                 205

Leu Leu Glu Ser Glu Gly Ile Gln Thr His Leu Thr Phe Val Tyr Ser
210                 215                 220

Phe Ala Gln Ala Ala Ala Ala Gln Ala Gly Ala Ser Val Val Gln
225                 230                 235                 240

Ile Phe Val Gly Arg Val Arg Asp Trp Ala Arg Thr His Ser Gly Asp
                245                 250                 255

Pro Glu Ile Asp Glu Ala Leu Lys Lys Gly Glu Asp Ala Gly Leu Ala
        260                 265                 270

Leu Val Lys Lys Val Tyr Ala Tyr Ile His Lys Asn Gly Tyr Lys Thr
        275                 280                 285

Lys Leu Met Ala Ala Ala Ile Arg Asn Lys Gln Asp Val Phe Ser Leu
        290                 295                 300

Leu Gly Ile Asp Tyr Ile Ile Ala Pro Leu Lys Ile Leu Gln Ser Leu
305                 310                 315                 320

Glu Glu Ser Val Thr Asp Thr Asp Val Lys Tyr Gly Tyr Val Pro Arg
                325                 330                 335

Leu Thr Pro Ala Leu Gly Lys Thr Tyr Asn Phe Thr Glu Glu Glu Leu
            340                 345                 350

Val Lys Trp Asp Gln Leu Ser Leu Ala Ala Ala Met Gly Pro Ala Ala
        355                 360                 365

Glu Glu Leu Leu Ala Ser Gly Leu Gly Tyr Val Asn Gln Ala Arg
370                 375                 380

Arg Val Glu Glu Leu Phe Gly Lys Ile Trp Pro Pro Asn Val
385                 390                 395
```

<210> SEQ ID NO 23
<211> LENGTH: 801
<212> TYPE: DNA

<213> ORGANISM: Zea Mays

<400> SEQUENCE: 23

```
atgtcctgtt acctcaccaa ggctcttgca aatgttggcg ctgaactggc tcatcaagtc    60
cctgggagag tttcgacgga aatagatgct cggttagctt atgacaccca gggcataatc   120
cacagggtac atgaactgtt gaatctatac aaccaacatg atgtctcaac tgaccgcctg   180
ttattcaaaa ttcctgctac atggcaaggc atagaggcct caaggttgct tgaatctgaa   240
ggaattcaaa cgcatctaac atttgtttac agtttcgcac aagcggcagc ggcagcacaa   300
gctggtgcat ctgtagtaca aatgtttgtg ggccgattgc gggactgggc aaggcatcac   360
tctggtgacc cagagataga tgaagctttg aagaatggag aagatgctgg gctttctttg   420
gcgaagaaag tatatgccta tattcacagg aatgggtaca aaacaaagct gatggccgct   480
gccatacgga acaagcagga cgtatttagc cttctgggga tcgattacat cattgcacca   540
ctgaagatat tgcagtctct ggaagaatct gtcaccgatc ccgatgtgaa gtacggctat   600
gtcccgaagt tgactcctgc tattggcaag acgtacaact tcactgaaga ggagcttgtg   660
aagtgggacc agctgagcct gtcagctgcc atgggaccag ctgcagaaga actgcttgct   720
tcagggctag aggggtacgt gaaccaagca cgccgcgttg aggagctctt tgggaagatc   780
tggccaccct ccaatgttta a                                              801
```

<210> SEQ ID NO 24
<211> LENGTH: 266
<212> TYPE: PRT
<213> ORGANISM: Zea Mays

<400> SEQUENCE: 24

```
Met Ser Cys Tyr Leu Thr Lys Ala Leu Ala Asn Val Gly Ala Glu Leu
1               5                   10                  15

Ala His Gln Val Pro Gly Arg Val Ser Thr Glu Ile Asp Ala Arg Leu
            20                  25                  30

Ala Tyr Asp Thr Gln Gly Ile Ile His Arg Val His Glu Leu Leu Asn
        35                  40                  45

Leu Tyr Asn Gln His Asp Val Ser Thr Asp Arg Leu Leu Phe Lys Ile
    50                  55                  60

Pro Ala Thr Trp Gln Gly Ile Glu Ala Ser Arg Leu Leu Glu Ser Glu
65                  70                  75                  80

Gly Ile Gln Thr His Leu Thr Phe Val Tyr Ser Phe Ala Gln Ala Ala
                85                  90                  95

Ala Ala Ala Gln Ala Gly Ala Ser Val Val Gln Met Phe Val Gly Arg
            100                 105                 110

Leu Arg Asp Trp Ala Arg His His Ser Gly Asp Pro Glu Ile Asp Glu
        115                 120                 125

Ala Leu Lys Asn Gly Glu Asp Ala Gly Leu Ser Leu Ala Lys Lys Val
    130                 135                 140

Tyr Ala Tyr Ile His Arg Asn Gly Tyr Lys Thr Lys Leu Met Ala Ala
145                 150                 155                 160

Ala Ile Arg Asn Lys Gln Asp Val Phe Ser Leu Leu Gly Ile Asp Tyr
                165                 170                 175

Ile Ile Ala Pro Leu Lys Ile Leu Gln Ser Leu Glu Glu Ser Val Thr
            180                 185                 190

Asp Pro Asp Val Lys Tyr Gly Tyr Val Pro Lys Leu Thr Pro Ala Ile
        195                 200                 205
```

Gly Lys Thr Tyr Asn Phe Thr Glu Glu Glu Leu Val Lys Trp Asp Gln
    210                 215                 220

Leu Ser Leu Ser Ala Ala Met Gly Pro Ala Ala Glu Glu Leu Leu Ala
225                 230                 235                 240

Ser Gly Leu Glu Gly Tyr Val Asn Gln Ala Arg Arg Val Glu Glu Leu
                245                 250                 255

Phe Gly Lys Ile Trp Pro Pro Pro Asn Val
            260                 265

<210> SEQ ID NO 25
<211> LENGTH: 1997
<212> TYPE: DNA
<213> ORGANISM: Arabidopsis Thaliana

<400> SEQUENCE: 25

| | | | | | |
|---|---|---|---|---|---|
| caacttttat | caaacaaaat | atattagaaa | acgcatggta | ctggctactg | gaaagaatca | 60 |
| tgacctgtaa | atttctacag | ttttcccgtt | ttatatagta | cttagaaact | ttggattttc | 120 |
| atagcgcaac | caataaacac | atggacttaa | gacacaaaaa | aagttgggtg | caatgtcatt | 180 |
| aatcaaacta | aaaaaataat | gattaaaagc | atggaattcc | gaaaacgcaa | caaaatgatt | 240 |
| ctgtgtttag | acaatgcag | aaaggcctct | taactaatct | taaataaagt | cttagttcca | 300 |
| accacataaa | cactccttag | ctccattaat | tttggtttc | ttaattacgt | ttctacacaa | 360 |
| gtacacgtac | ttacacatac | aattccacag | tctaaatgat | aaaactatgt | ggttttgac | 420 |
| gtcatcgtta | cctttctgtc | gtctcacctt | tatatagtgt | ctctaacaga | acgtaacaac | 480 |
| caaatgttta | aaaaaataaa | aacagcaccc | cttaattagg | ctcattcgtt | ttgcactaac | 540 |
| catactacaa | atcatctcga | acgatcgagc | aaagatttga | aaaataaata | aacgtataac | 600 |
| tctagagatt | tcattagct | aagaaaagtg | aaatcgattg | ttaatcctat | ttcagacggg | 660 |
| acaggaacac | tcattaccca | actctatcat | ctctcgaaca | ccaaactata | tctaccgttt | 720 |
| ggggcattat | ttcccacttt | ctttcgaaga | caatttccca | tatataacat | atacacatta | 780 |
| ttactaatat | attttataa | attttcgtca | catcccaaaa | aaaaacactc | tttgtcacat | 840 |
| caactagttt | ttttgtaacg | atcaaacctt | ttcgttaaa | aaaaaaaac | ttttgtagtg | 900 |
| taaacgttta | tttatcgatg | aaaaaagcca | catcttccgg | agggaaactt | tttaagacac | 960 |
| cctatttcga | ctttattttg | taaatacagt | gtgcatgtgc | atataaagag | agatatcatt | 1020 |
| tgtataaata | tcaagaatta | gaagagaaaa | agagagaaga | agacaatcta | ttactattac | 1080 |
| gatgtgtggg | ttgttaattt | gtttaaaggg | agcttttcta | tagagatttt | taaggtcaag | 1140 |
| ggtcatcgtt | cgatgtgggc | ttgcttccta | caatctagtt | gccttacggg | gcctactctt | 1200 |
| tttcttttga | taactacatc | accttttttt | tctccgacaa | ctatatatca | ctttttttat | 1260 |
| gttttccttt | ttttcttcac | aataattctt | tactcgttgc | aaatgtaaag | atacacaaag | 1320 |
| ttacttattt | tgtttacgat | ggttcttagt | agtttaaaga | attaatgaat | aagataaacc | 1380 |
| taaactttga | aaagactaaa | aaaaatgtat | aacaacatac | attatacgta | tttgaaatag | 1440 |
| tccaagtgat | attatgtcat | tgatattagc | acaaataatt | acgatgcctg | atattgtcac | 1500 |
| atttgatgat | tttaagttct | tgtaaaagat | aagtgtaact | aaatcactat | agtgaggccc | 1560 |
| acgttttaat | ttctaaacta | attacaatga | caataaaata | gcaaaactat | ttaaaactag | 1620 |
| acgccaaaaa | aaattgaaac | taataattgt | gaaaaaagaa | caagagaata | ataatcatta | 1680 |
| ataattgaca | agtgaaatta | atatattgct | cttggagggt | tatattttaa | ttttcaaact | 1740 |
| aaataatgaa | tacaaatgga | aaagctaatg | ataagagttg | aattttaata | attaagaaaa | 1800 |

```
acaaaaaaag gtgtacaagg agacacatgc gttttcctca tgcatcttgt ttttatacaa    1860
caatatatat atatatattg agtcattctc tgctagctct ctcatctcca actttcagta    1920
tgatatatag ttacaattaa ataaacctca catgctctat tcttgcttga tttttgagtt    1980
aatcttgaat ctctttg                                                   1997

<210> SEQ ID NO 26
<211> LENGTH: 1997
<212> TYPE: DNA
<213> ORGANISM: Arabidopsis Thaliana

<400> SEQUENCE: 26
tctacataac gatttctaat gatgtgagct cttaacttgc tccagcaaga tcatcaactt      60
tggagcacct tcaatgattt agttaacatg ttagataaat taaatattct tgtttcaata     120
tatatcaact ttagtgtaaa agccttaaca ttctcttgaa tatttaatt atttctcctt      180 atttcgattt aatgacaaat gtgaattaat ttttgtgata ttttgttcg aaattagttt      240 tcagttaata acatacatgt gagcatggga cacacatgat ttaacaaaag ggatgacga      300 aatgatatat caaatatta gtatgggaac aaattacgag gtgaaacttc acactcaact     360
caattaaaac tagaataaag aaatggaaaa agtgaaagaa tgagaggtca atgtggtta     420 atcattatgt ggtattagtt aatccatcaa ttgtgtaccc aaaagcatga ttaagcatag    480
aatttagaga acaaaacat cattattaat gttgaaacac aaagatccca tcaacagaca     540
aatgataagt acagtgcatg tagggtaaca acttttatgt acatgttata tacttatatt    600
atataataag aaaacgatta aagtgtcatt gctccagcct ctatttgtaa atcatattat     660
atcagtatgc ttaattccaa taattaagtc cataactaaa atatatacac atatatgtat    720
gttaaatggt tgaatatata catatatttt cataaacaaa tattgctaat taattcagtt    780
atttgtgtac ataatccaac tatcaccttt ttagctggaa gtggatattc caacatgtca    840
gtctgtcact cccacattca tactctctat tcttttttagc catttcaata tctacggtta   900
aatattaatg gctatatagc cttacccttc attttagttt tttttttggta ttcgcataac   960 catcgaatac tcaaacttac tatgtaagat ggtctgaata actatttccg atttaagatg   1020
aatagctaga ttgaaatata catgcactaa ttggacatgc actaaaggca gaggtgaatt   1080
aaatgatgaa atgaagatga agtgtcacac ttgtgcaaaa agcatgtccc ctgctcttct   1140
ccgcttgttt caatttcttt gactttcatc acgttttttgt cacttaaata caccaaaaaa   1200
tatagtacaa ttaaacatcg aaaatcgtcc aaaaagaaga aaaaaaatca tggaaagttc   1260
tttcgttaat gttacacaca ttatcttgat taggtgacac cagatattag aataaaaatg   1320
atagattatg aaaagaaaaa aaaaattgat gtatttttag gatacatcga aaggaatgaa   1380
cataccaaaa acatgggaaa aaatagataa ctaattaaca tggtagaatg tagatgacgt   1440
agatcatgaa acgagtgtgt gatatattaa tgaaaattat tttaatatac gtagctatat   1500
tagaaaataa tttacattta ttttcttcta aacaaatcta tactttatat ttacatacat   1560
tagtaaagac caaaacacat ggaattcaaa ttctgcaata agtaattgca agaaaacaca   1620
aagattaatc ccccactaaa cccgtttatt tacgttagta ttttttccgtt ttatacatta   1680 cacatgacat gacattacac gtcaaaagaa atatgtctta cgtcagaact tacgtatgat   1740
caaactcgat ttaaacatag aaacatctgt ttactaaatt atactaattt cataaagaca   1800
ctttaatgca tgaacttctt tgtttaaata acaatttccc ccttttgggg gctatgtctc   1860
```

```
gtcgagtcct accaccatta taaattatct catcgtttgc tttctttttt ttaagttgta    1920
accatttcca ctcgtaatca tacaacttct ctactcttct agagcaaaaa cccaaaaata    1980
tattgctatc ttcgtta                                                   1997

<210> SEQ ID NO 27
<211> LENGTH: 5684
<212> TYPE: DNA
<213> ORGANISM: Arabidopsis Thaliana

<400> SEQUENCE: 27
cgccgacgaa gagtagcaaa gcgcggtttt tgaaacaaca tcctccgcaa atgcctaaaa      60
ccctcgtcgt cgtcttttc  aattcgtgtt tggtttaaga ttgtgaaccg gtcgaatcaa     120
aattatgaat ctaaaccaga catttatcga cgcaaatcga accgaaatgt taaatgttta     180
aaatgagccc aagcgaagat aattcaatac ggcccaacta caatatatgt tcaaatattc     240
tttagttttt tctctcttaa ttctgaaaat aaacaaatgg tacaagatgt aaaaaaaaaa     300
attgtattaa gttgataaaa agataataag atagatcaca tataaaatgt cataataaaa     360
ttatataatc attctcttgt cctttgtttg ttctaatttc gtagtcatat gattaagagc     420
tataattctc attattattt aactatatga ggtgactcta aaacaaaatt aaagaaaagg     480
attataagag aatgaaggat ttatccctaa taatttagca ttaggtggga ttgggaacgt     540
tgacaatttg tggaggaaac gtattcacaa agtgcaaata tattaagcac taaaaaggca     600
tgattattta ttggtaatta tttacacttg agcttatttt taataatcaa attagttacg     660
actcttgtgc agttgtgcac gggtgatttt gatttcttc  attttttgtt tctacgttct     720
cttgtacttt aagacagaaa ctttgattgg tttgaaagtt acaaataaaa caagaacata     780
tatcaccgtt acaaaaatgc tattttatgc atgtcaataa tatgattttt gaagaaatat     840
cagtaagtta tatcatgcca acattgcatt acaaaaaaag gataatcaat acactagaat     900
aaaaggtcaa tcattcctaa tctaacatac ttgaagatct aaattttta  atataatatt     960 atgaattgct ttaataagac aaaactaaac tccgaaaaag tcttgttatc tatttacaaa    1020
tcgtacgttt tgcatacaaa tgattataat gttccctatg atttgtattt ttttttgtcg    1080
tcatatcctt ataggctcat ataaccatga atacatcttg gtggaggaat gatccccgca    1140
agtccacaat caaccaatca ttttcatga  aattaatcaa aatttacacc tcctcctctt    1200
tttcatcttc ttcttatgat tttctttccg atatatagtt ttaatattct ttgccatgcc    1260
acaaactaaa cttccaagac taatcataac caataatttc aatctaatat atagcagcaa    1320
atacaaattc tcatcaccat acatacatac atgtgtcatg tgtccaatga aatatggatt    1380
ggttgtaata tagagatagg taaattaata cacacactca cgcacgagct tcacgtgtag    1440
cccattactt tggctcccca agggaatgat aacgggtccc tcaaggccca ctcattagac    1500
cggaaagatc ggtggttcgt tggcaacggc tgacttgaca gtggctggac cacgccgggc    1560
tcacgagtcc aatcatataa tttgtagtgg gaccagcctt aacggcttca gtcacaagat    1620
gaaatttgtg ttaggatcaa accagccaaa ccggttgttc ttcaagttcg gtctgggcaa    1680
agaaaacatg tgatatgatg gttttgataa ctgtcactct ctcagttccc taagcctatc    1740
aatgtactca aaacagtcgg tttgtggaac ccatcatcca atgagatgaa tcaaacaaaa    1800
taagatgaaa ttttggttt  tgaaatttaa gaagtggcat tctcaaaact ctatctaaac    1860
gtagatgata gaaataattt aaatacgtac caccacttat gatgaaatga gacatccagc    1920
tctttctagt acgtacatac tactcacgaa aatagatgcg tgcaatatat aaatctttat    1980
```

```
agaccataat aaaataatat agaaattgca ggtataatca tagtgtttgc aagtggagaa    2040
ttggagatag aagcgtactg cttaagaacc atctttttat tttgttttca tattaatagc    2100
aatatcatag agacactgaa atcagagaaa agagaaagag actctgccgt caaagatata    2160
aaataagagg cctagcaatc tagcattagg tcataatatt ttgctatgga atctagtgat    2220
ccatatgatc actaattaat ttctctgatt ttgtttaaga agaaatttat acatacaaac    2280
aacatgaaaa caaaatctta aaattctagt tagatcgata aattttcata gaataaaaac    2340
acaactaatc tcttatagat taaagtgaat tgatgtgac cacaacaatt aatcgaatga    2400
agaaaaacac gaaaatatca agattattt tgattgaact tgcggattaa gttttgttg    2460 aataaaatgg caatgtggac catgtggtat gagtagtaca taaaatttag aaactcaaat    2520
cgggcttaaa tactcctata tgtgatttcg ttagaattga cctaaaagat tcgattatct    2580
aaagaagtaa ttaaatatta attatgtttg tctaagttat aaactggtat caccttcacc    2640
tatatatgaa aatcaaactt ccagagtagc tgcattttat tcgagagttt attatagtat    2700
ctctgtaatt ctatattaga atggtatgta atatgaacaa aattaaaaat ggaaccaaat    2760
ggagaatttg tatgtaagtt tggtgggggc aacaggaatt gaaatggggc cagcaccgaa    2820
ggcgataagg agcttttttg ccgcgatgat gttccctgtg ttattacgta accactcatc    2880
tcacgccacg ttattttatt actgtttttt taaaacaatt atttactctg tagttcactt    2940 ctttttcct ttacgatgtt gttatgggtt atccattaaa aaaaaaata tttgtaaatc    3000 gtctatttaa ggaaaataaa ataaaacact tcatatcatg ttatgtagta ccaaattaac    3060
aaagtattaa cttcaaatta attcgccaaa aagatgttat gatgtgatgc attctttaat    3120
atagattaaa ctattggtga tttgttttc tatagttaat cactagcaag aacattttc    3180 ttttatgttt acagttttta gattataaaa aaatggtgta ataagaacat gtcaaatcaa    3240
atgtatttaa tttgttaata tagatttgtg tataaacaat tggtagtttt gataattcaa    3300
tttttcagca atcatcataa taatacttta caagaaaagc taaatcatct gaaaattta    3360 tatgaatacg tacggtttaa ttcccaatct acaactttt tagttggatt tattataacc    3420
gtttttctaa aacaaaacac attaaaattt ataagtgaag atccaatggg ttcaaaccttt    3480 ttaattctca ataaatatac atagattctc gaagatatcc tatcaacttg taaaagttgt    3540
ttaatcaatc ttttgtttga tgaaatcttg ttcaactgtt gatttggtta agttttatag    3600
ctgaaatgtg tataagtgtt tctgaacctt tttaattact gctaaatcaa tttatgtctt    3660
acaaacttgc cgatgtatca tgtatgttca ttaggggtgt caaaatgagc cagctcgctc    3720
agctcagctc atgatgaact taaatctttt atgagccagc tcagctcaac tcatttatta    3780
tatgagcttc aaaatacaaa ctcggactca gatcatctag atcacgagct aaatgaggta    3840
gttcgcgagc taatgcaaat aaatgaaaaa atttaaattt tctaaaattt ttatgtaaat    3900
tatatatttt taaaaatata tttctatttt tatagattat ataatatttt atgttttgat    3960
tgttgacttt ttgtgtttat tactaatatt tatttcaga aattattatg taacttatat    4020 atttttctaaa atatatttct attatttata gaaaaatata tatatacttt gattgttagt    4080
tttttgtata tattacttca aaaaagccaa actcatgagc tagctcatgt tcattaaagc    4140
tcgctcatat aactcgtgag ctaaataaag ttcgatcact aaactcattt attaaatgat    4200
cctaaaaaat agaattcgcg ctcatgaata actgagtcga gttgagccag tcatgagct    4260 atcagctcat tttgacacca ttaatgttca tataataatc gtaatccatc atgaccaatt    4320
```

| | | |
|---|---|---|
| aggcaattaa gacatactat aacaaaacat ttttttttt ttcgtcaaac attgttttgt | 4380 | |
| taaaggtttc aaaagaaca tgcgtatcaa tttcaccaaa cgaatctaat aaatagcacg | 4440 | |
| accatcggat attatattgc tatttgacga tcaacgtacg ttcgattaaa aaaagtacgg | 4500 | |
| ggattgttta gtttaatcca agtgtagtgt tatttagact tcgagtaaca tcaacgcggg | 4560 | |
| agaagaaacg catgggatga atgtgtaaag tggttaactt tcaacaatgt ttcttaattg | 4620 | |
| ctaagatgtt taaacgagt ttacatgaat tcttgtgtta cttatcgaat tatcttttat | 4680 | |
| gagataatta gtacactacc ttattagggc tccatttctt tttctatcta ggcctaggtc | 4740 | |
| gatcagtact gtgtatgtta cacatatgat attaaaaaaa aaattgattc tataataatc | 4800 | |
| ttcataacta aaggcaagta tagtttattt gaaaacgtct cattcaatag ttggtagaga | 4860 | |
| tagttctaaa agatcacatt acttctctat cacacagagt gtagaaaagt gaaaacttat | 4920 | |
| gcaacacttc aggtagaaag agaaaagaca gtgatagctt agttataatt aaagaccccc | 4980 | |
| aaaatccaaa tagaatcttc tcttaaataa actattgaaa aaatattcac aaaaaaataa | 5040 | |
| aaagcacatt tccttttgct tgcatcacga gagcttttgt ctctctttac atttatgtgc | 5100 | |
| ctatatataa gcctagagaa tccaccatca tcggagtact cgttgtcttt catgatctca | 5160 | |
| acataaacaa gacaaaacgc ttttgtctct tgtctatcta aattaaatct acgaggaaac | 5220 | |
| gaagagaagc aacaaaattc gatattttag aagtcttgca taaataagaa gaaggtttca | 5280 | |
| agtaagtttc tttcagtaca tagagaaacc atgtatatga tttatgattg tcaagatgtt | 5340 | |
| acacagtcgt atatataatt ataagtattt cataaaagta atttatgaaa ccatgcacat | 5400 | |
| aactaacttt tgttttgat tttgtaaatt gagtagtttt tgttttatt atcattttta | 5460 | |
| tgtgtttata gttggttcag ccgagatatt atgagtaacc aaacgtaacc ttttcataa | 5520 | |
| tgaaacggat caaatatact ttaatctttt tcctacatat gcttagttac ttgaaaactt | 5580 | |
| gatttcacat tacttctatg catatctttt ctatgtaccg cgcgatgata agtatgtgt | 5640 | |
| tacaaattgc cacattgcag aaaatataaa attaaaaaga tcaa | 5684 | |

<210> SEQ ID NO 28
<211> LENGTH: 1997
<212> TYPE: DNA
<213> ORGANISM: Arabidopsis Thaliana

<400> SEQUENCE: 28

| | | |
|---|---|---|
| tgtagttctt cttcgggttt acaaatccag tccttttaa tccttgaatt gtgaatttcc | 60 | |
| aacaagccac tcacaattta taactaggtt ttattactga aaatatctta catggtataa | 120 | |
| gaatttatgg tgtgtagctg aacatagtgt tttaagaaaa tagattaatt atattcaaaa | 180 | |
| cgtaattttt ttgtcatctg attttattga taatacatgg aatcgtgtta tgaaatatta | 240 | |
| tccaatcaaa ctgaagtttt tggatatatt cggaacatcc atttgaccta attacgccac | 300 | |
| ataaaaccg ttaatctaaa ggatttgtct tgtgtgatgt aataataact aatgagcaat | 360 | |
| agacaaataa aaaaaaggtt tggcttgtgc agtaactgcc ggtaaagtgg agaagattgg | 420 | |
| aaaaacttta acaaaaaat tgcggtaaga gagagagaga gacgccgacc aaaaacaaac | 480 | |
| cgtagatgtc tatcccacgc gcaatcaaac ctttccttca tctccttctt cttcttcttc | 540 | |
| tccttcttct tatatcatca ttttgcaccc acatgtcaca cacttaccat atacatataa | 600 | |
| ttaagcatac tcgcataaac ctatatatac actctaagat ttctagctgg tccatatgca | 660 | |
| tgtgatctaa tcaaaagcca aactctcctt gtctttgcta tattaacaat catttgatcc | 720 | |
| acaccaccag agatttcaat cttcctctcc ttcttccttt tgctactctc ttttagatcg | 780 | |

```
ttcttgtgaa aatcgcttgc aaataacaag cccttcgtcc aatctttatt agctcgtaag      840
tttcacccca ttgctccttt tagggttttt ttgttttgtt gctgtactca cttcatgcac      900
gaaccagatg atgatacatc ggcgtttgtg ttttacgttt ttattattca aaaatacata      960
catattacat atagtatcgt tttgtatcgt ttcatatctt gaatagtata catgtgtgtg     1020
gtcctgttga gattgaccca caaatattag agtaaactgg ggaattgaaa tcaatcatgg     1080
tggggatttc ggaatctatg tgtgtttcta agatattatt gtttcttgga aattaattgt     1140
tgttgcacca taatataatt tatattatat agatagtcta ggaaaataac tcaagacaaa     1200
gagtgtgtaa cacactccaa cctcagtgac ttccacccgt caagcttttc ggctacatag     1260
cctttatata cgattatttt acatatagtt acagatatat acagtactgc ttgtatattt     1320
ttggtcttat aatactacct tatgtcatta tatatagtac atattataca aagtttcaat     1380
cttttcattt ataagcatcg ttcggtatgt agaaggcgaa acaaaccctt aaacctaata     1440 ttttttctg gtccaaaaac tttctctatc aagcttttgc attttttctt ttaaaatagt     1500
aacagctcct ccattgttgg gtggtcccat aaaaatacat cataaccatc atcagcaaca     1560
tataatagcg atagccttaa gcttaaagat ccaagctttt ggatataata tctagttaca     1620
tgtatatata tatatatgtg tttgtatatt tataggtata tagtatatta tcgtgtgcgt     1680
ccgtgtgtaa catcactatc attacccaac atacagcttt tggaatttca ttggacccaa     1740
gagccattcg atccctttct tataattaaa tataacgaag cttgtaatag gctttggttt     1800
tggtcccaaa tacaaaactt taaggttgtg ccttgtttgt ctaaggtttt cgcaatagct     1860 tccaaaaga cacgcttatg tttatataca tttcattttc cttcatatca ttctcttctc     1920
tgccacttct ccatcttgtt tcttactcat ttctctaaca attttccaaa ttaaatacgt     1980
ttataggatc atcgtgg                                                   1997
```

MEANS AND METHODS FOR ALTERING THE LIGNIN PATHWAY IN PLANTS

CROSS-REFERENCE TO RELATED APPLICATIONS

This application is a national phase entry under 35 U.S.C. § 371 of International Patent Application PCT/EP2013/066984, filed Aug. 14, 2013, designating the United States of America and published in English as International Patent Publication WO 2014/027021 A1 on Feb. 20, 2014, which claims the benefit under Article 8 of the Patent Cooperation Treaty and under 35 U.S.C. § 119(e) to U.S. Provisional Patent Application Ser. No. 61/684,019, filed Aug. 16, 2012.

TECHNICAL FIELD

This disclosure generally relates to the field of molecular biology, specifically the field of agricultural biology. In particular, the disclosure relates to means and methods for modifying the lignin pathway in plants. Accordingly, the disclosure provides chimeric genes and combinations thereof, which can be used in the context of the disclosure.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Lignin is an aromatic polymer that is deposited in secondary-thickened cells where it provides strength and impermeability to the wall. In dicot plants, lignin is mainly composed of the monolignols coniferyl and sinapyl alcohol that give rise to the guaiacyl (G) and syringyl (S)-units of the lignin polymer, respectively. In addition, a number of other units may be incorporated at lower levels, depending on the species, the genetic background and environmental conditions (Ralph et al., 2004). The lignin biosynthetic pathway is generally divided in two parts: the general phenylpropanoid pathway from phenylalanine to feruloyl-CoA, and the monolignol-specific pathway from feruloyl-CoA to the monolignols (FIG. 1). Ten enzymes are involved in the pathway from phenylalanine to the monolignols:phenylalanine ammonia-lyase (PAL), cinnamate 4-hydroxylase (C4H), 4-coumarate:CoA ligase (4CL), hydroxycinnamoyl-CoA shikimate/quinate hydroxycinnamoyl transferase (HCT), p-coumarate 3-hydroxylase (C3H), caffeoyl-CoA O-methyltransferase (CCoAOMT), cinnamoyl-CoA reductase (CCR), ferulate 5-hydroxylase (F5H), caffeic acid O-methyltransferase (COMT) and cinnamyl alcohol dehydrogenase (CAD) (FIG. 1) (Boerjan et al., 2003; Bonawitz and Chapple, 2010). After their biosynthesis, the monolignols are translocated to the cell wall where they are oxidized to radicals, which are further coupled in a combinatorial fashion with the formation of various types of chemical bonds where the ether (8-O-4), resinol (8-8) and coumaran (8-5) bonds are the most prominent ones (Ralph et al., 2004). The possibility of obtaining plants with an altered amount or structure of lignin by mutant screening (Vermerris et al., 2007) or genetic engineering (Chen and Dixon, 2007) has enabled the properties of plant biomass to be improved for forage digestibility, or processing into pulp or fermentable sugars (Pilate et al., 2002; Baucher et al., 2003; Chen and Dixon, 2007). A remarkable insight from this work is that plants with reduced lignin can either grow normally, or have dramatic effects on growth and development, depending on which gene of the lignin biosynthetic pathway that was perturbed. Apparently, plants are sometimes able to successfully cope with a mutation, a phenomenon called phenotypic buffering, while in other cases, they are not (Fu et al., 2009).

In an attempt to understand how plants cope with a genetic defect, it was previously shown that altering the expression of genes in the lignin biosynthetic pathway not only results in altered lignification, but also in shifts in both primary and secondary metabolism. For example, reductions in lignin in Arabidopsis pal1 pal2 double mutants, while not leading to abnormalities in overall plant growth, were accompanied by transcript changes of genes involved in phenylpropanoid biosynthesis, carbohydrate metabolism, stress-related pathways, signal transduction and amino acid metabolism, as studied by cDNA-AFLP (Rohde et al., 2004). Whereas all identified phenolic compounds were lower in abundance, nearly all of the detected amino acids accumulated in these mutants. Analogous experiments with CCR-down-regulated poplar showed an induced stress response and effects on cell-wall biosynthetic genes, including the induction of transcripts for PAL and reduction of hemicellulose and pectin biosynthesis. Metabolite analysis not only showed major increases in phenolic acid glucosides, but also shifts in the primary metabolites, e.g., increased levels of maleate, Kreb's cycle intermediates and several monosaccharides (Leple et al., 2007). Similar effects were observed in CCR-down-regulated tobacco where several amino acids accumulated (Dauwe et al., 2007). In CAD-down-regulated tobacco, most transcripts of genes involved in phenylpropanoid biosynthesis were lower and transcripts of light- and (non-lignin) cell wall-related genes were higher (Dauwe et al., 2007). Microarray analysis of cad-c cad-d Arabidopsis mutants revealed effects on stress-related pathways and cell wall-related proteins, including lignin, pectin, cellulose and cell wall-localized proteins (Sibout et al., 2005). Furthermore, an SSH transcript-based comparison of three brown midrib 3 (bm3) maize mutants (mutated in COMT), revealed a feedback on phenylpropanoid and hemicellulose biosynthesis and photosynthesis, and comparisons with bm1 (mutated in CAD) and bm2 (mutated gene unknown) showed a shared response in signaling and regulation (Shi et al., 2006a). So far, these types of studies have remained fragmentary and disconnected, focusing on a few individual genes in different species and the transcript and metabolite profiling methods used did not allow the extraction of genome and metabolome-wide conclusions. Hence, the major adjusting and regulatory mechanisms that may exist across the pathway to compensate for either less or modified lignin have remained largely unresolved (Vanholme et al., 2008; Vanholme et al., 2010c; Vanholme et al., 2010a). For example, it is unclear whether the flux through the phenylpropanoid pathway is redirected in a systematic way upon blocking particular steps in monolignol synthesis and to what extent feedback systems regulate the pathway. To obtain deeper insight into lignin biosynthesis and the metabolic network it is embedded in, a systems biology approach was used as defined by Ideker et al. (2001), i.e., the study of the consequences of pathway perturbations, followed by computational analysis of the data. To this end, the transcriptome and metabolome of mutants in consecutive steps of the lignin biosynthetic pathway were systematically analyzed. The spectacular advances in transcriptomics and metabolomics have opened up the possibility of fully exploiting this approach (Oksman-Caldentey and Saito, 2005; Mochida and Shinozaki, 2011), as already illustrated by studies of the consequences of altered expression of five transcription factors involved in glucosinolate biosynthesis in *Arabidopsis* (Hirai et al., 2007; Malitsky et al., 2008). *Arabidopsis* was chosen as a model because systems biology can only be properly performed in an organism for which thorough basic knowledge exists on the identity and function of genes, proteins and metabolites. Furthermore, the inflorescence stem was focused on, which is an excellent model for wood formation (Nieminen et al., 2004) as it is rich in fibers and vessels, both cell types undergoing lignification during secondary thickening. The set of *Arabidopsis* lines studied were mutated in PAL1 and 2, C4H, 4CL1 and 2, CCoAOMT1, CCR1, F5H1, COMT and CAD6, genes predicted to be involved in developmental lignification (Boerjan et al., 2003; Costa et al., 2003; Goujon et al., 2003a; Raes et al., 2003; Bonawitz and Chapple, 2010). It was shown that most of the mutations provoked a strong and organized response at the transcript and metabolite levels, even when these mutants did not have any apparent visible phenotype. Mutants with reduced lignin levels up-regulated genes of the pathways that supplied monolignol precursors, whereas mutants with compositional shifts down-regulated these pathways. In addition, metabolic profiling showed that perturbations redirected the flux into novel pathways, at the same time revealing metabolic rerouting of accumulating metabolites by 4-O and 9-O hexosylation.

DISCLOSURE

By combining metabolomic and transcriptomic data in a correlation network, unexpected system-wide consequences of the perturbations were revealed. Explorations were performed as to whether analyzing these responses to pathway perturbations can be used to reveal novel genes closely associated with the studied pathway and, thus, to identify prime candidates for genetic improvement strategies.

The disclosure surprisingly shows that a down-regulation (or a loss of function) of genes identified in this way, transaldolase gene 1 or 2 (also commonly designated herein further as a transaldolase gene) is beneficial to modify the lignin amount and/or composition in plants. It is shown that plants having a down-regulation of the transaldolase 2 gene have a reduced lignin amount and altered composition. Methods and compositions for improving plant cell wall composition are provided. The activity of a transaldolase gene can be inhibited using any method known in the art including, but not limited to, the disruption of a transaldolase gene, or a decrease in the expression of the transaldolase gene through the use of co-suppression, antisense, or RNA silencing.

Constructs and expression cassettes comprising nucleotide sequences that can efficiently reduce the expression of a transaldolase are also provided herein.

In one aspect, the cell walls and vascular structures of the modified plants described herein may comprise less lignin and/or a modified lignin. One advantage associated with such plants is that material or biomass derived therefrom can be more easily deconstructed to access carbohydrate polymers and enable the release of sugars. As such, modified plants may find application in methods for accessing and/or processing carbohydrate polymers from plant matter and, for example, biofuel production, pulp and paper making and fodder digestibility.

In another aspect, biomass derived from plants modified in accordance with this disclosure may be used as feedstock for processes that require or exploit plant cell wall carbohydrates. By way of example, biomass derived from the modified plants of this disclosure may be used in biofuel production methods.

In specific aspects, biomass for use in methods involving plant carbohydrate deconstruction (for example, biofuel production) may comprise, for example, parts of crops, waste crop material and trees, all of which may be regarded as typically high in lignin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11: Panel A shows the reduced lignin amount in the comt tra2-1 double mutant as compared to the parental lines (comt and tra2-1 mutants). Panel B shows the improved saccharification in the comt tra2-1 double mutant with respect to the single mutants tra2-1 or comt.

FIG. 12: Growth and bolting characteristics of the 20 *Arabidopsis* mutants used in this study. Bolting time and growth are given relative to WT; (−), no significant difference; (**), significant in each of the experiments; (*), a tendency, but not significantly different in each of the experiments (see material and methods).

FIG. 13: Transcript levels of general phenylpropanoid and monolignol-specific biosynthetic genes in each of the mutants and in the WT developmental series. Gene names and AGI-codes were derived from the set of 34 genes described by Raes et al. (2003). Only the genes of which the transcript level was significantly different in at least one of the mutants are given. Full names of the genes are given in FIG. 1. Values are log$_2$(abundance in the sample/abundance in WT 24 cm). In case of pal1, pal2, 4cl1, 4cl2, ccoaomt1, comt and cad6, the average of the log-ratios of the two alleles was taken. For c4h and ccr1, the values of c4h-2 and ccr1-6 are given, respectively. A red background indicates a higher transcript level in comparison with WT 24 cm, and blue a lower. The color intensity reflects the strength of induction and reduction. A green background represents the transcript level of the mutant gene. Bold values are significantly different from WT 24 cm.

FIG. 14: Transcript levels of genes coding for laccases and class III peroxidases, in each of the mutants and in the WT developmental stages. Only laccases and peroxidases that were significantly different in at least one of the developmental stages, as compared to WT 24 cm, are given. Values and color-code are explained in the description of FIG. 13. The genes are ordered according their expression level in WT 8 cm.

FIG. 15: Transcript levels of genes involved in coniferin and syringin metabolism in each of the mutants and in the WT developmental stages. Values and color-code are explained in the description of FIG. 13.

FIG. 16: Transcript levels of genes involved in the sinapate ester biosynthesis in each of the mutants and in the WT developmental stages. Full names of the genes are given in FIG. 1. Values and color-code are explained in the description of FIG. 13.

FIGS. 17A and 17B: List of genes that are co-expressed with genes involved in the phenylpropanoid biosynthesis, as derived from the correlation network. Their expression over WT development is given, values and color-code are explained in the description of FIG. 13. Full names of the genes are given in FIG. 1.

DETAILED DESCRIPTION

Figure 1:
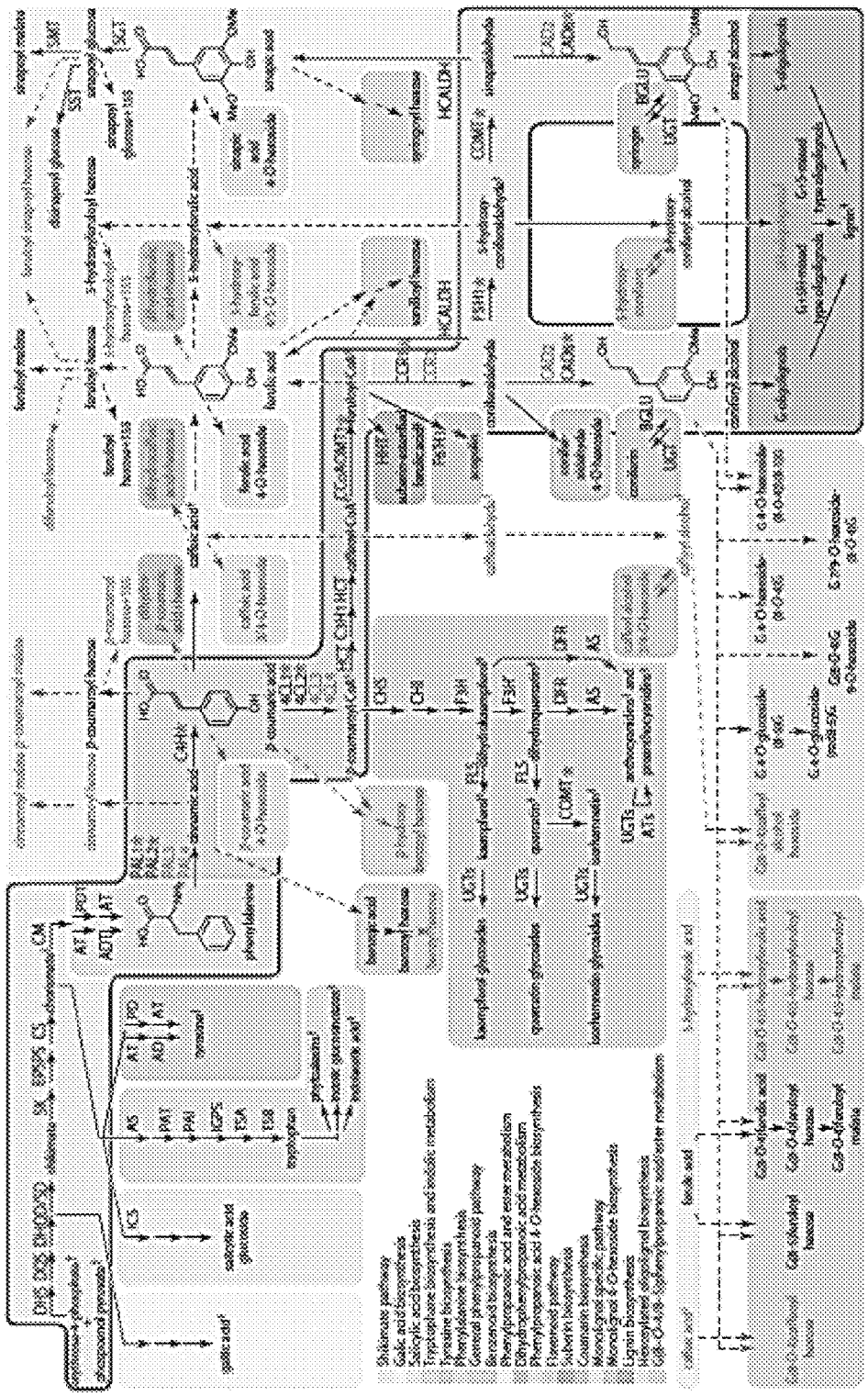
FIG. 1: Metabolic map of the phenolic metabolism in the inflorescence stem of *Arabidopsis*. The main pathways involved in lignin biosynthesis are framed with a bold black border. For enzymes with a red asterisk (*), mutants were analyzed in this study. For simplicity, proteins corresponding to individual gene family members are only given for the general phenylpropanoid pathway and monolignol-specific pathway. Family members in black were predicted to be involved in developmental lignification (Costa et al., 2003; Goujon et al., 2003a; Raes et al., 2003). Dashed arrows represent suggested pathways. The metabolites that were detectable in WT stems are given in black, whereas those that were only detectable in certain mutants are given in grey. Expression of all genes was determined via microarrays. The relative abundance of the metabolites was determined via UPLC-MS and/or GC-MS. Metabolites indicated with a cross (†) were neither detected nor identified via the used GC- and UPLC-MS techniques. This pathway representation was used to map expression and metabolite data of all studied mutant lines and WT developmental samples (FIGS. 5A-5G). DHS: 3-deoxy-D-arabino-heptulosonate 7-phosphate synthase; DQS: 3-dehydroquinate synthase; DHQD/SD: 3-dehydroquinate dehydratase/shikimate dehydrogenase; SK: shikimate kinase; EPSPS: 5-enolpyruvyl shikimate-3-phosphate synthase; CS: chorismate synthase; AT: amino transferase; AD: arogenate dehydrogenase; PD: prephenate dehydrogenase; AS: anthranilate synthase; PAT: phosphoribosylanthranilate transferase; PAI: phosphoribosylanthranilate isomerase; IGPS: indole-3-glycerol phosphate synthase; TSA: tryptophan synthase alpha subunit; TSB: tryptophan synthase beta subunit; ICS: isochorismate synthase; ADT: arogenate dehydratase; PAL: phenylalanine ammonia-lyase; C4H: cinnamate-4-hydroxylase; 4CL: 4-coumarate:CoA ligase; HCT: p-hydroxycinnamoyl-CoA: quinate shikimate p-hydroxycinnamoyltransferase; C3H: p-coumarate 3-hydroxylase; CCoAOMT: caffeoyl-CoA O-methyltransferase; CCR: cinnamoyl-CoA reductase; F5H: ferulate 5-hydroxylase; COMT: caffeic acid O-methyltransferase; CAD: cinnamyl alcohol dehydrogenase; CHS: chalcone synthase; CHI: chalcone isomerase; F3H: naringenin 3-dioxygenase; F3'H: flavonoid 3-hydroxylase; DFR: dihydroflavonol 4-reductase; AS: anthocyanidin synthase; FLS: flavonol synthase; UGT: UDP-glucosyltransferase; HCALDH: hydroxycinnamaldehyde dehydrogenase; SGT: sinapate 1-glucosyltransferase; SMT: sinapoylglucose: malate sinapoyltransferase; SST: sinapoylglucose: sinapoylglucose sinapoylglucosetransferase. For nomenclature of aromatic molecules, see Morreel et al. (2010a, b).

To facilitate the understanding of this disclosure, a number of terms are defined below. Terms defined herein (unless otherwise specified) have meanings as commonly understood by a person of ordinary skill in the areas relevant to the disclosure. As used in this specification and its appended claims, terms such as "a," "an," and "the" are not intended to refer to only a singular entity, but include the general class of which a specific example may be used for illustration, unless the context dictates otherwise. The terminology herein is used to describe specific embodiments of the disclosure, but their usage does not delimit the disclosure, except as outlined in the claims.

Lignin is predominantly deposited in the cell wall, making them rigid and impermeable and protecting the cell wall polysaccharides from microbial degradation. In wild-type plants, the presence of lignin in plant cell walls and other structures protects plant carbohydrates, rendering them inaccessible to hydrolyzing enzymes. This makes methods that require release of sugars from lignin-containing plant matter (e.g., methods for biofuel production), inefficient and costly. In the disclosure, a key gene has been identified (i.e., transaldolase), which, when its activity is down-regulated, leads to a significant reduction in lignin in plant cell walls and to an altered lignin composition.

Plant transaldolases are enzymes of the non-oxidative phase of the pentose phosphate pathway. In *Arabidopsis thaliana*, two transaldolases have been identified, the transaldolase 1 and the transaldolase 2. A preferred representative of the plant transaldolase in *Arabidopsis* is AT5G13420 (TAIR accession, available via the world wide web at *arabidopsis*.org), which is the transaldolase 2 for which the coding sequence is depicted in SEQ ID NO: 1 and its protein sequence is depicted in SEQ ID NO:2. Another preferred representative of the plant transaldolase in *Arabidopsis* is AT1G12230, which is the transaldolase 1 for which the coding sequence is depicted in SEQ ID NO:3 and its protein sequence is depicted in SEQ ID NO:4. In the present disclosure, the term "transaldolase" with respect to down-regulation (or mutation), is used to refer to either the transaldolase 2 (or an orthologue thereof) or the transaldolase 1 gene (or an orthologue thereof). Without limiting the disclosure to a particular mechanism, it is envisaged that the combined down-regulation of transaldolase 1 and transaldolase 2 will be less beneficial for modulating the lignin composition in plant or plant cells.

The enzymatic activity of the transaldolase, such as the transaldolase 1 or 2, can be measured, for example, in plant cellular extracts since the enzyme generates erythrose-4-phosphate, a precursor for the secondary metabolism.

Transaldolases, such as the transaldolase 1 or 2, catalyze the following chemical reaction:

Sedoheptulose 7-phosphate+glyceraldehyde 3-phosphate↔erythrose 4-phosphate+fructose 6-phosphate A plant having reduced transaldolase activity can have at least one of the following phenotypes including, but not limited to: a reduced lignin content, a modified lignin content, or an improved saccharification when compared to a non-modified plant under normal growth conditions. Plants having a reduced and/or modified lignin content are useful for the paper and pulp industry, for biofuel applications and for improved digestibility.

The term "saccharification" means the process of converting a complex carbohydrate, such as starch, cellulose or hemicellulose, into sugars such as fermentable sugars. It is essentially a hydrolysis. The process may, for example, be accomplished by the use of enzymes or acids or other chemicals.

Any method known in the art to reduce or eliminate the activity of a plant transaldolase polypeptide can be used to alter the lignin, in particular, reduced lignin amount or altered composition. In some embodiments, a polynucleotide is introduced into a plant that may inhibit the expression of a transaldolase polypeptide directly, by preventing transcription or translation of a transaldolase messenger RNA, or indirectly, by encoding a polypeptide that inhibits the transcription or translation of a transaldolase gene encoding a transaldolase polypeptide. Methods for inhibiting or eliminating the expression of a gene in a plant are well known in the art, and any such method may be used in the disclosure to inhibit the expression of the transaldolase polypeptide. In other embodiments, a polynucleotide that encodes a polypeptide that inhibits the activity of a transaldolase polypeptide is introduced into a plant. In yet other embodiments, the activity of a transaldolase is inhibited through disruption of a transaldolase gene. Many methods may be used to reduce or eliminate the activity of a transaldolase polypeptide. In addition, more than one method may be used to reduce the activity of a single transaldolase polypeptide. In some embodiments, the transaldolase activity is reduced through the disruption of at least one transaldolase gene or a reduction in the expression of at least one transaldolase gene. A transaldolase gene can comprise, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% or more sequence identity to SEQ ID NO: 1 or SEQ ID NO:3. Many transaldolase genes are known to those of skill in the art and are readily available through sources such as GENBANK and the like. The expression of any transaldolase gene may be reduced according to the disclosure.

In accordance with the disclosure, the expression of a transaldolase is inhibited if the transcript or protein level of the transaldolase is statistically lower than the transcript or protein level of the same transaldolase in a plant that has not been genetically modified or mutagenized to inhibit the expression of that transaldolase. In particular embodiments of the disclosure, the transcript or protein level of the transaldolase in a modified plant according to the disclosure is less than 95%, less than 90%, less than 85%, less than 80%, less than 75%, less than 70%, less than 60%, less than 50%, less than 40%, less than 30%, less than 20%, less than 10%, or less than 5% of the protein level of the same transaldolase in a plant that is not a mutant or that has not been genetically modified to inhibit the expression of that transaldolase. The expression level of the transaldolase may be measured directly, for example, by assaying for the level of transaldolase expressed in the cell or plant, or indirectly, for example, by measuring the transaldolase activity in the cell or plant. The activity of a transaldolase protein is "eliminated" according to the disclosure when it is not detectable by at least one assay method. Methods for assessing transaldolase activity are known in the art and include measuring levels of transaldolase, which can be recovered and assayed from cell extracts.

In other embodiments of the disclosure, the activity of one or more transaldolases is reduced or eliminated by transforming a plant cell with an expression cassette comprising a polynucleotide encoding a polypeptide that inhibits the activity of one or more transaldolases. The activity of a transaldolase is inhibited according to the disclosure if the activity of that transaldolase in the transformed plant or cell is statistically lower than the activity of that transaldolase in a plant that has not been genetically modified to inhibit the activity of at least one transaldolase. In particular embodiments of the disclosure, a transaldolase activity of a modified plant according to the disclosure is less than 95%, less than 90%, less than 85%, less than 80%, less than 75%, less than 70%, less than 60%, less than 50%, less than 40%, less than 30%, less than 20%, less than 10%, or less than 5% of that transaldolase activity in an appropriate control plant that has not been genetically modified to inhibit the expression or activity of the transaldolase.

In other embodiments, the activity of a transaldolase may be reduced or eliminated by disrupting at least one gene encoding the transaldolase. The disruption inhibits expression or activity of at least one transaldolase protein compared to a corresponding control plant cell lacking the disruption. In one embodiment, the at least one endogenous transaldolase gene comprises two or more endogenous transaldolase genes. Similarly, in another embodiment, the at least one endogenous transaldolase gene comprises three or more endogenous transaldolase genes. The wording "two or more endogenous transaldolase genes" or "three or more endogenous transaldolase genes" preferably refers to two or more or three or more homologs of transaldolase 1 or transaldolase 2 but it is not excluded that two or more or three or more combinations of homologs of transaldolase 1 or transaldolase 2 are disrupted (or their activity reduced). Preferentially, a residual activity of at least one active homolog of transaldolase 1 or transaldolase 2 is present in the mutant or transgenic plant. The gene disruption results in plant cell walls with a reduced lignin content as compared to a control plant in similar conditions.

In another embodiment, the disruption step comprises insertion of one or more transposons, where the one or more transposons are inserted into the at least one endogenous transaldolase gene. In yet another embodiment, the disruption comprises one or more point mutations in the at least one endogenous transaldolase gene. The disruption can be a homozygous disruption in the at least one transaldolase gene. Alternatively, the disruption is a heterozygous disruption in the at least one transaldolase gene. In certain embodiments, when more than one transaldolase gene is involved, there is more than one disruption, which can include homozygous disruptions, heterozygous disruptions or a combination of homozygous disruptions and heterozygous disruptions.

Detection of expression products is performed, either qualitatively (by detecting presence or absence of one or more product of interest) or quantitatively (by monitoring the level of expression of one or more product of interest). In one embodiment, the expression product is an RNA expression product. Aspects of the disclosure optionally include monitoring an expression level of a nucleic acid, polypeptide as noted herein for detection of transaldolase or measuring the amount or composition of lignin in a plant or in a population of plants.

Thus, many methods may be used to reduce or eliminate the activity of a transaldolase. More than one method may be used to reduce the activity of a single plant transaldolase. In addition, combinations of methods may be employed to reduce or eliminate the activity of two or more different transaldolases. Non-limiting examples of methods of reducing or eliminating the expression of a plant transaldolase are given below.

In some embodiments of the disclosure, a polynucleotide is introduced into a plant that upon introduction or expression, inhibits the expression of a transaldolase of the disclosure. The term "expression" as used herein refers to the biosynthesis of a gene product, including the transcription and/or translation of the gene product. For example, for the purposes of the disclosure, an "expression cassette capable of expressing a polynucleotide that inhibits the expression of at least one transaldolase polypeptide" is an expression cassette capable of producing an RNA molecule that inhibits the transcription and/or translation of at least one transaldolase polypeptide of the disclosure. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Further, "expression" of a gene can refer to the transcription of the gene into a non-protein coding transcript.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including, inter alia, simple and complex cells.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "encoding" or "encoded," with respect to a specified nucleic acid, is meant comprising the information for transcription into an RNA and in some embodiments, translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

Examples of polynucleotides that inhibit the expression of a transaldolase polypeptide are given below. In some embodiments of the disclosure, inhibition of the expression of a transaldolase polypeptide may be obtained by sense suppression or co-suppression. For co-suppression, an expression cassette is designed to express an RNA molecule corresponding to all or part of a messenger RNA encoding a transaldolase polypeptide in the "sense" orientation. Overexpression of the RNA molecule can result in reduced expression of the native gene. Accordingly, multiple plant lines transformed with the co-suppression expression cassette are screened to identify those that show the greatest inhibition of transaldolase polypeptide expression.

The polynucleotide used for co-suppression may correspond to all or part of the sequence encoding the transaldolase polypeptide, all or part of the 5' and/or 3' untranslated region of a transaldolase polypeptide transcript or all or part of both the coding sequence and the untranslated regions of a transcript encoding a transaldolase polypeptide. A polynucleotide used for co-suppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides (e.g., SEQ ID NO:1, 3, 7, 9, 11, 13, 15, 17, 19, 21 or 23) are used to disrupt the expression of the target gene, generally, sequences of at least 15, 19, 20, 21, 22, 23, 24, 25, 26, 27, 28, 29, 30, 35, 40, 45, 50, 60, 70, 80, 90, 100, 200, 300, 400, 450, 500, 550, 600, 650, 700, 750, 800, 900, or 1000 contiguous nucleotides or greater may be used. In some embodiments where the polynucleotide comprises all or part of the coding region for the transaldolase polypeptide, the expression cassette is designed to eliminate the start codon of the polynucleotide so that no protein product will be translated.

Co-suppression may be used to inhibit the expression of plant genes to produce plants having undetectable protein levels for the proteins encoded by these genes. See, for example, Broin, et al. (2002) *Plant Cell* 14:1417-1432. Co-suppression may also be used to inhibit the expression of multiple proteins in the same plant. See, for example, U.S. Pat. No. 5,942,657. Methods for using co-suppression to inhibit the expression of endogenous genes in plants are described in U.S. Pat. No. 5,034,323, U.S. Pat. No. 5,283,184 and U.S. Pat. No. 5,942,657, each of which is herein incorporated by reference. The efficiency of co-suppression may be increased by including a poly-dT region in the expression cassette at a position 3' to the sense sequence and 5' of the polyadenylation signal. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. No. 5,283,184 and U.S. Pat. No. 5,034,323, herein incorporated by reference.

In some embodiments of the disclosure, inhibition of the expression of the transaldolase polypeptide may be obtained by antisense suppression. For antisense suppression, the expression cassette is designed to express an RNA molecule complementary to all or part of a messenger RNA encoding the transaldolase polypeptide. Overexpression of the antisense RNA molecule can result in reduced expression of the native gene. Accordingly, multiple plant lines transformed with the antisense suppression expression cassette are screened to identify those that show the greatest inhibition of transaldolase polypeptide expression.

The polynucleotide for use in antisense suppression may correspond to all or part of the complement of the sequence encoding the transaldolase polypeptide, all or part of the complement of the 5' and/or 3' untranslated region of the transaldolase transcript or all or part of the complement of both the coding sequence and the untranslated regions of a transcript encoding the transaldolase polypeptide.

In addition, the antisense polynucleotide may be fully complementary (i.e., 100% identical to the complement of the target sequence) or partially complementary (i.e., less than 100%, including, but not limited to, 99%, 98%, 97%, 96%, 95%, 94%, 93%, 92%, 91%, 90%, 89%, 88%, 87%, 85%, 80%, identical to the complement of the target sequence, which in some embodiments is SEQ ID NO: 1, 3, 7, 9, 11, 13, 15, 17, 19, 21 or 23) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

Methods for using antisense suppression to inhibit the expression of endogenous genes in plants are described, for example, in U.S. Pat. No. 5,759,829, which is herein incorporated by reference. Efficiency of antisense suppression may be increased by including a poly-dT region in the expression cassette at a position 3' to the antisense sequence and 5' of the polyadenylation signal.

In some embodiments of the disclosure, inhibition of the expression of a transaldolase polypeptide may be obtained by double-stranded RNA (dsRNA) interference. For dsRNA interference, a sense RNA molecule like that described above for co-suppression and an antisense RNA molecule that is fully or partially complementary to the sense RNA molecule are expressed in the same cell, resulting in inhibition of the expression of the corresponding endogenous messenger RNA. Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of transaldolase polypeptide expression. Methods for using dsRNA interference to inhibit the expression of endogenous plant genes are described in WO9949029, WO9953050, WO9961631 and WO0049035, each of which is herein incorporated by reference.

In some embodiments of the disclosure, inhibition of the expression of a transaldolase polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein. For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. The antisense sequence may be located "upstream" of the sense sequence (i.e., the antisense sequence may be closer to the promoter driving expression of the hairpin RNA than the sense sequence). The base-paired stem region may correspond to a portion of a promoter sequence controlling expression of the gene to be inhibited. A polynucleotide designed to express an RNA molecule having a hairpin structure comprises a first nucleotide sequence and a second nucleotide sequence that is the complement of the first nucleotide sequence, and wherein the second nucleotide sequence is in an inverted orientation relative to the first nucleotide sequence. Thus, the base-paired stem region of the molecule generally determines the specificity of the RNA interference. The sense sequence and the antisense sequence are generally of similar lengths but may differ in length. Thus, these sequences may be portions or fragments of at least 10, 19, 20, 21, 22, 23, 24, 25, 26, 27, 28, 29, 30, 50, 70, 90, 100, 120, 140, 160, 180, 200, 220, 240, 260, 280, 300, 320, 340, 360, 380, 400, 500, 600, 700, 800, 900 nucleotides in length, or at least 1, 2, 3, 4, 5, 6, 7, 8, 9, or 10 kb in length. The loop region of the expression cassette may vary in length. Thus, the loop region may be at least 10, 20, 30, 40, 50, 75, 100, 200, 300, 400, 500, 600, 700, 800, 900 nucleotides in length, or at least 1, 2, 3, 4, 5, 6, 7, 8, 9, or 10 kb in length. hpRNA molecules are highly efficient at inhibiting the expression of endogenous genes and the RNA interference they induce is inherited by subsequent generations of plants. See, for example, Waterhouse and Helliwell, (2003) *Nat. Rev. Genet.* 4:29-38. A transient assay for the efficiency of hpRNA constructs to silence gene expression in vivo has been described by Panstruga, et al. (2003) *Mol. Biol. Rep.* 30:135-140, herein incorporated by reference. For ihpRNA, the interfering molecules have the same general structure as for hpRNA, but the RNA molecule additionally comprises an intron in the loop of the hairpin that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407:319-320. In fact, Smith et al. show 100% suppression of endogenous gene expression using ihpRNA-mediated interference. In some embodiments, the intron is the ADH1 intron 1. Methods for using ihpRNA interference to inhibit the expression of endogenous plant genes are described, for example, in Smith et al. (2000) *Nature* 407:319-320; Waterhouse and Helliwell (2003) *Nat. Rev. Genet.* 4:29-38; Helliwell and Waterhouse (2003) *Methods* 30:289-295 and US2003180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO00200904, herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the transaldolase polypeptide). Methods of using amplicons to inhibit the expression of endogenous plant genes are described, for example, in U.S. Pat. No. 6,635,805, which is herein incorporated by reference.

In some embodiments, the polynucleotide expressed by the expression cassette of the disclosure is catalytic RNA or has ribozyme activity specific for the messenger RNA of the transaldolase polypeptide. Thus, the polynucleotide causes the degradation of the endogenous messenger RNA, resulting in reduced expression of the transaldolase polypeptide. This method is described, for example, in U.S. Pat. No. 4,987,071, herein incorporated by reference. In some embodiments of the disclosure, inhibition of the expression of a transaldolase polypeptide may be obtained by RNA interference by expression of a polynucleotide encoding a micro RNA (miRNA). miRNAs are regulatory agents consisting of about 22 ribonucleotides. miRNA are highly efficient at inhibiting the expression of endogenous genes. See, for example Javier et al. (2003) *Nature* 425:257-263, herein incorporated by reference.

For miRNA interference, the expression cassette is designed to express an RNA molecule that is modeled on an endogenous pre-miRNA gene wherein the endogenous miRNA and miRNA* sequence are replaced by sequences targeting the transaldolase mRNA. The miRNA gene encodes an RNA that forms a hairpin structure containing a 22-nucleotide sequence that is complementary to another endogenous gene (target sequence). For suppression of the transaldolase, the 22-nucleotide sequence is selected from a transaldolase transcript sequence and contains 22 nucleotides of the transaldolase in sense orientation (the miRNA* sequence) and 21 nucleotides of a corresponding antisense sequence that is complementary to the sense sequence and complementary to the target mRNA (the miRNA sequence).

No perfect complementarity between the miRNA and its target is required, but some mismatches are allowed. Up to four mismatches between the miRNA and miRNA* sequence are also allowed. miRNA molecules are highly efficient at inhibiting the expression of endogenous genes, and the RNA interference they induce is inherited by subsequent generations of plants.

In some embodiments, polypeptides or polynucleotide-encoding polypeptides can be introduced into a plant, wherein the polypeptide is capable of inhibiting the activity of a transaldolase polypeptide. The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

In one embodiment, the polynucleotide encodes a zinc finger protein that binds to a gene encoding a transaldolase polypeptide, resulting in reduced expression of the gene. In particular embodiments, the zinc finger protein binds to a regulatory region of a transaldolase. In other embodiments, the zinc finger protein binds to a messenger RNA encoding a transaldolase polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US2003/0037355, each of which is herein incorporated by reference.

In another embodiment, the polynucleotide encoded a TALE protein that binds to a gene encoding a transaldolase polypeptide, resulting in reduced expression of the gene. In particular embodiments, the TALE protein binds to a regulatory region of a transaldolase. In other embodiments, the TALE protein binds to a messenger RNA encoding a transaldolase polypeptide and prevents its translation. Methods of selecting sites for targeting by zinc finger proteins have been described in, e.g., M. J. Moscou and A. J. Bogdanove (2009) (A simple cipher governs DNA recognition by TAL effectors, *Science* 326:1501) and R. Morbitzer, P. Romer, J. Boch, and T. Lahaye (2010) (Regulation of selected genome loci using de novo-engineered transcription activator-like effector (TALE)-type transcription factors, *Proc. Natl. Acad. Sci. U.S.A.* 107:21617-21622).

In some embodiments of the disclosure, the polynucleotide encodes an antibody that binds to at least one transaldolase polypeptide and reduces the activity of the transaldolase polypeptide. In another embodiment, the binding of the antibody results in increased turnover of the antibody-transaldolase complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

In some embodiments of the disclosure, the activity of a transaldolase is reduced or eliminated by disrupting the gene encoding the transaldolase polypeptide. The gene encoding the transaldolase polypeptide may be disrupted by any method known in the art. For example, in one embodiment, the gene is disrupted by transposon tagging. In another embodiment, the gene is disrupted by mutagenizing plants using random or targeted mutagenesis and screening for plants that have a reduced lignin amount or altered lignin composition in their cell walls.

In one embodiment of the disclosure, transposon tagging is used to reduce or eliminate the transaldolase activity of one or more transaldolase polypeptides. Transposon tagging comprises inserting a transposon within an endogenous transaldolase gene to reduce or eliminate expression of the transaldolase polypeptide. In this embodiment, the expression of one or more transaldolase polypeptides is reduced or eliminated by inserting a transposon within a regulatory region or coding region of the gene encoding the transaldolase polypeptide. A transposon that is within an exon, intron, 5' or 3' untranslated sequence, a promoter or any other regulatory sequence of a transaldolase gene may be used to reduce or eliminate the expression and/or activity of the encoded transaldolase polypeptide.

Methods for the transposon tagging of specific genes in plants are well known in the art. See, for example, Meissner, et al. (2000) *Plant J.* 22:265-21. In addition, the TUSC process for selecting Mu insertions in selected genes has been described in U.S. Pat. No. 5,962,764, which is herein incorporated by reference.

Additional methods for decreasing or eliminating the expression of endogenous genes in plants are also known in the art and can be similarly applied to the disclosure. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al. (1998) *Virology* 243:472-481; Okubara, et al. (1994) *Genetics* 137:867-874; and Quesada, et al. (2000) *Genetics* 154:421-436, each of which is herein incorporated by reference. In addition, a fast and automatable method for screening for chemically induced mutations, TILLING (Targeting Induced Local Lesions in Genomes), using denaturing HPLC or selective endonuclease digestion of selected PCR products is also applicable to the disclosure. See, McCallum, et al. (2000) *Nat. Biotechnol.* 18:455-457, herein incorporated by reference. Mutations that impact gene expression or that interfere with the function of the encoded protein are well known in the art. Insertional mutations in gene exons usually result in null-mutants. Mutations in conserved residues are particularly effective in inhibiting the activity of the encoded protein. Conserved residues of plant transaldolase polypeptides suitable for mutagenesis with the goal to eliminate transaldolase activity have been described. Such mutants can be isolated according to well-known procedures, and mutations in different transaldolase loci can be stacked by genetic crossing. See, for example, Gruis, et al. (2002) *Plant Cell* 14:2863-2882. In another embodiment of this disclosure, dominant mutants can be used to trigger RNA silencing due to gene inversion and recombination of a duplicated gene locus. See, for example, Kusaba, et al. (2003) *Plant Cell* 15:1455-1467.

Single-stranded DNA can also be used to down-regulate the expression of transaldolase genes. Methods for gene suppression using ssDNA are, e.g., described in WO2011/112570.

In yet another embodiment, the disclosure encompasses still additional methods for reducing or eliminating the activity of one or more transaldolase polypeptides.

Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleotide bases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. Where polynucleotides are used to decrease or inhibit transaldolase activity, it is recognized that modifications of the exemplary sequences disclosed herein may be made as long as the sequences act to decrease or inhibit expression of the corresponding mRNA. Thus, for example, polynucleotides having at least 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein (e.g., SEQ ID NOS: 1, 3, 5, 7, 9, 11, 13, 15, 17, 19, 21 and 23) may be used. Furthermore, portions or fragments of the exemplary sequences or portions or fragments of polynucleotides sharing a particular percent sequence identity to the exemplary sequences may be used to disrupt the expression of the target gene. Generally, fragments or sequences of at least 10, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more contiguous nucleotides, or greater of, for example, SEQ ID NOS:1, 3, 5, 7, 9, 11, 13, 15, 17, 19, 21, and 23 may be used. It is recognized that in particular embodiments, the complementary sequence of such sequences may be used. For example, hairpin constructs comprise both a sense sequence fragment and a complementary, or antisense, sequence fragment corresponding to the gene of interest. Antisense constructs may share less than 100% sequence identity with the gene of interest, and may comprise portions or fragments of the gene of interest, so long as the object of the embodiment is achieved, i.e., as long as expression of the gene of interest is decreased.

The transaldolase nucleic acids that may be used for the disclosure comprise at least one transaldolase polynucleotide selected from the group consisting of:
  (a) a polynucleotide encoding a transaldolase polypeptide and conservatively modified and polymorphic variants thereof; such as SEQ ID NO: 1, 3, 5, 7, 9, 11, 13, 15, 17, 19, 21 or 23;
  (b) a polynucleotide having at least 70% sequence identity with polynucleotides of (a);
  (c) a fragment of a polynucleotide encoding a transaldolase polypeptide; and
  (d) complementary sequences of polynucleotides of (a), (b), or (c).

Thus, in some embodiments, the method comprises introducing at least one polynucleotide sequence comprising a transaldolase nucleic acid sequence, or subsequence thereof, into a plant cell, such that the at least one polynucleotide sequence is linked to a plant-expressible promoter in a sense or antisense orientation, and where the at least one polynucleotide sequence comprises, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NO:1, 3, 5, 7, 9, 11, 13, 15, 17, 19, 21 or 23 or a subsequence thereof or a complement thereof. In another embodiment, the disruption is effected by introducing into the plant cell at least one polynucleotide sequence comprising one or more subsequences of a transaldolase nucleic acid sequence configured for RNA silencing or interference. In other embodiments, the methods of the disclosure are practiced with a polynucleotide comprising a member selected from the group consisting of: (a) a polynucleotide or a complement thereof, comprising, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, about 99.5% or more sequence identity to SEQ ID NOS:1, 3, 5, 7, 9, 11, 13, 15, 17, 19, 21, 23 and 25 or a subsequence thereof, or a conservative variation thereof; (b) a polynucleotide, or a complement thereof, encoding a polypeptide sequence of SEQ ID NOS:2, 4, 6, 8, 10, 12, 14, 16, 18, 20, 22 and 24 or a subsequence thereof, or a conservative variation thereof; (c) a polynucleotide, or a complement thereof, that hybridizes under stringent conditions over substantially the entire length of a polynucleotide subsequence comprising at least 100 contiguous nucleotides of SEQ ID NO:1, 3, 5, 7, 9, 11, 13, 15, 17, 19, 21 or 23 or that hybridizes to a polynucleotide sequence of (a) or (b); and (d) a polynucleotide that is at least about 85% identical to a polynucleotide sequence of (a), (b) or (c). In particular embodiments, a heterologous polynucleotide is introduced into a plant, wherein the heterologous polynucleotide is selected from the group consisting of: a) a nucleic acid comprising a transaldolase nucleic acid; b) a nucleic acid comprising at least 15 contiguous nucleotides of the complement of a transaldolase nucleic acid; and c) a nucleic acid encoding a transcript that is capable of forming a double-stranded RNA (e.g., a hairpin) and mediated RNA interference of a transaldolase nucleic acid, wherein the nucleic acid comprises a first nucleotide sequence comprising at least 20 contiguous nucleotides of a transaldolase nucleic acid, and a second nucleotide sequence comprising the complement of the first nucleotide sequence. In other particular embodiments, the methods comprise introducing into a plant a heterologous polynucleotide selected from the group consisting of: a) the nucleotide sequence set forth in SEQ ID NOS:1, 3, 5, 7, 9, 11, 13, 15, 17, 19, 21 and 23, or a complete complement thereof; b) a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO:1, 3, 5, 7, 9, 11, 13, 15, 17, 19, 21, or 23, or a complete complement thereof; c) a nucleotide sequence encoding the polypeptide sequence of SEQ ID NO:2, 4, 6, 8, 10, 12, 14, 16, 18, 20, 22 or 24; d) a nucleotide sequence encoding a polypeptide sequence having at least 70%, at least 75%, at least 80%, at least 85%, at least 90%, at least 91%, at least 92%, at least 93%, at least 94%, at least 95%, at least 96%, at least 97%, at least 98%, at least 99% or greater sequence identity to SEQ ID NO:2, 4, 6, 8, 10, 12, 14, 16, 18, 20, 22 or 24; e) a nucleotide sequence comprising at least 15 contiguous nucleotides of SEQ ID NO:1, 3, 5, 7, 9, 11, 13, 15, 17, 19, 21 or 23; f) a nucleotide sequence comprising at least 15 contiguous nucleotides of the complement of SEQ ID NO:1, 3, 5, 7, 9, 11, 13, 15, 17, 19, 21 or 23; and g) a nucleotide sequence encoding a transcript that is capable of forming a double-stranded RNA (e.g., hairpin) and mediating RNA interference of a transaldolase nucleic acid, wherein the nucleotide sequence comprises at least 20 contiguous nucleotides of SEQ ID NO:1, 3, 5, 7, 9, 11, 13, 15, 17, 19, 21 or 23, and the complement thereof. In other embodiments, the heterologous polynucleotide comprises at least 500 contiguous nucleotides of SEQ ID NO:1, 3, 5, 7, 9, 11, 13, 15, 17, 19, 21 or 23 and the complement thereof. In some of these embodiments, the heterologous polynucleotide encodes a transcript that is capable of forming a double-stranded RNA (e.g., hairpin) and mediating RNA interference of a transaldolase nucleic acid. In some of these embodiments, the plant comprises an mRNA encoded by a polynucleotide having the target sequence set forth in SEQ ID NO:1, 3, 5, 7, 9, 11, 13, 15, 17, 19, 21 or 23.

The disclosure provides methods utilizing, inter alia, isolated nucleic acids of RNA, DNA, homologs, paralogous genes and orthologous genes and/or chimeras thereof, comprising a transaldolase polynucleotide. This includes naturally occurring as well as synthetic variants and homologs of the sequences.

The terms "isolated" or "isolated nucleic acid" or "isolated protein" refer to material, such as a nucleic acid or a protein, which is substantially or essentially free from components that normally accompany or interact with it as found in its naturally occurring environment. The isolated material optionally comprises material not found with the material in its natural environment. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Sequences homologous, i.e., that share significant sequence identity or similarity, to those provided herein derived from maize, Arabidopsis thaliana or from other plants of choice, can also be used in the methods of the disclosure. Homologous sequences can be derived from any plant including monocots and dicots and, in particular, agriculturally important plant species including, but not limited to, crops such as soybean, wheat, corn (maize), potato, cotton, rice, rape, oilseed rape (including canola), sunflower, alfalfa, clover, sugarcane and turf, or fruits and vegetables, such as banana, blackberry, blueberry, strawberry and raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, tomatillo, watermelon, rosaceous fruits (such as apple, peach, pear, cherry and plum) and vegetable brassicas (such as broccoli, cabbage, cauliflower, Brussels sprouts and kohlrabi). Other crops, including fruits and vegetables, whose phenotype can be changed and that comprise homologous sequences include barley; rye; millet; sorghum; currant; avocado; citrus fruits such as oranges, lemons, grapefruit and tangerines; artichoke; cherries; nuts such as the walnut and peanut; endive; leek; roots such as arrowroot, beet, cassava, turnip, radish, yam and sweet potato and beans. The homologous sequences may also be derived from woody species, such pine, poplar and eucalyptus or mint or other labiates. Homologous sequences as described above can comprise orthologous or paralogous sequences. Several different methods are known by those of skill in the art for identifying and defining these functionally homologous sequences. Three general methods for defining orthologous and paralogous genes are described; an ortholog, paralog or homolog may be identified by one or more of the methods described below. Orthologs and paralogs are evolutionarily related genes that have similar sequence and similar functions. Orthologs are structurally related genes in different species that are derived by a speciation event. Paralogs are structurally related genes within a single species that are derived by a duplication event. Within a single plant species, gene duplication may result in two copies of a particular gene, giving rise to two or more genes with similar sequence and often similar function known as paralogs. A paralog is, therefore, a similar gene formed by duplication within the same species. Paralogs typically cluster together or in the same clade (a group of similar genes) when a gene family phylogeny is analyzed using programs such as CLUSTAL (Thompson, et al. (1994) *Nucleic Acids Res.* 22:4673-4680; Higgins, et al. (1996) *Methods Enzymol.* 266:383-402). Groups of similar genes can also be identified with pair-wise BLAST analysis (Feng and Doolittle (1987) *J. Mol. Evol.* 25:351-360). Orthologous sequences can also be identified by a reciprocal BLAST strategy. Once an orthologous sequence has been identified, the function of the ortholog can be deduced from the identified function of the reference sequence. Orthologous genes from different organisms have highly conserved functions, and very often essentially identical functions (Lee, et al. (2002) *Genome Res.* 12:493-502; Remm, et al. (2001) *J. Mol. Biol.* 314:1041-1052). Paralogous genes, which have diverged through gene duplication, may retain similar functions of the encoded proteins. In such cases, paralogs can be used interchangeably with respect to certain embodiments of this disclosure (for example, transgenic expression of a coding sequence).

Transaldolase polynucleotides, such as those disclosed herein, can be used to isolate homologs, paralogs and orthologs. In this manner, methods such as PCR, hybridization, and the like, can be used to identify such sequences based on their sequence homology to the transaldolase polynucleotide. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like. By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence-based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

In hybridization techniques, all or part of a known polynucleotide is used as a probe that selectively hybridizes to other nucleic acids comprising corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as P, or any other detectable marker. Thus, for example, probes for hybridization can be made by labeling synthetic oligonucleotides based on the transaldolase sequences disclosed herein. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire transaldolase sequences disclosed herein, or one or more portions thereof, may be used as probes capable of specifically hybridizing to corresponding transaldolase sequences and messenger RNAs. To achieve specific hybridization under a variety of conditions, such probes include sequences that are unique among transaldolase sequences and are at least about 10, 12, 15, 16, 17, 18, 19, 20, 21, 22, 23, 24, 25, 30, 35, 40, 50, 60, 70, 80, 90, or more nucleotides in length. Such probes may be used to amplify corresponding transaldolase sequences from a chosen plant by PCR. This technique may be used to isolate additional coding sequences from a desired plant or as a diagnostic assay to determine the presence of coding sequences in a plant. Hybridization techniques include hybridization screening of plated nucleic acid (e.g., DNA) libraries (either plaques or colonies; see, for example, Sambrook et al. (1989) *Molecular Cloning: A Laboratory Manual* (2d ed., Cold Spring Harbor Laboratory Press, Plainview, N.Y.). By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel (1987) *Guide to Molecular Cloning Techniques* from the series *Methods in Enzymology*, vol. 152, Academic Press, Inc., San Diego, Calif.; Sambrook, et al., (1989) *Molecular Cloning: A Laboratory Manual*, 2$^{nd}$ ed., vols. 1-3; and *Current Protocols in Molecular Biology*, Ausubel, et al., eds, *Current Protocols* is a joint venture between Greene Publishing Associates, Inc. and John Wiley & Sons, Inc. (1994 Supplement).

Hybridization of such sequences may be carried out under stringent conditions. The terms "stringent conditions" or "stringent hybridization conditions" include reference to conditions under which a probe will hybridize to its target sequence, to a detectably greater degree than other sequences (e.g., at least two-fold over background). Stringent conditions are sequence-dependent and will be different in different circumstances. By controlling the stringency of the hybridization and/or washing conditions, target sequences can be identified that can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS at 37° C., and a wash in 1× to 2×SSC at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-84: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application, "high stringency" is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA and 25 mM Na phosphate at 65° C. and a wash in 0.1×SSC, 0.1% SDS at 65° C.

The term "selectively hybridizes" includes reference to hybridization, under stringent hybridization conditions, of a nucleic acid sequence to a specified nucleic acid target sequence to a detectably greater degree (e.g., at least two-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other. The term "hybridization complex" includes reference to a duplex nucleic acid structure formed by two single-stranded nucleic acid sequences selectively hybridized with each other.

In yet another embodiment, the disclosure provides for a chimeric gene comprising the following operably linked DNA elements: a) a plant-expressible promoter, b) a DNA region encoding for a polypeptide depicted in SEQ ID NO:2, 4, 6, 8, 10, 12, 14, 16, 18, 20, 22 or 24 and c) a 3' end region comprising transcription termination and polyadenylation signals functioning in cells of a plant.

In this disclosure, a "plant-expressible promoter" comprises regulatory elements, which mediate the expression of a coding sequence segment in plant cells. For expression in plants, the nucleic acid molecule must be linked operably to or comprise a suitable promoter that expresses the gene at the right point in time and with the required spatial expression pattern. For the identification of functionally equivalent promoters, the promoter strength and/or expression pattern of a candidate promoter may be analyzed, for example, by operably linking the promoter to a reporter gene and assaying the expression level and pattern of the reporter gene in various tissues of the plant. Suitable well-known reporter genes include, for example, beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of this disclosure). Alternatively, promoter strength may be assayed by quantifying mRNA levels or by comparing mRNA levels of the nucleic acid used in the methods of the disclosure, with mRNA levels of housekeeping genes such as 18S rRNA, using methods known in the art, such as Northern blotting with densitometric analysis of autoradiograms, quantitative real-time PCR or RT-PCR (Heid et al., 1996 *Genome Methods* 6:986-994). Generally, by "weak promoter" is intended a promoter that drives expression of a coding sequence at a low level. By "low level" is intended at levels of about 1/10,000 transcripts to about 1/100,000 transcripts, to about 1/500,000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a lower level than a strong promoter, in particular, at a level that is in all instances below that obtained when under the control of a 35S CaMV promoter.

The term "operably linked" as used herein refers to a functional linkage between the promoter sequence and the gene of interest, such that the promoter sequence is able to initiate transcription of the gene of interest.

A "constitutive promoter" refers to a promoter that is transcriptionally active during most, but not necessarily all, phases of growth and development and under most environmental conditions, in at least one cell, tissue or organ. A "ubiquitous" promoter is active in substantially all tissues or cells of an organism. A developmentally regulated promoter is active during certain developmental stages or in parts of the plant that undergo developmental changes. An inducible promoter has induced or increased transcription initiation in response to a chemical (for a review, see Gatz 1997, *Ann. Rev. Plant Physiol. Plant Mol. Biol.*, 48:89-108), environmental or physical stimulus, or may be "stress-inducible," i.e., activated when a plant is exposed to various stress conditions, or a "pathogen-inducible," i.e., activated when a plant is exposed to various pathogens. An organ-specific or tissue-specific promoter is one that is capable of preferentially initiating transcription in certain organs or tissues, such as the leaves, roots, seed, tissue, etc. For example, a "root-specific promoter" is a promoter that is transcriptionally active predominantly in plant roots, substantially to the exclusion of any other parts of a plant, while still allowing for any leaky expression in these other plant parts. Promoters able to initiate transcription in certain cells only are referred to herein as "cell-specific." A seed-specific promoter is transcriptionally active predominantly in seed tissue, but not necessarily exclusively in seed tissue (in cases of leaky expression). The seed-specific promoter may be active during seed development and/or during germination. The seed-specific promoter may be endosperm/aleurone/embryo specific. Examples of seed-specific promoters are given in Qing Qu and Takaiwa (*Plant Biotechnol. J.* 2, 113-125, 2004), which disclosure is incorporated by reference herein as if fully set forth. A "green tissue-specific promoter" as defined herein is a promoter that is transcriptionally active predominantly in green tissue, substantially to the exclusion of any other parts of a plant, while still allowing for any leaky expression in these other plant parts.

Examples of constitutive promoters capable of driving such expression are the 35S, rice actin, maize ubiquitin, and eIF-4A promoters.

Particularly preferred promoters in the context of this disclosure are lignin-specific promoters such as the promoter of the gene C4H (K. Meyer et al. (1998) PNAS 95 (12): 6619-6623), fiber-specific promoters (pSND1 as depicted in SEQ ID NO:26, pNST1 (R. Zhong and Z-H Ye (2007) *Current Opinion in Plant Biology* 10:564-572) and depicted in SEQ ID NO:25; vessel-specific promoters (such as VND6 and VND7 (M. Kubo et al. (2005) *Genes and Development* 19:1855-1860; M. Yamaguchi et al. (2011) *The Plant Journal* 66(4)579-590), sequences depicted in SEQ ID NOS:27 and 28.

The term "terminator" encompasses a control sequence that is a DNA sequence at the end of a transcriptional unit that signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

"Selectable or screenable marker," "selectable or screenable marker gene" or "reporter gene" includes any gene that confers a phenotype on a cell in which it is expressed to facilitate the identification and/or selection of cells that are transfected or transformed with a nucleic acid construct of the disclosure. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example, bar, which provides resistance to BASTA®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or anti-nutritive markers such as the resistance to 2-deoxyglucose). Expression of visual marker genes results in the formation of color (for example, β-glucuronidase, GUS or β-galactosidase with its colored substrates, for example, X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells, together with the gene of interest. These markers can, for example, be used in mutants in which these genes are not functional by, for example, deletion by conventional methods. Furthermore, nucleic acid molecules encoding a selectable marker can be introduced into a host cell on the same vector that comprises the sequence encoding the polypeptides of the disclosure or used in the methods of the disclosure, or else in a separate vector. Cells that have been stably transfected with the introduced nucleic acid can be identified, for example, by selection (for example, cells that have integrated the selectable marker survive, whereas the other cells die).

Since the marker genes, particularly genes for resistance to antibiotics and herbicides, are no longer required or are undesired in the transgenic host cell once the nucleic acids have been introduced successfully, the process according to the disclosure for introducing the nucleic acids advantageously employs techniques that enable the removal or excision of these marker genes. One such method is what is known as "co-transformation." The co-transformation method employs two vectors simultaneously for the transformation, one vector bearing the nucleic acid according to the disclosure and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e., the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has successfully taken place and is lost. In a further number of cases, the transposon jumps to a different location. In these cases, the marker gene must be eliminated by performing crosses. In microbiology, techniques were developed that make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has successfully taken place, by expression of the recombinase. Further recombination systems are the HIN/HIX, FLP/FRT and REP/STB system (Tribble et al., *J. Biol. Chem.*, 2000 275:22255-22267; Velmurugan et al., *J. Cell Biol.*, 2000 149:553-566). A site-specific integration into the plant genome of the nucleic acid sequences according to the disclosure is possible. Similarly, marker genes can be excised using one or more rare-cleaving double-strand break-inducing enzyme such as meganucleases (naturally occurring or engineered to recognize a specific DNA sequence), zinc finger nucleases, TALE nucleases and the like, if recognition sites for such enzymes are present in the vicinity of the marker gene. Excision can occur via homologous recombination if homology regions flank the marker gene, or via non-homologous end-joining with two recognition sites flanking the marker gene.

For the purposes of the disclosure, "transgenic," "transgene," or "recombinant" means with regard to, for example, a nucleic acid sequence, an expression cassette, gene construct or a vector comprising the nucleic acid sequence or an organism transformed with the nucleic acid sequences, expression cassettes or vectors according to the disclosure. The term "nucleic acid molecule" as used interchangeably with the term "polynucleotide" in accordance with the disclosure, includes DNA, such as cDNA or genomic DNA, and RNA.

A transgenic plant for the purposes of the disclosure is thus understood as meaning, as above, that the nucleic acids used in the method of the disclosure (e.g., the chimeric genes) are not present in, or originating from, the genome of the plant, or are present in the genome of the plant but not at their natural locus in the genome of the plant, it being possible for the nucleic acids to be expressed homologously or heterologously. However, as mentioned, transgenic also means that, while the nucleic acids according to the disclosure or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the disclosure at an unnatural locus in the genome, i.e., homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

In a particular embodiment, a chimeric gene is provided comprising a chimeric gene consisting of the following elements: i) a plant expressible promoter, ii) a plant transaldolase as herein described before and iii) a plant terminator.

In yet another particular embodiment, the disclosure provides plants comprising a chimeric gene consisting of the following elements: i) a plant expressible promoter, ii) a plant transaldolase as herein described before and iii) a plant terminator.

In a particular embodiment plants with an enhanced expression of transaldolase comprise more lignin. Such transgenic plants are useful for generating plants with an enhanced caloric value (e.g., for pyrolysis and stronger wood quality).

The term "increased expression" or "overexpression" as used herein means any form of expression that is additional to the original wild-type expression level. For the purposes of this disclosure, the original wild-type expression level might also be zero, i.e., absence of expression or immeasurable expression.

Methods for increasing expression of genes or gene products are well documented in the art and include, for example, overexpression driven by appropriate promoters (as described hereinbefore), the use of transcription enhancers or translation enhancers. Isolated nucleic acids that serve as promoter or enhancer elements may be introduced in an appropriate position (typically upstream) of a non-heterologous form of a polynucleotide so as to up-regulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively, from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) *Mol. Cell Biol.* 8:4395-4405; Callis et al. (1987) *Genes Dev.* 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: *The Maize Handbook*, Chapter 116, Freeling and Walbot, Eds., Springer, N.Y. (1994).

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the disclosure and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, mega-gametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (F. A. Krens, et al. (1982) *Nature* 296:72-74; I. Negrutiu et al. (1987) *Plant Mol. Biol.* 8:363-373); electroporation of protoplasts (R. D. Shillito et al. (1985)-*Bio/Technol.* 3:1099-1102); microinjection into plant material (A. Crossway et al. (1986) *Mol. Gen. Genet.* 202:179-185); DNA or RNA-coated particle bombardment (T. M. Klein et al. (1987) *Nature* 327:70) infection with (non-integrative) viruses, and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the disclosure to allow a suspension of transformed agrobacteria to act on the intact plant or at least on the flower primordia. The plant is subsequently grown until the seeds of the treated plant are obtained (Clough and Bent (1998) *Plant J.* 16:735-743). Methods for *Agrobacterium*-mediated transformation of rice include well-known methods for rice transformation, such as those described in any of the following: European patent application EP1198985, Aldemita and Hodges (*Planta* 199:612-617, 1996); Chan et al. (*Plant Mol. Biol.* 22 (3):491-506, 1993), Hiei et al.—(*Plant J.* 6 (2):271-282, 1994), which disclosures are incorporated by reference herein as if fully set forth. In the case of corn transformation, the preferred method is as described in either Ishida et al. (*Nat. Biotech.* 14(6):745-50, 1996) or Frame et al. (*Plant Physiol.* 129(1):13-22, 2002), which disclosures are incorporated by reference herein as if fully set forth. These methods are further described by way of example in B. Jenes et al., "Techniques for Gene Transfer," in *Transgenic Plants*, Vol. 1, Engineering and Utilization, eds. S. D. Kung and R. Wu, Academic Press (1993) 128-143, and in Potrykus, *Annu. Rev. Plant Physiol. Plant Mol. Biol.* (1991) 42:205-225). The nucleic acids or the construct to be expressed is preferably cloned into a vector, which is suitable for transforming *Agrobacterium tumefaciens*, for example, pBin19 (Bevan et al. (1984) *Nucl. Acids Res.* 12-8711). Agrobacteria transformed by such a vector can then be used in known manner for the transformation of plants, such as plants used as a model, like *Arabidopsis* or crop plants such as, by way of example, tobacco plants, for example, by immersing bruised leaves or chopped leaves in an agrobacterial solution and then culturing them in suitable media. The transformation of plants by means of *Agrobacterium tumefaciens* is described, for example, by Hofgen and Willmitzer in *Nucl. Acid Res.* (1988) 16:9877, or is known inter alia from F. F. White, "Vectors for Gene Transfer in Higher Plants" in *Transgenic Plants*, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and, in particular, those cells that develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [K. A. Feldman and M. D. Marks (1987), *Mol. Gen. Genet.* 208:1-9; K. Feldmann (1992) in C. Koncz, N-H Chua and J. Shell, eds, *Methods in Arabidopsis Research*, Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994) *Plant J.* 5:551-558; Katavic (1994) *Mol. Gen. Genet.* 245:363-370). However, an especially effective method is the vacuum infiltration method with its modifications such as the "floral dip" method. In the case of vacuum infiltration of *Arabidopsis*, intact plants under reduced pressure are treated with an agrobacterial suspension [N. Bechthold (1993) *CR Acad. Sci. Paris Life Sci.* 316:1194-1199], while in the case of the "floral dip" method, the developing floral tissue is incubated briefly with a surfactant-treated agrobacterial suspension [S. J. Clough and A. F. Bent (1998) *The Plant J.* 16:735-743]. A certain proportion of transgenic seeds are harvested in both cases, and these seeds can be distinguished from non-transgenic seeds by growing under the above-described selective conditions. In addition, the stable transformation of plastids is advantageous because plastids are inherited maternally in most crops, reducing or eliminating the risk of transgene flow through pollen. The transformation of the chloroplast genome is generally achieved by a process that has been schematically displayed in Klaus et al., 2004 [*Nature Biotechnology* 22(2):225-229]. Briefly, the sequences to be transformed are cloned together with a selectable marker gene between flanking sequences homologous to the chloroplast genome. These homologous flanking sequences direct site-specific integration into the plastome. Plastidal transformation has been described for many different plant species and an overview is given in Bock (2001) Transgenic plastids in basic research and plant biotechnology, *J. Mol. Biol.* 2001 Sep. 21; 312 (3):425-38, or P. Maliga (2003) Progress towards commercialization of plastid transformation technology, *Trends Biotechnol.* 21:20-28. Further biotechnological progress has recently been reported in the form of marker-free plastid transformants, which can be produced by a transient co-integrated maker gene (Klaus et al., 2004, *Nature Biotechnology* 22(2):225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers that are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance, using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then be further propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again, wherein each of the aforementioned comprises the gene/nucleic acid of interest.

In some embodiments, the plant cell according to the disclosure is non-propagating or cannot be regenerated into a plant.

Plants that are particularly useful in the methods of the disclosure include, in particular, monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g., *Avena sativa, Avena fatua, Avena byzantina, Avena fatua* var. *sativa, Avena hybrida), Averrhoa carambola, Bambusa* sp., *Benincasa hispida, Bertholletia excelsea, Beta vulgaris, Brassica* spp. (e.g., *Brassica napus, Brassica rapa* ssp. [canola, oil seed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g., *Elaeis guineensis,*

*Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g., *Glycine max, Soja hispida* or *Soja* max), *Gossypium hirsutum, Helianthus* spp. (e.g., *Helianthus annuus*), *Hemerocallis fulva, Hibiscus* spp., *Hordeum* spp. (e.g., *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g., *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g., *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g., *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g., *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

In a particularly preferred embodiment, the plants comprise a crop or grass species, hybrids and varieties including, for example, those belonging to the *Saccharum, Zea, Triticum, Secale, Hordeum, Glycine, Oryza, Sorghum, Lolium, Vitis* and *Medicago* genera. In addition, the term "plant" may encompass species, hybrids and varieties of the *Miscanthus, Panicum* (switchgrass), *Phalaris* (reed canary grass), *Cannabis* (hemp) genera—plants of this type may be grown as crops for use in bioenergy production (i.e., as dedicated bioenergy crops). In other embodiments, the term "plant" encompasses species, hybrids and varieties of trees such as Salix, Popuhs, and *Eucalyptus* genera.

In view of the above, it should be understood that the "plant biomass" for use in methods requiring or exploiting plant cell wall carbohydrates, for example, biofuel production, may comprise material or matter derived from modified forms (i.e., forms exhibiting modulated expression of one or more transaldolases of any of the plants described herein. Further, a skilled person will appreciate that the term "biomass" may comprise any part of a plant including, for example, the stem, flower (including seed heads etc.), root and leaves. Where a modified plant provided by this disclosure exhibits modified lignin content throughout its cells and tissues, any part of that plant may yield biomass that is useful as feedstock for methods requiring plant carbohydrate extraction or methods of producing biofuel—of particular use are the stems and roots.

The choice of suitable control plants is a routine part of an experimental setup and may include corresponding wild-type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

A reduced lignin production in the sense of the disclosure leads to a reduction of lignin of the transgenic plants of 5%, 10%, 15%, 20% or more in comparison to the control plant growing under the same conditions.

In a particular embodiment, the transaldolase mutant plants or the transaldolase transgenic plants as described herein before can be combined with existing mutants (or transgenic plants) through crossing or super-transformation (i.e., double or even triple transformation). Non-limiting examples of combinations are combinations between a transaldolase 1 or 2 mutant (or transgenic plant with a reduced transaldolase 1 or 2 expression) with mutants in the genes encoding PAL1, PAL2, C4H, 4CL1, 4CL2, CCoAOMT1, CCR1, F5H1, COMT and CAD6. Without limiting the disclosure to a particular mode of action, it is believed that a combination between a transaldolase 1 or 2 mutant (or transgenic plant with a down-regulation for transaldolase 1 or 2) with mutants in classical lignin modifying genes (such as PAL1, PAL2, C4H, 4CL1, 4CL2, CCoAOMT1, CCR1, F5H1, COMT and CAD6) will lead to an additive effect or synergism because of the different cellular location in the lignin biosynthetic pathways.

In a particular embodiment, the disclosure provides a plant with a reduced expression of a transaldolase and a COMT (caffeic acid 3-O-methyltransferase) gene. In yet another particular embodiment, the disclosure provides a plant or plant cell having a reduced expression of the COMT gene and a chimeric gene, according to the disclosure, for the down-regulation of transaldolase. Methods for generating plants with a reduced expression of the COMT gene are known in the art and are similar to methods that are described herein for the generation of plants or plant cells with a reduced expression in the transaldolase 1 or 2 gene.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

EXAMPLES

1. Collection of Lignin Mutants and Analysis of Growth Dynamics

To study the system-wide consequences of lignin pathway perturbations, a set of *Arabidopsis* lines was collected, each with a mutation in a single gene of the general phenylpropanoid or monolignol-specific pathway (FIG. 1). For ten genes of the pathway (PAL1, PAL2, C4H, 4CL1, 4CL2, CCoAOMT1, CCR1, F5H1, COMT and CAD6), two independent mutants were selected that were suitable for the approach (FIG. 12). Mutants in C3H and HCT were sub-lethal and were left out of the analysis. Plants were grown under conditions identified to allow the development of a single, strong inflorescence stem with a maximum of secondary cell wall thickening, i.e., shifting plants from short-day (9 hours light/15 hours dark) to long-day conditions (16 hours light/8 hours dark) when the average rosette reached a diameter of about 6 cm. Ideally, all lines needed to be equally developed at harvest to avoid developmental shifts (previously described for c4h-2, ccr1-3 and ccr1-6; Jones et al. (2001); Mir Derikvand et al. (2008); Schilmiller et al. (2009)), from superimposing uninformative molecular changes on the more direct effects of the perturbed lignin pathway. Stem growth rate was slower than WT in c4h-2, ccr1-3, ccr1-6 and ccoaomt1-3, while cad6-1 grew faster (FIG. 12). The differences between ccoaomt1-3 or cad6-1 and WT were small and, after 44 days in long day conditions, when all plants ceased growing, only c4h-2, ccr1-3 and ccr1-6 had a significantly reduced final stem height compared to WT (FIG. 12). In order to partially compensate for the developmental delay of these mutant lines, they were sown two weeks prior to the other lines for all subsequent analyses.

2. Deep Phenotyping of Mutants Via Transcriptomics and Metabolomics

Figure 2:
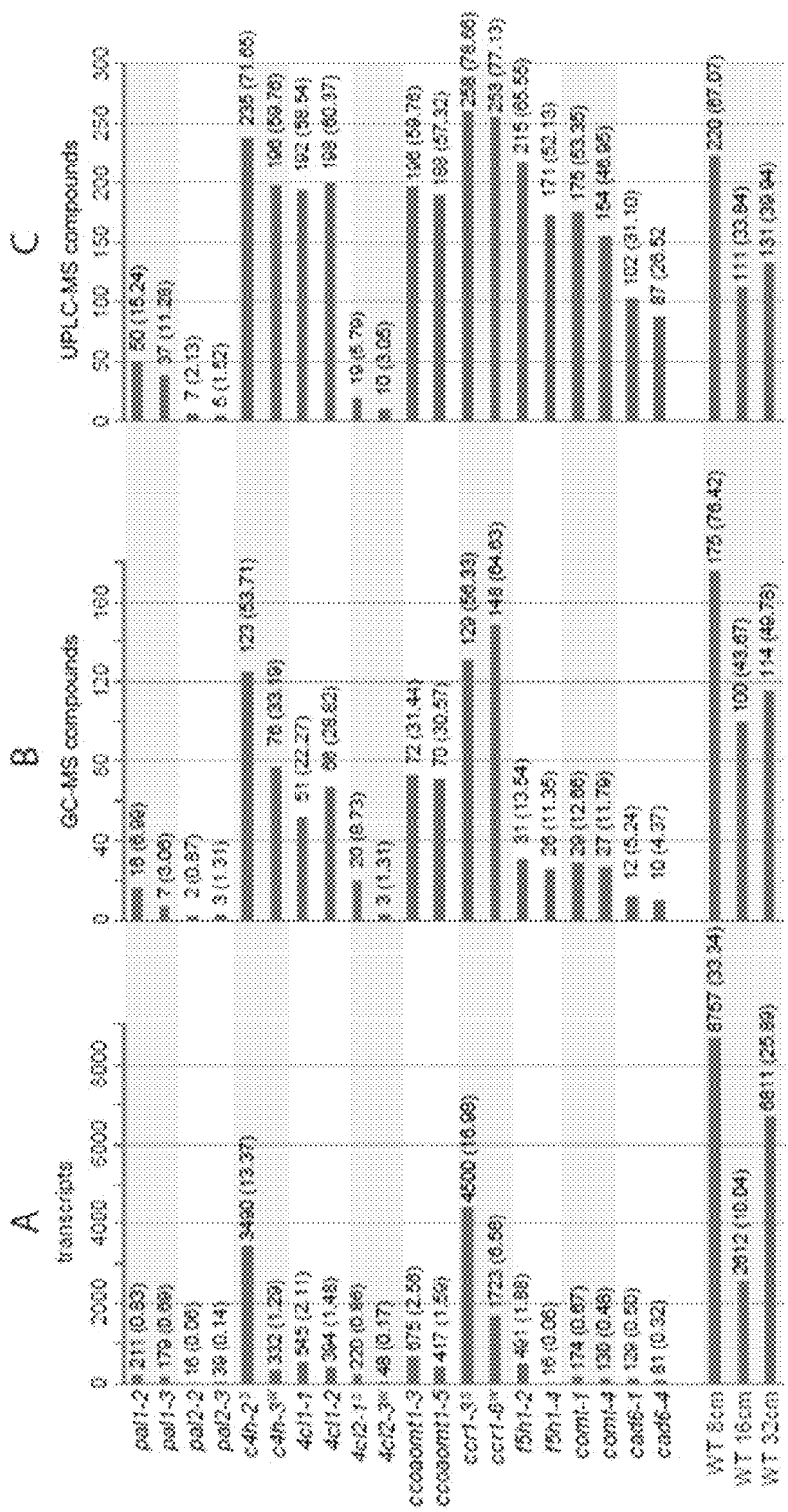
FIG. 2: Number of transcripts and compounds that are significantly different in abundance compared to WT 24 cm, in each mutant line and in the WT developmental stages. (A) Number of gene probes that are significantly different as compared to WT 24 cm. Between brackets: expressed as percentage of protein coding gene-representing probes present on the array. (B) Number of compounds detected by GC-MS that accumulate differentially as compared to WT 24 cm. Between brackets: expressed as percentage of the total number of compounds detected by GC-MS. (C) Number of compounds detected by UPLC-MS that accumulate differentially as compared to WT 24 cm. Between brackets: expressed as percentage of the total number of compounds detected by UPLC-MS. Red superscripts s and w indicate the stronger and weaker mutant alleles, respectively: substantial residual 4CL2 transcript levels were detected in 4cl2-3 in this study, and the alleles of c4h and ccr1 are described in Schilmiller et al. (2009) and Mir Derikvand et al. (2008).

Replicate samples were taken from 8, 16, 24 and 32 cm tall WT inflorescence stems to evaluate metabolic and transcriptomic shifts during stem development and these were called WT 8 cm, WT 16 cm, WT 24 cm and WT 32 cm, respectively. The mutant lines were harvested in replicate simultaneously with and at the same height as WT 24 cm with the exceptions of ccr1-6, which was only 19 cm high, and c4h-2 and ccr1-3, which were harvested simultaneously with WT 32 cm at 12 and 16 cm high, respectively. The basal 1-9 cm (1-6 cm in case of WT 8 cm) of the inflorescence stems was used for both transcript and metabolite profiling, because this region of the stem is relatively enriched in lignifying cells (Nieminen et al., 2004). Gene expression in the inflorescence stem of the twenty mutant lines and the four WT developmental stages was analyzed using Agilent Arabidopsis 3 oligo arrays, harboring 32,221 probes for 25,094 genes (covering 91.53% of the protein coding genes (PCGs) according to the TAIR10 annotated genome). For metabolomics, two different separation techniques were used to cover a wide range of metabolites. Small polar metabolites such as sugars, sugar alcohols, amino acids and small organic acids, were determined via a standard Gas Chromatography-Mass Spectrometry (GC-MS) method (Roessner et al., 2000; Fernie et al., 2004), whereas phenolic compounds were detected via an established in-house Ultra-high Performance Liquid Chromatography-Mass Spectrometry (UPLC-MS) method (Morreel et al., 2004; Morreel et al., 2010b; Morreel et al., 2010a). The intensity of 26,787 probes (86.14% of the PCGs on the array) was well above background in at least one of the four sampled stages during WT stem development. Statistical analysis revealed that the signal of 12,291 probes (46.25% of the PCGs on the array) changed significantly during WT stem development, with WT 24 cm used as the reference sample. In comparison, only 7,099 probes (26.91% of the PCGs on the array) were significantly different in at least one of the mutant lines as compared to WT 24 cm. This indicates that the overall change in gene expression provoked by a mutation was more subtle than that caused by progressive development of the inflorescence stem. Remarkably, mutants that had no obvious morphological phenotypes nor developmental shifts (i.e., all mutants except c4h-2, ccr1-3 and ccr1-6) still had up to 675 probes (2.56% of the PCGs on the array) with a signal that was different from the signal in WT 24 cm (FIG. 2, column A). With GC-MS, 229 compounds were detected in at least one of the lines, 59 of which could be identified by use of the GMD@CSB.DB-library (Kopka et al., 2005). A "compound" is defined here as a molecule that elutes at a certain retention time. Because of the derivatization procedure used, some metabolites are detected as multiple compounds (Kopka et al., 2005). The abundance of 86% of compounds varied significantly during WT stem development and the abundance of 93% was significantly altered in at least one of the mutant lines compared to WT 24 cm (FIG. 2, column B). Notably, the fraction of GC-MS detected metabolites that differ in abundance due to mutational and developmental effects was larger than the fraction of transcripts that differed in abundance. Finally, 337 compounds were detected via UPLC-MS of which 328 were integrated and aligned using the MetAlign software (Lommen, 2009), and 9 were manually integrated. 82% of the 328 automatically integrated compounds varied significantly in at least one of the developmental stages compared to WT 24 cm, whereas 99% varied significantly in at least one of the mutants (FIG. 2, column C). As with the GC-MS detected metabolites, the fraction of differential UPLC-MS detected metabolites was larger in the mutant compared to the developmental samples.

Overall, there was a remarkable similarity in the number of differentials between the two mutant alleles of each gene although this was less pronounced for the transcripts for mutants with a strong and a weak mutant allele. These data underscore the similar molecular response in both mutant alleles of a given gene.

Figure 3:
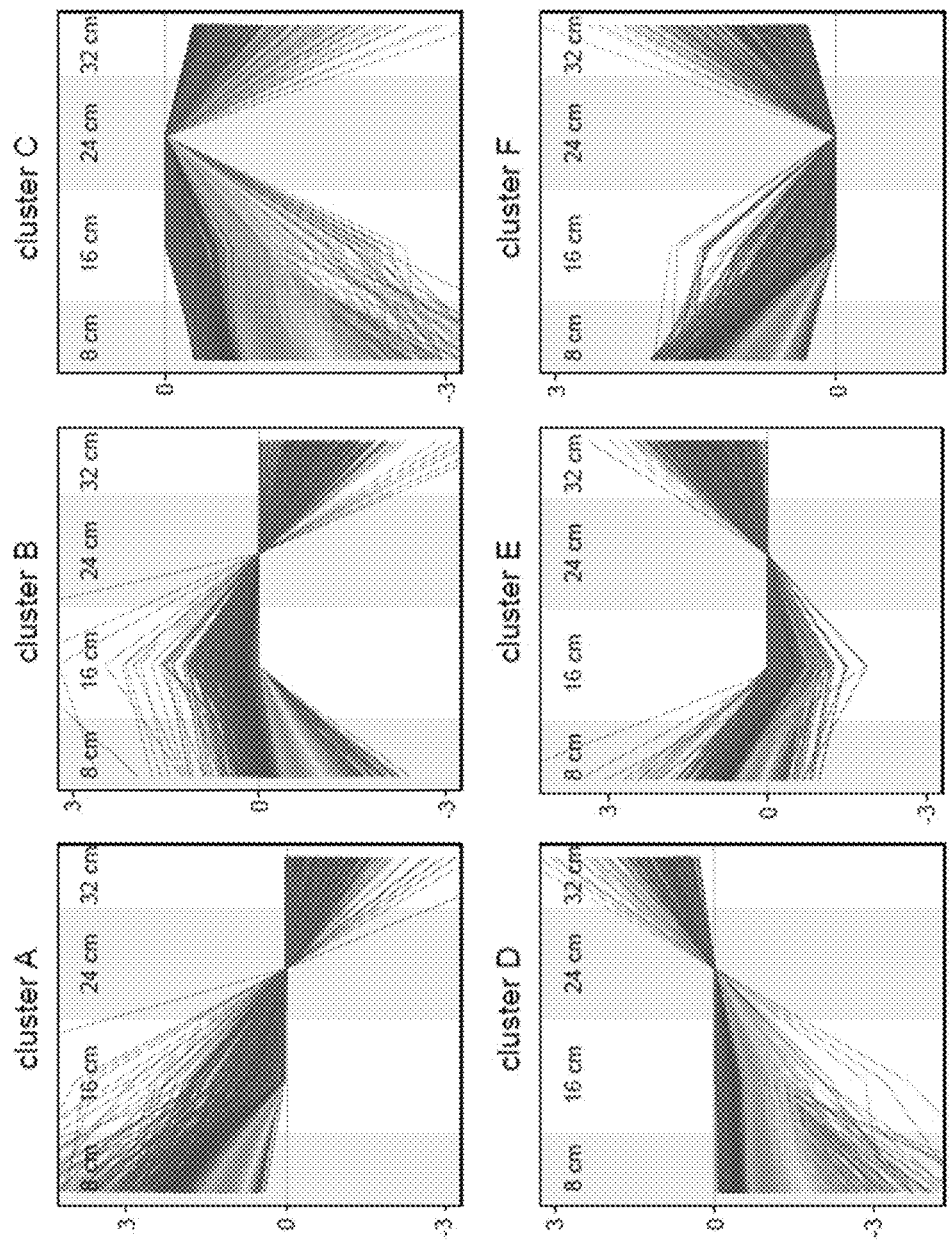
FIG. 3: Relative gene expression and metabolite abundance over stem development. Cluster A represents the profiles of 1,703 probes and 138 compounds that decreased over development. Cluster B shows the profiles of 936 probes and 12 metabolites that had a maximal abundance at the WT 16 cm stages, and are low early and late in development. Cluster C shows the profiles of 1,760 transcripts and 9 metabolites that had a maximal abundance at the WT 24 cm stages. Cluster D shows the profiles of 1,097 probes and 133 compounds that increased over stem development. Cluster E represents the profile of 1,089 probes and 40 metabolites with a minimum at WT 16 cm, but further increased from WT 16 cm onward. Cluster F shows the profiles of 840 probes and 22 compounds with a minimum at the WT 24 cm stage. The colors have no meaning but are only used to visualize the different profiles within each cluster.

3. Coordinated Transcript and Metabolite Changes During Inflorescence Stem Development To have a first idea of which biological processes are most prominent over the different stages of WT development, the 12,291 probes and 466 metabolites that were significantly differential over developmental time were grouped in clusters (A-F) according to their temporal profiles (FIG. 3). Cluster A grouped probes and compounds that were maximal at the WT 8 cm stage and decreased over development (1,703 probes representing 6.57% of the PCGs on the array, 102 GC-MS and 36 LC-MS compounds). Gene Ontology (GO)-analysis via BiNGO (Maere et al., 2005) revealed a significant over-representation of the cell cycle and related processes (microtubule biosynthesis, primary cell wall formation and DNA replication). Furthermore, cluster A contained about 45% of all compounds detected via GC-MS, including most of the amino acids, indicating that the earlier developmental stages have a high metabolic rate and are enriched in primary metabolism. Cluster A further contained secondary metabolites, such as the flavonol glycosides, and molecules derived from sinapic acid, e.g., sinapoyl malate and sinapic acid O-4 glucoside. Cluster B grouped 936 probes (3.57% of the PCGs on the array) and 12 compounds that had a maximal abundance at the WT 16 cm stage and of which the abundance was higher in WT 24 cm compared to WT 32 cm. GO-analysis proved the genes to be enriched in secondary cell wall-related processes, in particular, (glucurono)xylan biosynthesis. Cluster C grouped profiles of 1760 probes (6.69% of the PCGs on the array) and 9 compounds that increased in abundance up to the WT 24 cm stage and then decreased and was enriched in defense response, cell death and phenylpropanoid biosynthesis genes. PAL1, C4H, 4CL1, 4CL2, HCT, CCR1, CCoAOMT, F5H1 and COMT were present in this cluster. The occurrence of (glucurono)xylan biosynthesis and lignification in two separate clusters demonstrates the quality of the dataset that resolves, in time, two sequential processes of secondary cell wall formation. Cluster D represented probes and compounds for which the abundance increased over development. It consists of 1,097 probes (4.14% of the PCGs on the array) and 14 GC-MS and 119 LC-MS compounds. Genes in response-related processes were enriched, as well as transcription factors and genes involved in auxin transport. This cluster contained virtually all identified oligolignols and the primary metabolite shikimate. Cluster E grouped profiles that decreased from WT 8 cm to WT 16 cm but then increased (1,089 probes representing 4.18% of the PCGs on the array, and 40 metabolites. Glycolysis-related transcripts were enriched as were categories "translation" and "ribosome," perhaps reflecting a gradual change from starch respiration in young tissues toward photosynthesis and/or respiration of transported photo-assimilates in mature tissues. Consistent with the latter, both fructose-6-P and glucose-6-P were present in cluster E. Finally, cluster F represented 840 probes (3.23% of the PCGs on the array) and 22 compounds that decreased from WT 8 cm to a minimum in WT 24 cm then increased again in WT 32 cm. This cluster was enriched in photosynthesis and related GO-processes and contained the metabolites coniferin and fructose, and glutamine as one of the few amino acids that did not fall into cluster A.

4. Common System-Wide Responses in Lignin Mutants

Figure 4:
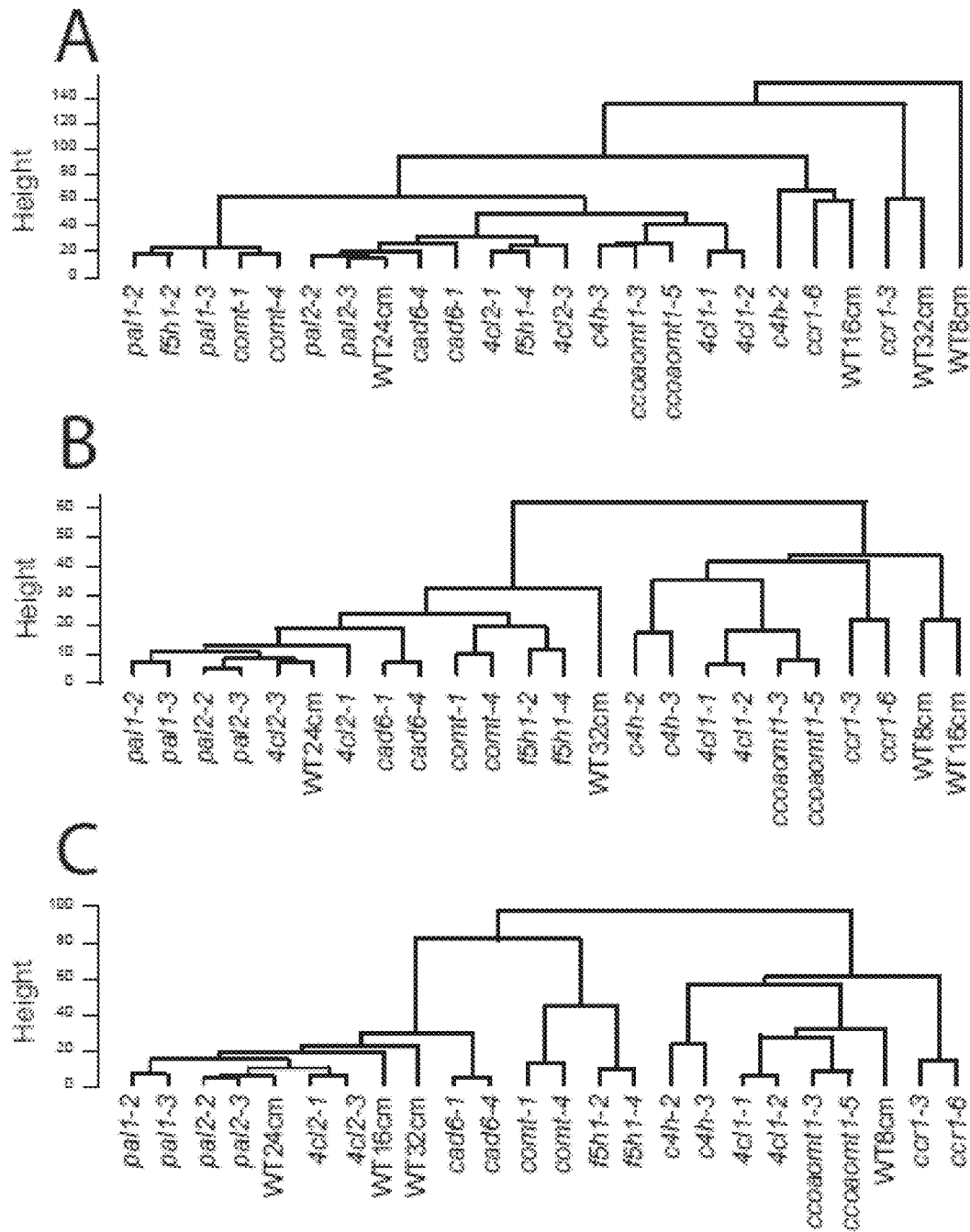
FIG. 4: Sample-based clustering of the mutant lines and WT developmental series: (A) Clustering based on the expression of 7,099 probes that were significantly different in at least one of the mutant lines; (B) Clustering based on 212 compounds measured by GC-MS; and (C) Clustering based on 325 compounds measured by UPLC-MS.
Figure 5A:
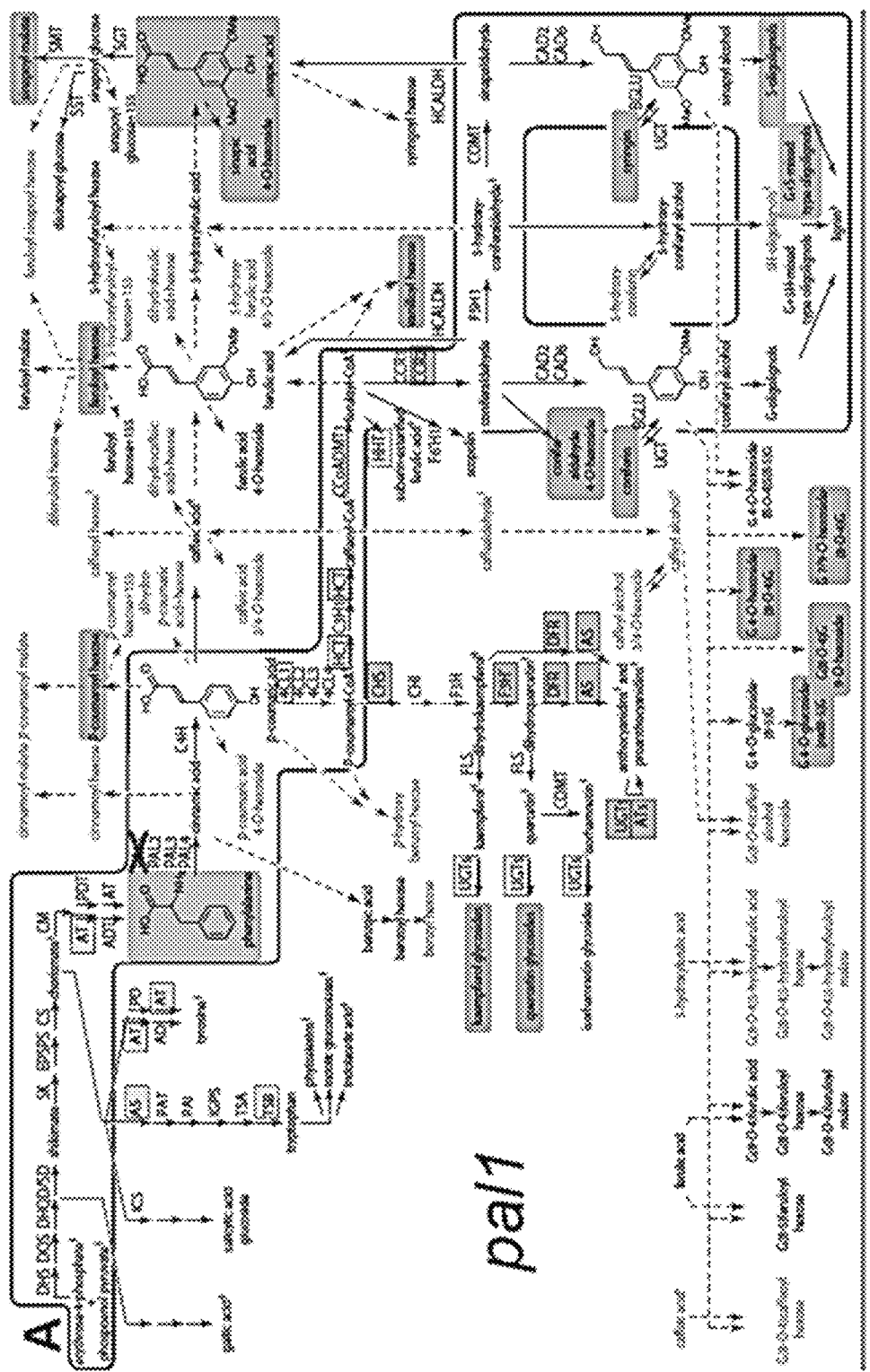
FIGS. 5A-5G: Metabolic shifts in phenolic metabolism as a result of a mutation in the lignin biosynthetic pathway. The relative increase and decrease of transcript and metabolite abundances in each of the mutants, as compared to WT 24 cm, was mapped manually on the pathway as discrete features. Differences in metabolites are indicated via round-angled boxes, where red represents a significant increase and blue a significant decrease in abundance. Differences in transcript abundance are indicated with right-angled, framed boxes: significant increases and decreases are visualized via red and blue boxes with solid borders, respectively, whereas tendencies ($\log_2$(abundance in the sample/abundance in WT 24 cm)<−0.3 or >0.3) are visualized via boxes with a pale fill and dashed-line borders. Metabolites that were below detection limit are given in grey. The effects in the pal1, c4h, 4cl1, ccoaomt1, ccr1, f5h1, comt and cad6 mutants are in panels A-H, as indicated. For abbreviations, see FIG. 1.
Figure 5B:
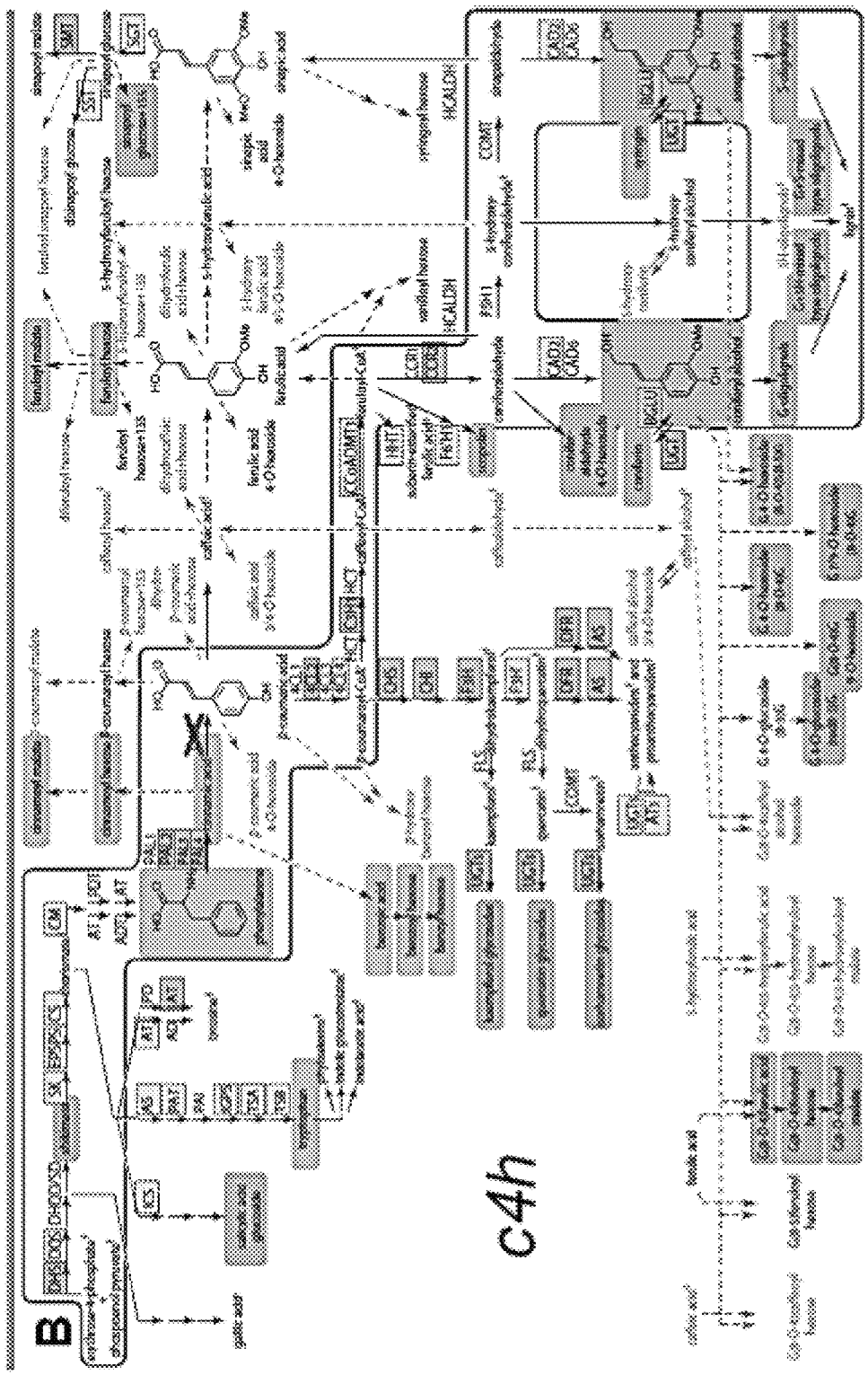
Figure 5C:
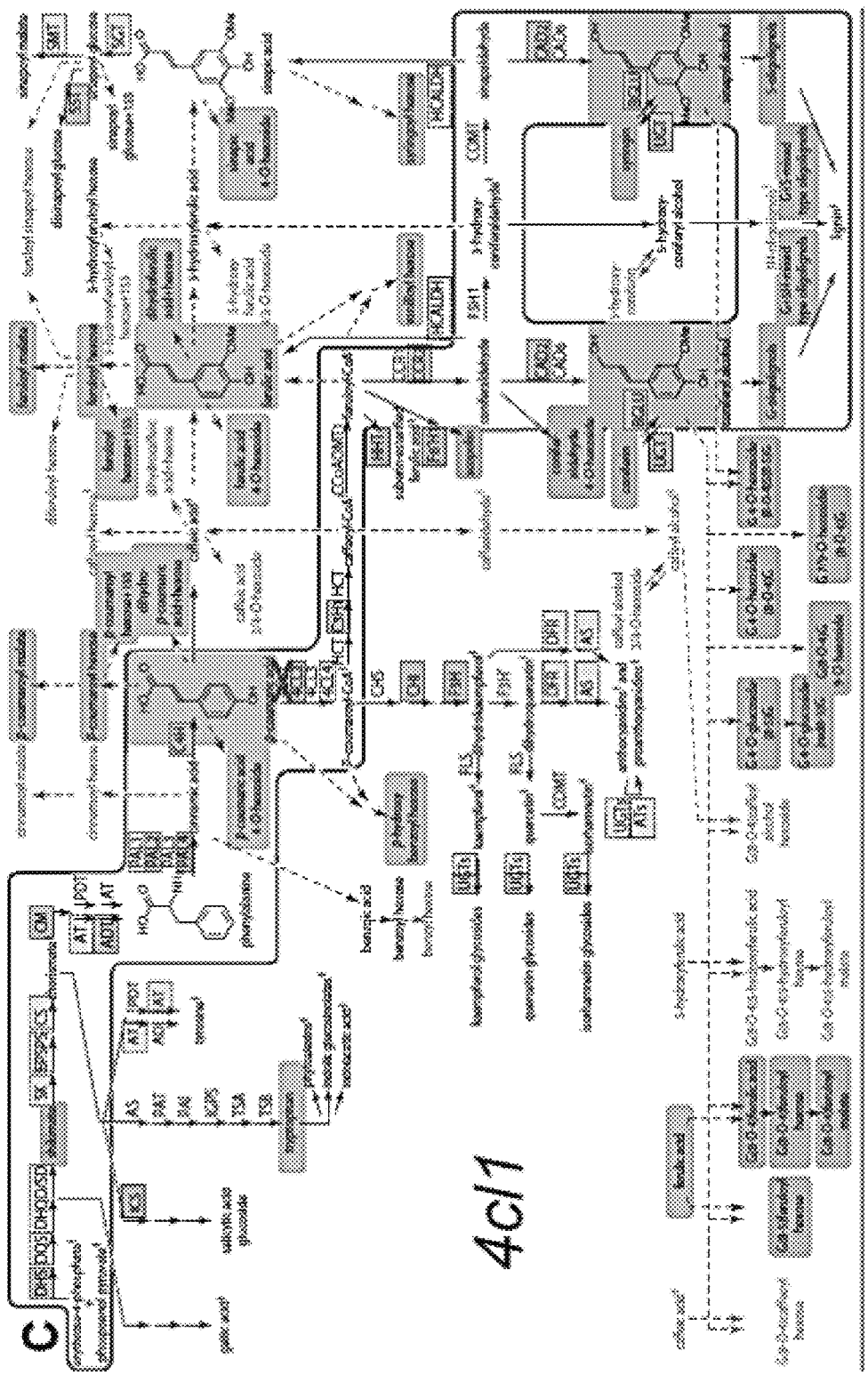
Figure 5D:
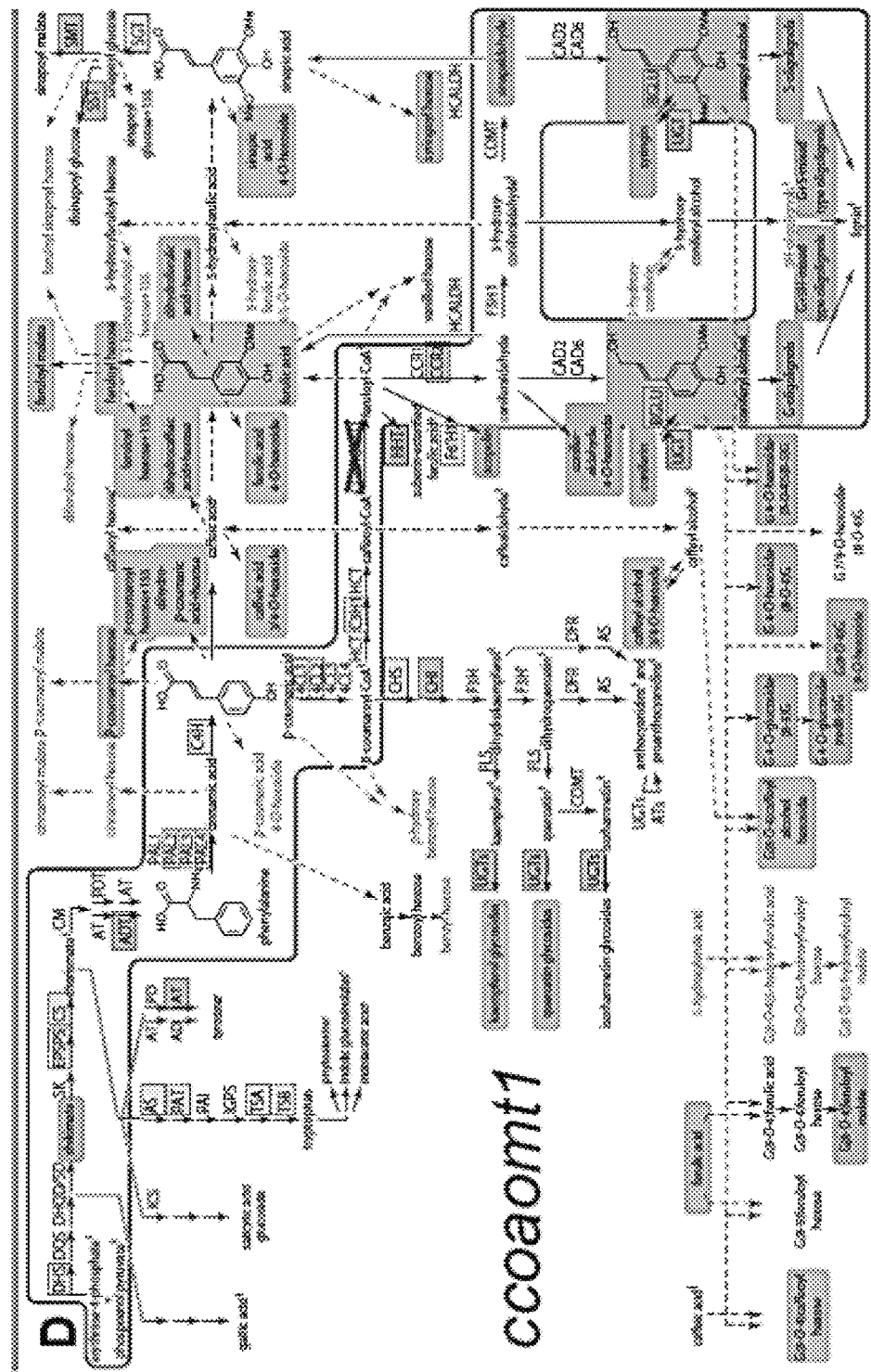
Figure 5E:
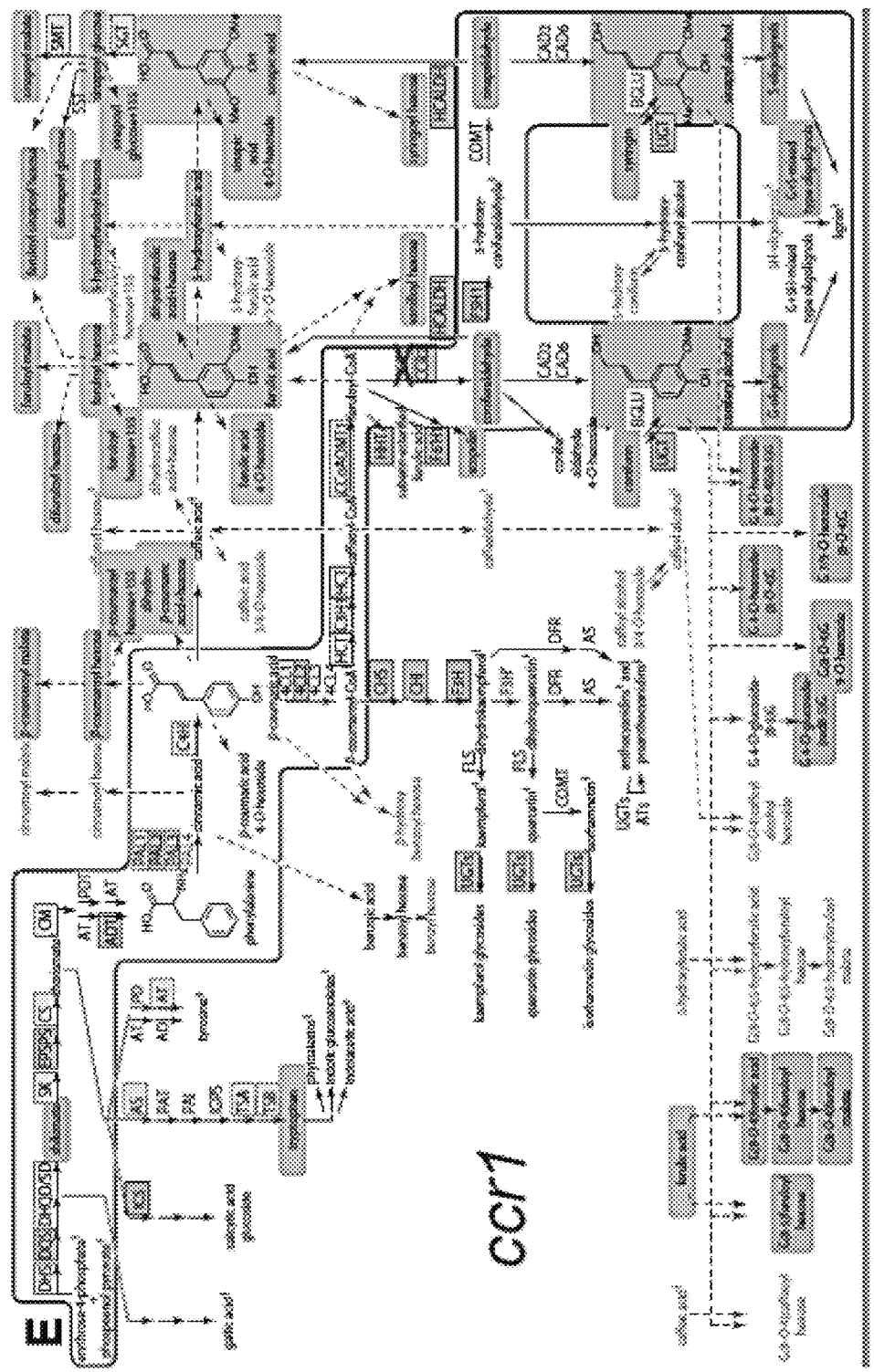
Figure 5F:
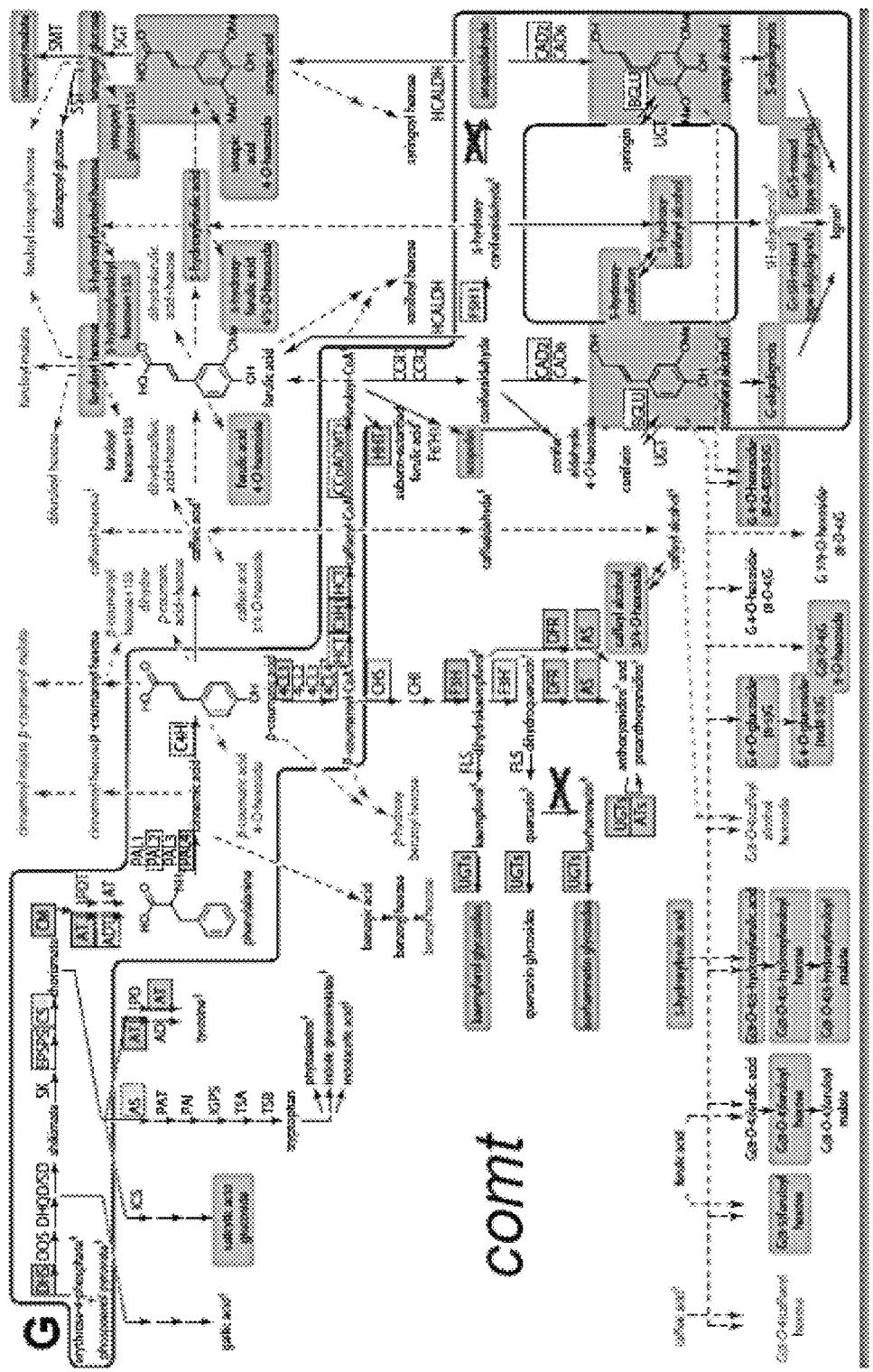
Figure 5G:
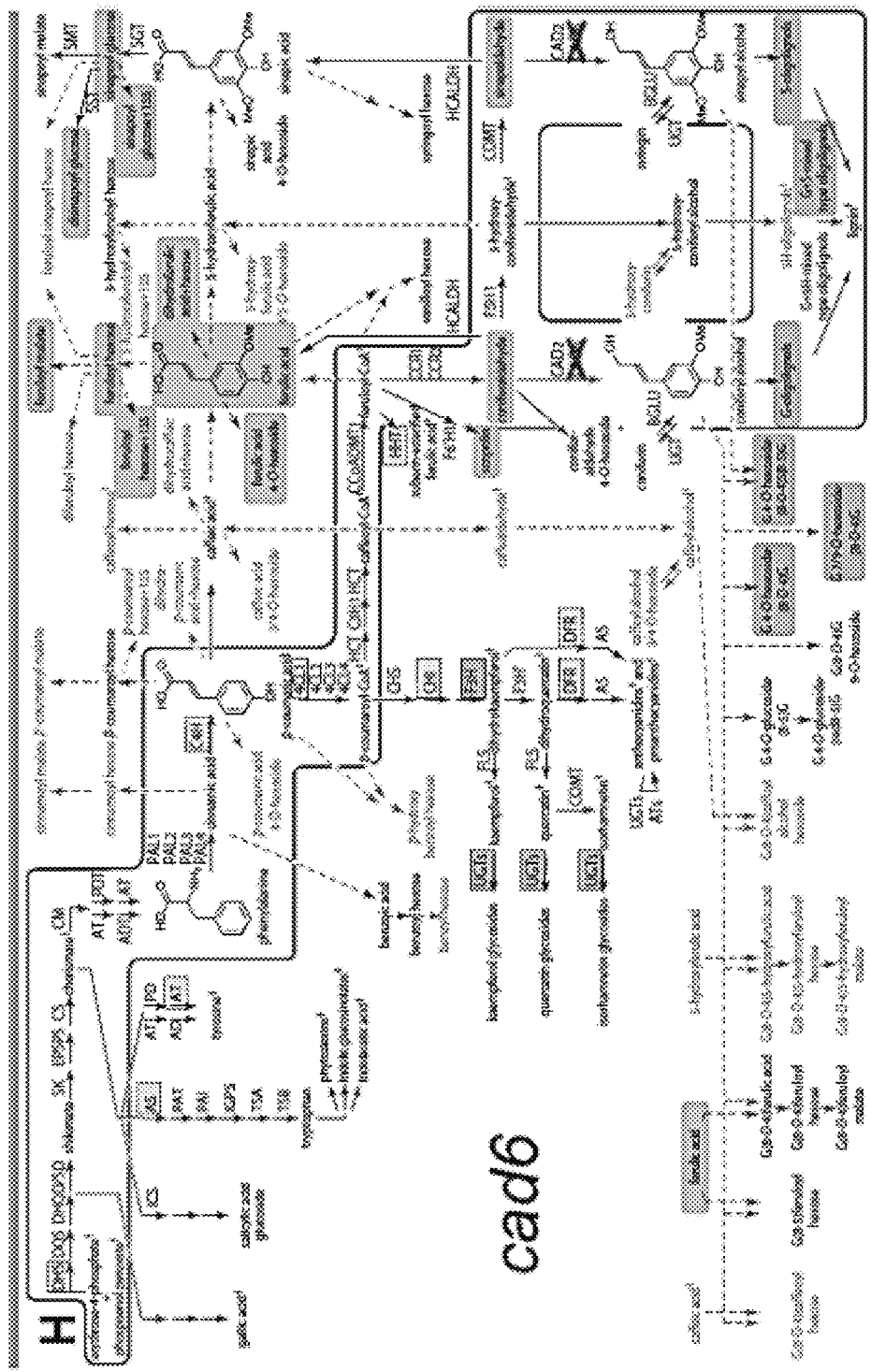

To visualize similarities in transcript and metabolite changes among the different mutants, mutant samples were clustered based on their transcript and metabolic profiles (FIG. 4). The two mutant alleles of each gene generally clustered together, emphasizing that they provoked a similar response. The only exceptions were the c4h, ccr1 and f5h1 lines in the transcript-based clustering. Notably, c4h-2 and ccr1 mutants clustered with WT of a different developmental stage, indicating that the advanced sowing of these mutant lines could not fully compensate for the developmental shift. A difference between the two alleles of both c4h and ccr1 was expected as these lines have a different residual C4H and CCR1 enzymatic activity (Mir Derikvand et al., 2008; Schilmiller et al., 2009). In contrast, the distinction between the two f5h1 lines was unexpected, especially because they nicely co-cluster in GC-MS- and UPLC-MS-based clustering. f5h1-2 was similar to comt mutants in the transcript-based clustering, which is in agreement with their respective enzymes catalyzing subsequent reactions in the S-unit specific branch of monolignol biosynthesis. The f5h1-4 mutant, on the other hand, was very similar to WT as both lines appeared to be co-clustered based on transcript data. Convincingly, mutants of the central part of the phenylpropanoid pathway (c4h-3, 4cl1-1, 4cl1-2, ccoaomt1-3 and ccoaomt1-5) grouped in a separate transcript-based sub-cluster. In both the GC- and the UPLC-MS-based clustering, this sub-cluster was further extended with the ccr1 alleles. This indicates that system-wide responses to pathway perturbations are similar in this group of mutants. Surprisingly, based on transcript data, pal1 mutants appeared in the same cluster as f5h1-2 and comt mutants. This is unexpected based on current knowledge of the pathway, because PAL1 is the very first enzyme in the general phenylpropanoid pathway, and F5H1 and COMT act on the downstream monolignol-specific pathway. Overall, the clusters obtained from the three different datasets were similar. For ease of interpretation, the average of the log-ratios of the expression/abundance values of the two alleles of pal1, pal2, 4cl1, 4cl2, ccoaomt1, comt and cad6 were taken for the figures, which is sound given the co-clustering of the respective alleles (FIG. 4). Only for c4h and ccr1, the data in figures were restricted to those of the allele that deviated least from the WT 24 cm, i.e., c4h-3 and ccr1-6. To visualize responses that are shared between the different mutants, the differential transcripts and compounds detected in pal1, pal2, c4h, 4cl1, 4cl2, ccoaomt1, ccr1, f5h1, comt and cad6 were compared with each other.

5. Metabolic Maps Reveal Shifts in Phenolic Metabolism Upon Pathway Perturbations The UPLC-MS approach was targeted toward phenolic compounds, i.e., intermediates and products of the perturbed phenylpropanoid and monolignol biosynthetic pathways. Of the 337 detected metabolites, all 128 tentatively structurally identified compounds were phenolic/aromatic; 34 compounds were identified based on their retention time and $MS^2$ data that were identical to those of standards, and 94 compounds were tentatively identified via $MS^2$ (Morreel et al., 2010b). The 128 tentatively identified phenolic compounds belonged to several metabolic classes as illustrated in FIG. 1. For each mutation, the altered abundances of metabolites and transcripts involved in phenolic metabolism were visualized by comparison with the control sample WT 24 cm (FIGS. 5A-5G). The metabolic and transcriptomic changes of the WT developmental series was similarly compared with WT 24 cm. The response of specific phenolic classes such as oligolignols, phenylpropanoid 4-O-hexosides, phenylpropanoic acid derivates, benzenoids and coniferyl alcohol-ferulic acid dimers, and their biosynthetic pathways, are described below.

5.1 Lignin, Oligolignols and their Biosynthesis

During the lignification process, monolignols are relocated to the cell wall, where they are oxidized and coupled in a combinatorial fashion to oligolignols and higher molecular weight lignin polymers. Based on their $MS^2$ spectra and retention times by UPLC-MS, 36 compounds found in WT stems were identified as oligolignols (di-, tri- and tetralignols). Oligolignol abundance increased during WT development. All oligolignols were less abundant in c4h, 4cl1, ccoaomt1 and ccr1 mutants, whereas f5h1 and comt mutants had reduced amounts of oligolignols that contained S-units (FIGS. 5A-5G). In f5h1 mutants, the reduction in oligolignols with at least one S-unit seemed to be compensated for by an increase in abundance of oligolignols that consist exclusively of G-units, whereas in comt mutants, oligolignols with 5-hydroxyguaiacyl (5H)-units (e.g., G(8-O-4)5H) accumulated, derived from coupling of a classical monolignol with 5-hydroxyconiferyl alcohol. To investigate the relation between oligolignol levels and lignin amount, acetyl bromide lignin was measured in the set of mutant and wild-type plants harvested at the same developmental stage. Notably, the relative abundance of the oligolignols in each of the mutants, as compared to WT 24 cm, largely reflected the relative amount of the lignin polymer. Genes involved in the general phenylpropanoid and the monolignol-specific pathway had maximal expression levels at the 16-24 cm stages in WT (FIG. 13). Remarkably, c4h, 4cl1, ccoaomt1 and ccr1 mutants, i.e., those mutants with reduced lignin levels, showed increased abundance of transcripts of the entire pathway from PAL to CCR (FIG. 13). Increased expression was most prominent in one gene family member of PAL, 4CL and CCR (i.e., PAL2, 4CL2 and CCR2). Strikingly, the opposite transcriptional response was observed in f5h1 and comt mutants that had normal amounts of lignin but were reduced in oligolignols with S-units (FIG. 13). Before polymerization, monolignols are oxidized by laccases and class III peroxidases. Based on the transcript abundance over WT development (FIG. 14), laccases and class III peroxidases could be divided in two sets. A first set had a maximal transcript abundance in WT 8 cm. This class is potentially involved in the oxidation of monomers for the production of phenylpropanoid dimers that are most abundant at the 8 cm stage. A second set (i.e., LAC2, 4, 11, 16 and 17 and ten peroxidases) had a maximal transcript abundance in WT 16 cm or 24 cm, the same stages at which lignin biosynthetic genes were also maximally expressed (FIG. 13). Most likely, this set of genes contains candidates involved in lignification. Of these, LAC2, LAC1, LAC17 and PER12 responded in the mutants in a similar way as the genes of the phenylpropanoid pathway did in the two groups of mutants (FIGS. 13 and 14), making them top-candidates for a role in monolignol oxidation. While this data was being prepared for publication, Berthet et al. (2011) provided the first undisputable evidence for a role of LAC17 in lignification, validating this hypothesis.

5.2 4-O-Glucosylated Monolignols and Their Metabolism

Coniferin and syringin are thought to be synthesized from their respective aglycone by glucosyltransferase UGT72E2 and UGT72E3. UGT72E2 accepts both coniferyl and sinapyl alcohols as substrate in vitro, whereas UGT72E3 is more specific for sinapyl alcohol (Lim et al., 2005; Lanot et al., 2006). Conversely, β-glucosidases (BGLU45-47) hydrolyze coniferin and syringin back into their respective aglycones in vitro (Escamilla-Treviño et al., 2006). Over WT development, the abundance of coniferin and syringin was highest at the 8 cm stage, but in the mutant samples, they largely followed the abundances of coniferyl and sinapyl alcohol, respectively. Expression of both UGT72E2 and UGT72E3 was reduced in c4h, 4cl1, ccoaomt1 and ccr1 mutants, while BGLU45-47 was increased in c4h, 4cl1 and ccoaomt1 mutants (FIG. 15). Thus, based on the transcript data, the biosynthesis of coniferin and syringin in the low lignin mutants (i.e., c4h, 4cl1, ccoaomt1 and ccr1) was reduced, while their hydrolysis was increased, which agrees with the observed abundances of coniferin and syringin.

5.3 Phenylpropanoic Acid Derivates

Specific phenylpropanoic acids (i.e., cinnamic, p-coumaric, caffeic, ferulic, 5-hydroxyferulic and sinapic acid) and derivates thereof, accumulated in each of the mutants (FIGS. 5A-5G). Most of these metabolites were below the detection limit in the WT plants and only found in certain mutants, but for each derivate type, a corresponding ferulic or sinapic acid-derived analog was detectable in WT, with the exception of hexose coupled to dihydrogenated phenylpropanoic acid (FIG. 1). Strikingly, neither caffeoyl glucose, nor caffeoyl malate were detected in ccoaomt1 mutants; instead, the flux in these mutants seemed to be driven toward ferulate esters, flavonol glycosides and coniferyl alcohol-caffeic acid dimers (i.e., G(8-O-4)caffeoyl hexose) (FIGS. 5A-5G). This shows that the excess of caffeoyl-CoA in ccoaomt1 mutants is metabolized differently from accumulating phenylpropanoids in the other mutants. The genes involved in sinapate ester biosynthesis in Arabidopsis have been described (Fraser et al., 2007; Sinlapadech et al., 2007). No general response of the sinapate ester pathway was observed in the lignin mutants (FIG. 16), showing that this pathway is not responding in an orchestrated way to mutations in the phenylpropanoid pathway. In addition to the phenylpropanoic acids, four benzenoic hexose esters accumulated in the mutants (i.e., benzoyl, p-hydroxybenzoyl, vanilloyl and syringoyl hexose). The exact pathway toward these benzenoids is currently unknown, but these compounds are known to be derived from the corresponding phenylpropanoid acids and/or CoA-esters (Jarvis et al., 2000; Hertweck et al., 2001; Boatright et al., 2004). The accumulation of benzenoids in mutants where the corresponding propanoic acid derivates accumulate, proves that part of the excess of phenylpropanoids is metabolized into C6-C1 compounds.

5.4 Coniferyl Alcohol-Ferulic Acid Dimers

Figure 6:
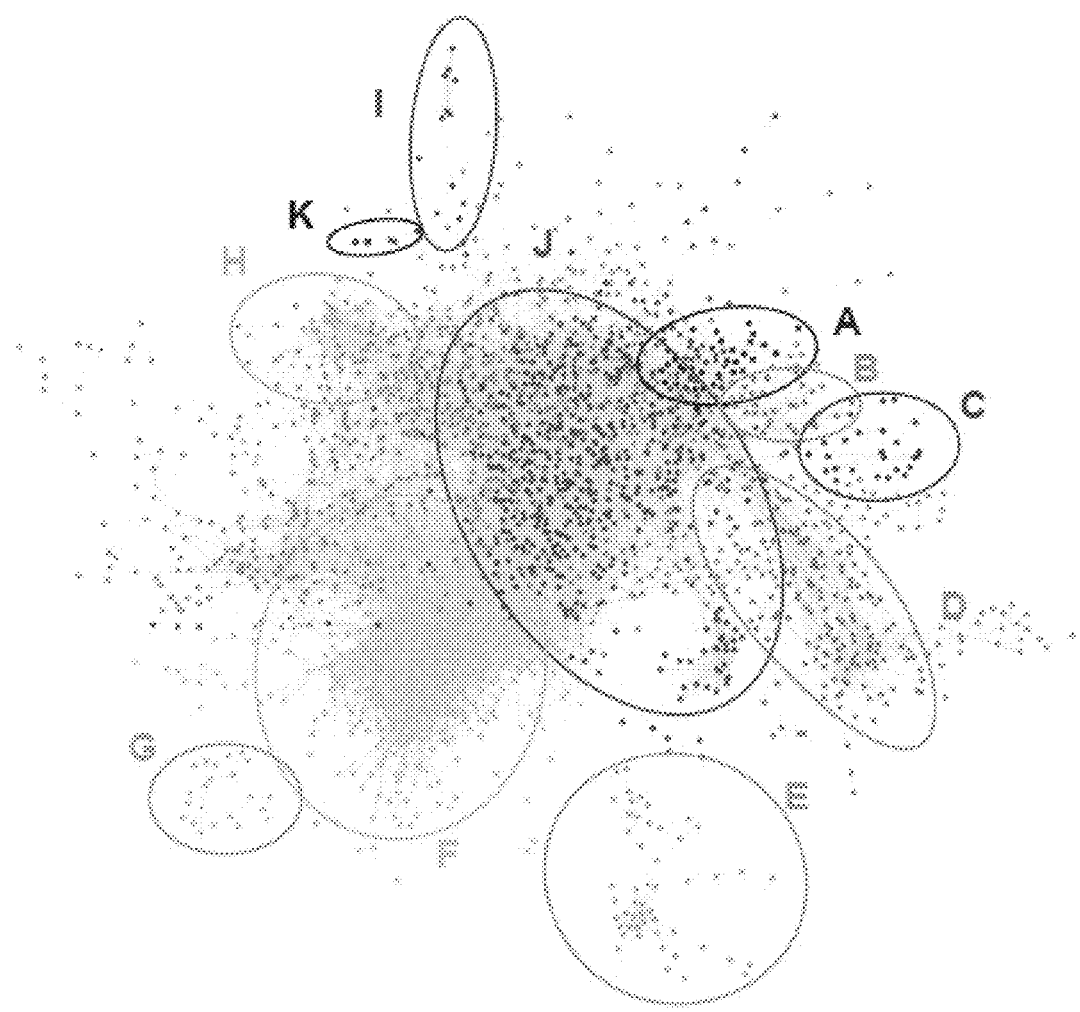
FIG. 6: The Pearson correlation network based on the abundance profiles of transcripts and metabolites in mutants and WT 24 cm. Each node (dot) represents a probe or a metabolite. Each edge (line) represents a positive or negative correlation between the linked pair of nodes. The network is visualized with the organic layout in Cytoscape (Shannon et al., 2003), which requires that highly interconnected groups of nodes (that might be considered as subnetworks) are located in the same region. Nodes with the same color belong to the same subnetwork, according to HCCA clustering (Mutwil et al., 2010) and have a significant enrichment for certain GO-classes (according to BiNGO) (Maere et al., 2005).

Another class of phenylpropanoic acid-derived metabolites in WT Arabidopsis stems comprises coupling products of coniferyl alcohol and ferulic acid (i.e., G(8-O-4)ferulic acid) and different hexosylated derivatives (Rohde et al., 2004) (FIG. 1). Similar to other coniferyl alcohol-derived metabolites, the abundance of coniferyl alcohol-ferulic acid dimers was reduced in c4h, 4cl1, ccoaomt1 and ccr1 mutants and increased in f5h1 and comt mutants. The caffeic acid analogue of G(8-O-4)feruloyl hexose (i.e., G(8-O-4)caffeoyl hexose) accumulated in both ccoaomt1 and comt mutants (FIG. 6). On the other hand, 5-hydroxyferulic acid analogues of G(8-O-4)feruloyl hexose (e.g., G(8-O-4)5-hydroxyferuloyl hexose) were unique to comt mutants (as all 5-hydroxy substituted phenylpropanoids) (FIGS. 5A-5G). These observations further support the involvement of COMT in the O-3 methylation of caffeoyl-CoA and caffeic acid, even in the presence of CCoAOMT1, and the lack of significant involvement of CCoAOMT1 in the O-5 methylation of 5-hydroxyconiferaldehyde in the presence of COMT (Do et al., 2007).

6. System-Wide Responses: The Correlation Network

Figure 7:
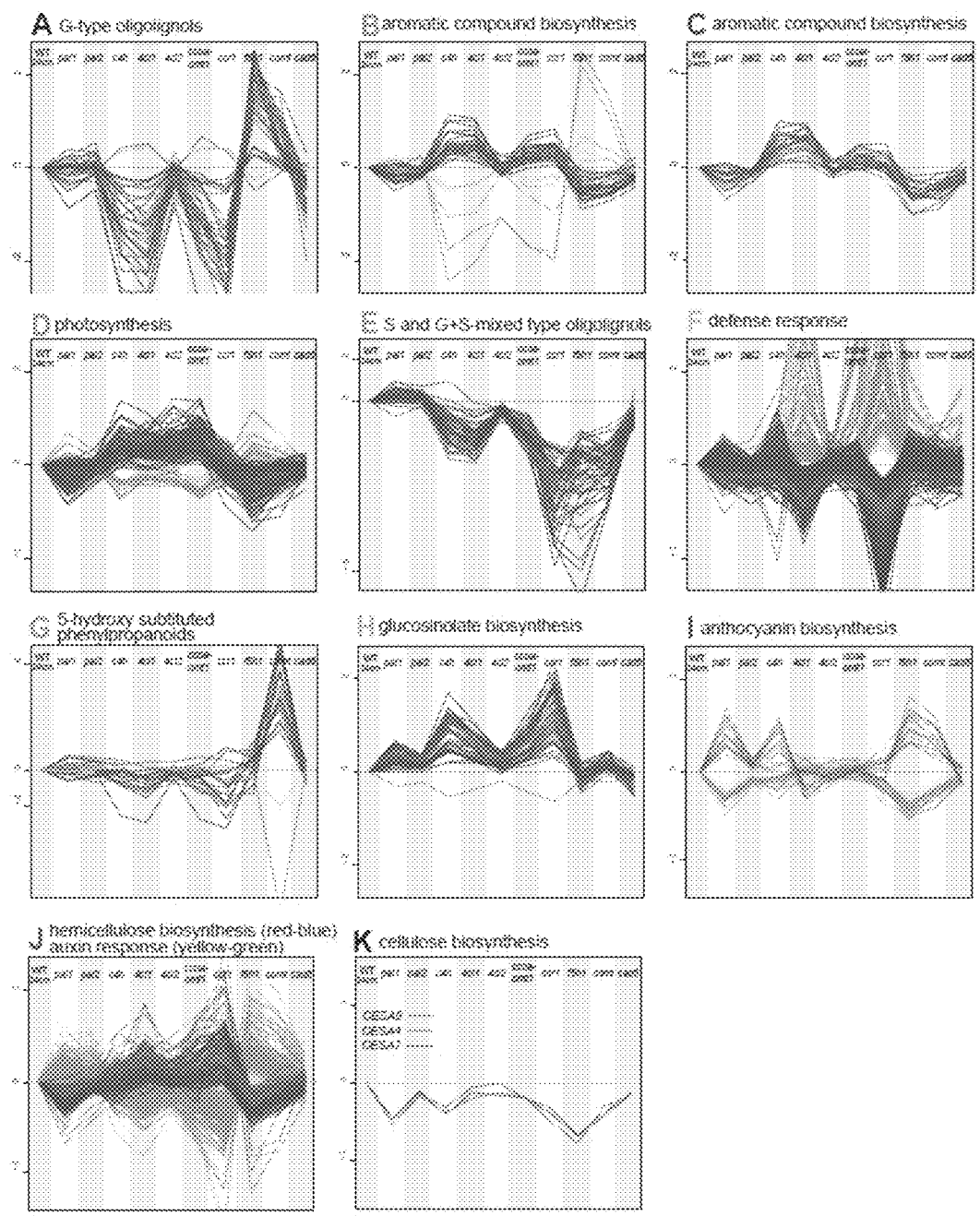
FIG. 7: Abundance profiles of transcripts and metabolites in the subnetworks A-J from the Pearson correlation network in FIG. 6. Color-code of letters A to J is consistent with FIG. 6. The two groups of profiles that were negatively correlated with each other, but part of the same subnetwork, are indicated in contrasting colors (i.e., red-blue and yellow-green). The names above the profiles of the nodes within each subnetwork refer to the most significant GO-class in the case of transcript, or to the metabolic class in the case of compounds. Unless otherwise indicated, a significant enrichment was only found for the red-blue profiles. (K) The expression profile of genes coding for the three subunits of cellulose synthases involved in secondary cell wall formation.
Figure 8:
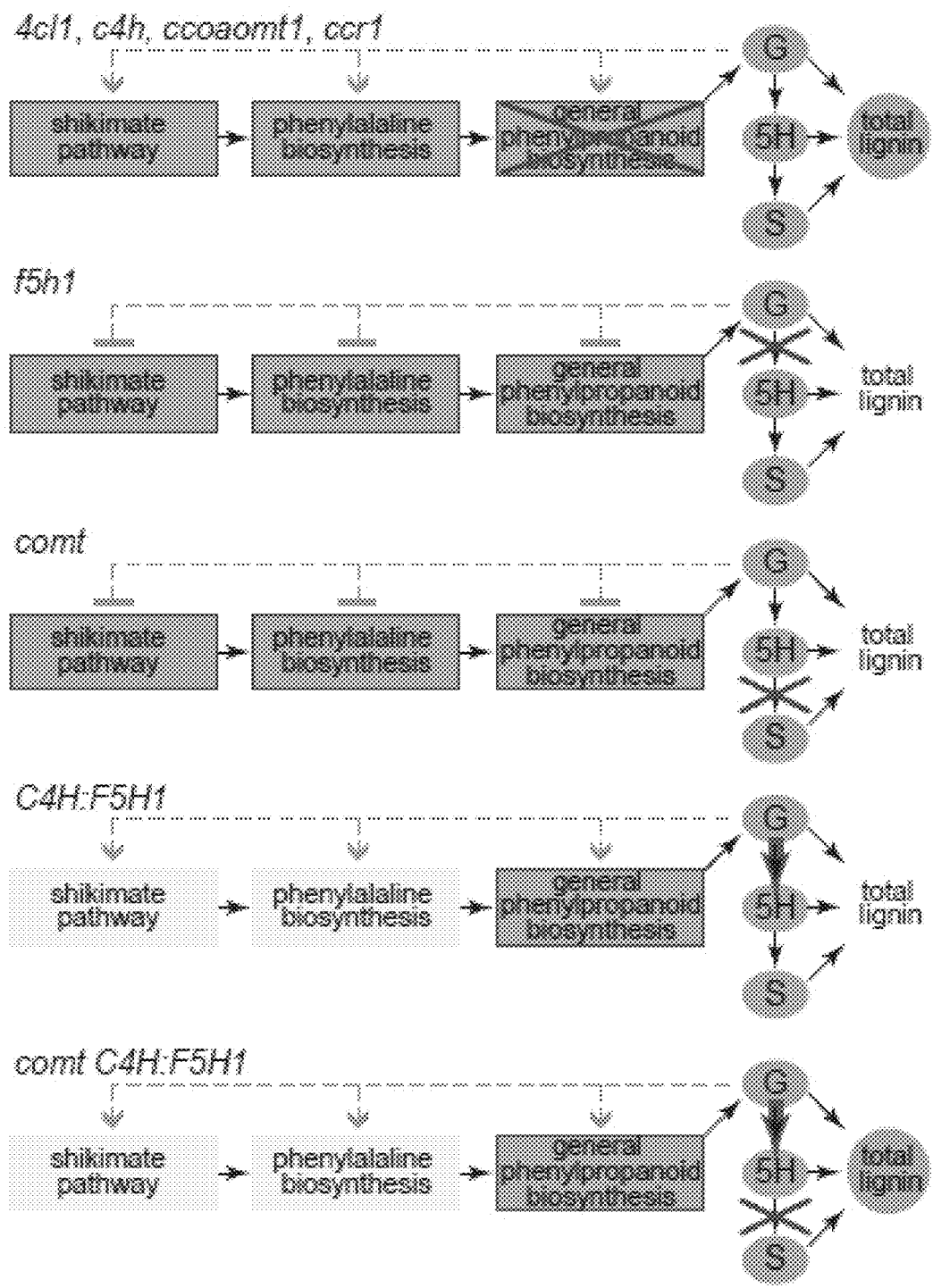
FIG. 8: Schematic overview of transcriptional regulation in different *Arabidopsis* lines with altered monolignol biosynthesis. Black arrows depict the metabolic conversions. Gray dotted-lines denote feedback regulation and a blue cross or red arrow represents knock-out or overexpression of genes, respectively. Transcript abundances of genes are represented by framed boxes, whereas monolignol and lignin abundance is represented by unframed ellipses. As for gene expression, red and blue point toward higher and lower abundances, respectively. White stands for no difference, and grey is unknown. Data of C4H:F5H1 and comt C4H:F5H1 are from Vanholme et al. (2010c).

The results described above indicate that perturbation of the lignin biosynthetic pathway has profound effects on the transcript and metabolite levels of this pathway. However, the consequences of the perturbations reach much further than the perturbed pathway itself. A transcript-metabolite correlation network was constructed to visualize these system-wide consequences. In such a network, transcripts and metabolites (nodes) are linked (edges), if the correlation of their abundance was significant. Two nodes that are significantly correlated are likely to have a common in vivo role (e.g., two genes involved in the same metabolic pathway) (Saito et al., 2008; Vandepoele et al., 2009; Lee et al., 2010). The transcript-metabolite correlation network was based on 3,327 probes (12.67% of the PCGs on the array) and 518 compounds that were significantly different in at least one of the mutant lines (see material and methods for details). The visualization in Cytoscape (Shannon et al., 2003) revealed that these probes and compounds belonged to different independent networks that consisted of 2,778 nodes and 28,206 edges. 2,381 of the nodes were connected in one large network with 27,753 edges (FIG. 6). To obtain further insight into the sub-structure of the correlation network, graph-based HCCA clustering was used (Mutwil et al., 2010) to allocate nodes in the network to certain subnetworks (alias clusters), according to their connectivity and thus their relative profile (FIGS. 6 and 7). The GO-enrichment of genes in each of these clusters was determined via BiNGO (FIG. 7) (Maere et al., 2005). Two subnetworks enriched in aromatic compound biosynthesis (subnetworks B and C) contained several phenylpropanoid and shikimate pathway genes and genes involved in supplying the methyl-donor S-adenosyl methionine (FIGS. 17A and 17B). Several genes involved in hemicellulose (mainly glucuronoxylan) biosynthesis were clustered independently (subnetwork J) from phenylpropanoid biosynthetic genes. Cellulose synthase 7 (CESA8, At4g18780), coding for one of the three sub-units of the cellulose synthase complex involved in secondary cell wall cellulose biosynthesis, had a profile (subnetwork I) that was different from both hemicellulose and phenylpropanoid biosynthetic genes. Two other genes that are involved in secondary cell wall cellulose biosynthesis (CESA4, At5g44030 and CESA7, At5g17420) were correlated with each other (profiles K), but not with any other gene, according to the stringent criteria used to construct the correlation network. Taken together, lignin, cellulose and hemicelluloses biosynthesis appeared to respond differently to the perturbations, implying that their biosynthetic response to lignin perturbation is largely differentially regulated. Genes involved in photosynthesis were up-regulated in c4h, 4cl1, 4c12 and ccoaomt1 mutants and slightly down-regulated in pal1, f5h1-2 and comt mutants (subnetwork D). The transcript levels of genes classified as defense response-related by GO annotation were down in 4cl1 and ccr1 mutants but not differential in the other lignin mutants (subnetwork F). Furthermore, transcripts of the glucosinolate biosynthesis genes were more abundant in the low-lignin c4h, 4cl1, ccoaomt1 and ccr1 mutants, whereas transcripts of anthocyanin biosynthesis genes were up in pal1, c4h, f5h1 and comt mutants (subnetworks H and I). Interestingly, subnetwork J was enriched for auxin-response genes; transcripts of many AUX/IAA and ARF genes were less abundant in c4h, 4cl1, ccoaomt1 and ccr1, and higher in pal1 and f5h1. In addition, almost all amino acids were represented in the large network and, strikingly, most were higher in abundance in the mutants that had reduced lignin levels, i.e., c4h, 4cl1, ccoaomt1 and ccr1. Besides the subnetworks in the large network, some smaller networks were also found, with metabolites and transcripts that were specifically differential in particular mutants. For instance, one small network of 15 nodes contained metabolites that were increased in abundance in the c4h mutants: cinnamic acid, cinnamoyl malate, cinnamoyl glucose and a number of currently unknown molecules that were below the detection limit in WT plants (data not shown). Furthermore, network G was composed of 5-hydroxy substituted phenylpropanoids, which were only detected in comt mutants. Not unexpectedly, the only gene in the network with an opposite profile appeared to be COMT. Clearly, the impact of a mutation in a gene of the lignin biosynthetic pathway was often more dramatic than expected from the visible phenotype and had more far-reaching consequences than those within the lignin pathway itself.

7. Low Lignin Mutants do not have More Cellulose

The correlation network described above suggested that cellulose biosynthesis genes were not up-regulated in any of the mutants. This was surprising as it has been proposed that a lack of lignin is compensated for by an increase in cellulose (see discussion). This compensation would require an increase in transcript levels of genes involved in cellulose biosynthesis, a higher translation or passive biosynthesis, in which case, the protein is not rate-limiting. In contrast to expected, transcript levels of genes involved in secondary cell wall cellulose biosynthesis were reduced in c4h, 4cl1, ccoaomt1 and ccr1 mutants (FIG. 7, Panel K). In addition, the reduction was also prominent in pal1, f5h1 and comt mutants that have no reductions in lignin. To further investigate the relationship between lignin and cellulose, cellulose measurements were performed on developing stems of the same set of lignin mutants and demonstrated a significant reduction in cellulose in ccr1, f5h1 and comt mutants, but no change in the other mutants; similar results were obtained for senesced stems (Van Acker et al., unpublished). Thus, reduced lignin biosynthesis in the low-lignin mutants is not compensated for by increased cellulose biosynthesis.

8. A Surprising Role for Transaldolase Enzymes in Lignification

Figure 9:
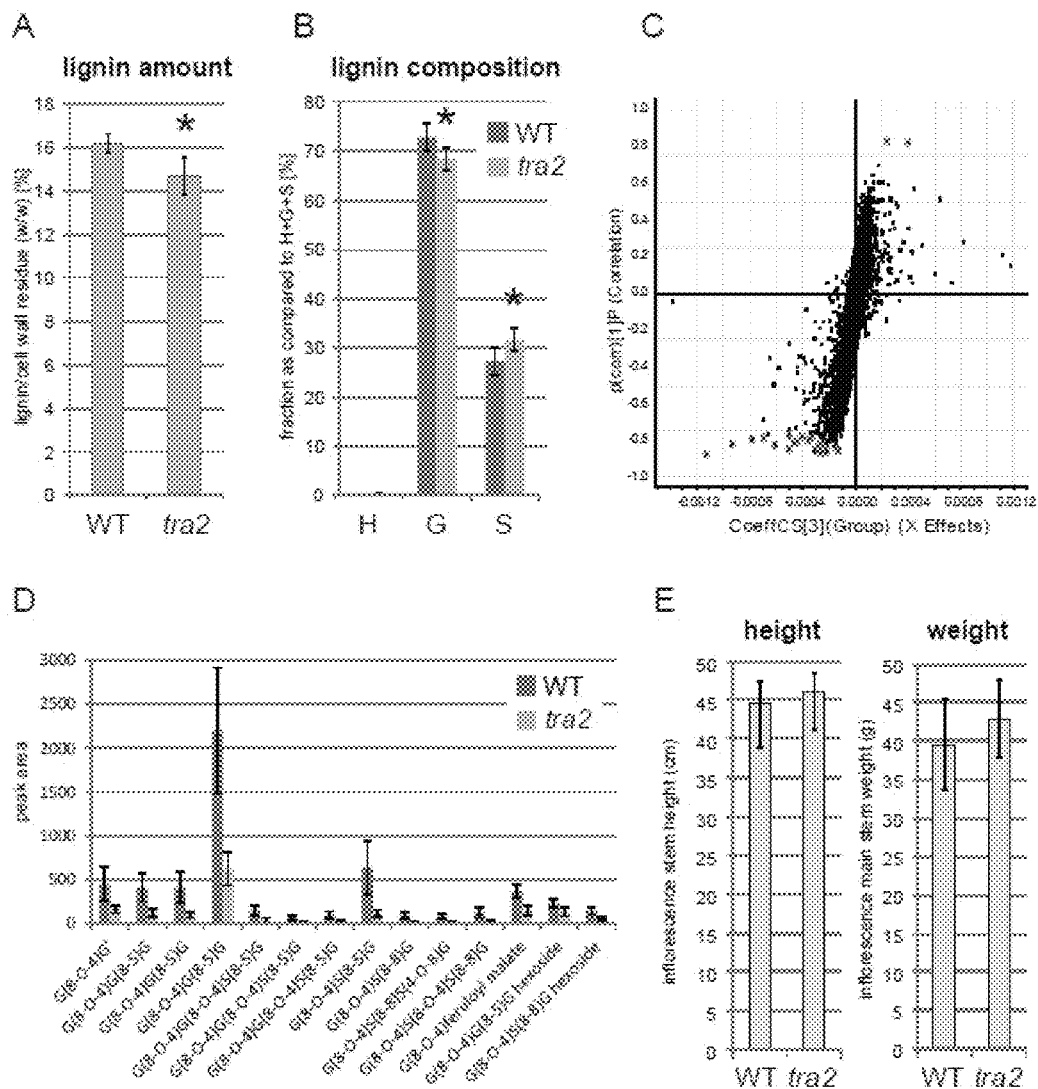
FIG. 9: Reverse genetics suggests a role for TRANSALDOLASE2 (At5g13420) in lignification. (A) Acetyl bromide lignin is reduced by about 15% in tra2 (n=6) as compared to WT (n=6, statistically significant difference p<0.005). (B) Thioacidolysis revealed an increase in S units at the expense of G units in tra2 compared to WT (n=6; statistically significant difference p<0.05). (C) An S-plot was used to highlight the phenolic differences between tra2 (n=12) and WT (n=9). Twenty one m/z peaks were decreased in tra2 as compared to WT (red squares) whereas two m/z peaks were increased (blue squares). (D) Of the 21 compounds that were decreased, 11 could be tentatively identified as oligolignols, 2 as oligolignol hexosides and 1 as G(8-5)feruloyl malate based on their MS2 fragmentation spectra. The other differential peaks could not be identified. (E) No significant differences could be observed in height or weight between the main inflorescence stem of tra2 and WT (n=15).

Based on the guilt-by-association principle as defined by Saito et al. (2008), the co-expression network provides candidate genes that might encode enzymes active in the general phenylpropanoid or closely related pathways. Indeed, the fact that transcript levels of genes involved in the shikimate and methyl-donor biosynthesis pathways were correlated with transcript levels of genes in the phenylpropanoid pathway, provides an intrinsic proof that the methodology used is suitable for the selection of novel candidate genes (FIGS. 17A and 17B). Therefore, a set of candidate genes was selected from the network that were not yet described to be involved in phenolic biosynthesis (FIGS. 17A and 17B). For instance, the two genes annotated as aspartate aminotransferases (ASP4, At1g62800 and AAT, At2g22250) are likely involved in the aminotransferase step in phenylpropanoid biosynthesis, with aspartate as amino group donor and prephenate as amino group acceptor. For AAT, this is in line with its recent in vitro characterization (Graindorge et al., 2010). Two chloroplast-located transporters (PHT4; 2, At2g38060 and PHT2; 1, At3g26570) might be involved in translocating intermediates of the shikimate and phenylalanine biosynthesis (e.g., phospoenolpyruvate, shikimate and phenylalanine) across the chloroplast membrane (Grace and Logan, 2000; Versaw and Harrison, 2002; Guo et al., 2008). Other genes that were highly co-expressed with known phenylpropanoid genes and for which the homology-based nomenclature suggests a role in phenolic metabolism were annotated as enolase (At1g74030), α/β-hydrolase (At1g19190, At4g18550), lipase/acylhydrolases (At1g09390 and At1g28610), chalcone-flavanone isomerase (CHI, At5g05270), enoyl-CoA hydratase/crotonase (At1g06550), transaldolase (At5g13420), two dehydrogenases (At5g24760, At3g19450) and a lysophospholipase (At1g52760). In addition, transcription factors identified here as being co-expressed with genes of the general phenylpropanoid and related pathways are good candidates for regulating these pathways. For example, the co-expressed MYB58 (At1g16490) is already known as a transcriptional activator of lignin biosynthesis in the SND1-mediated transcriptional network-regulating secondary cell wall formation (Zhong et al., 2008; Zhou et al., 2009). However, MYB123 (At5g35550) has been described as a master regulator of proanthocyanidin biosynthesis (Debeaujon et al., 2003; Sharma and Dixon, 2005) but the data showing co-expression with genes involved in general phenylpropanoid biosynthesis rather than proanthocyanidin biosynthesis suggests a more general role. For several genes such as a CCCH-type zinc finger (At1g66810) and WUSCHEL-related Homeobox 4 (WOX4, At1g46480), the connection with aromatic metabolism is as yet unclear. Reverse genetics is needed to reveal whether all of these co-expressed genes really play a role in aromatic metabolism. The knock-out mutant (T-DNA insertion mutant of *A. thaliana*) of the candidate gene TRANSALDOLASE 2 (At5g13420), identified as tra2, was investigated. The senesced inflorescence stem of tra2 had reduced acetyl bromide lignin levels and an increased S/G ratio (see FIG. 9). In addition, phenolic profiling of developing inflorescence stems showed that the levels of oligolignols were reduced (see FIG. 9). These data show a convincing role for TRANSALDOLASE 2 in the (flux toward) phenolic metabolism, thus supporting the value of the correlation-network approach to discovering genes involved in lignification. *Arabidopsis* has two transaldolase isoforms that share low sequence similarity (Caillau and Quick, 2005). Both transaldolases catalyze a plastid localized reaction of the non-oxidative branch of the oxidative pentose phosphate pathway (OPPP), which gives rise to erythrose-4-phosphate, a precursor of the shikimate pathway (Kruger and von Schaewen, 2003). The OPPP has a central role in both primary and secondary metabolism (Caillau and Quick, 2005) that has been illustrated by the effects on photosynthesis, sugar levels and phenolic compounds provoked by disturbing the flux through this pathway in tobacco (Henkes et al., 2001). Strikingly, although this enzyme acts at an early stage in the supply of shikimate pathway precursors, lignin amount and oligolignol levels were reduced in tra2, whereas no growth abnormalities were seen (see FIG. 9, panel E—indeed height and weight were as the wild-type, which indicates that there is no yield penalty associated with the tra2 mutant lines, as is often the case in other lignin mutant plants).

Figure 10:
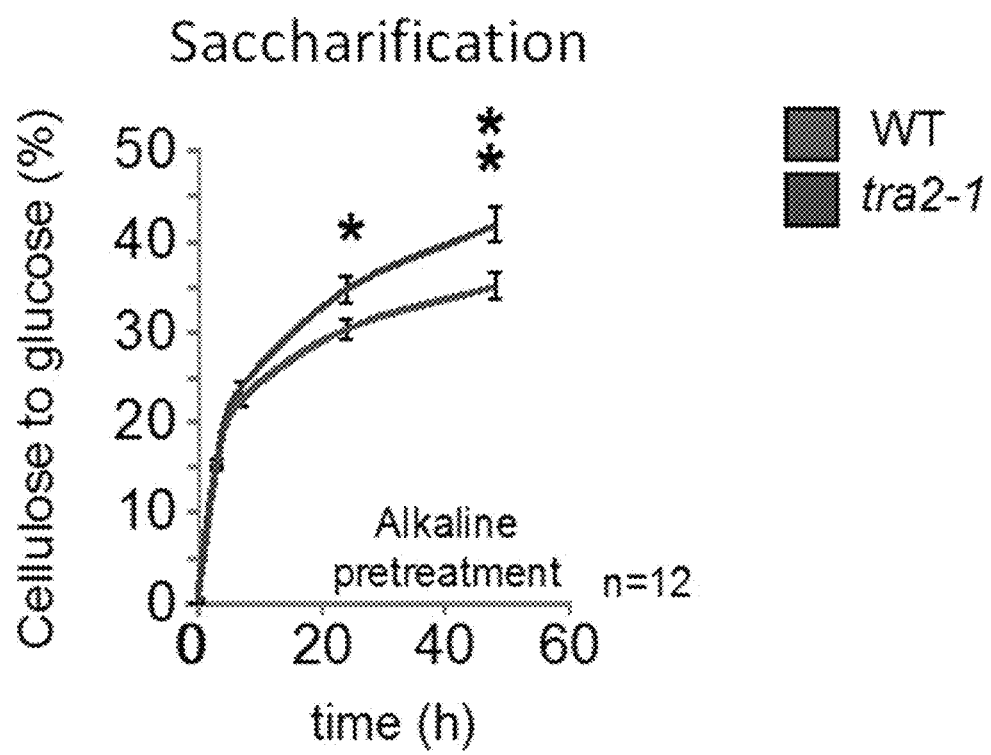
FIG. 10: It is shown that the tra2-1 mutant stems release 20% more glucose, as compared to wild-type, upon saccharification over 48 hours. The upper line in the figure depicts the amounts of glucose of the tra2-1 mutant, while the lower line depicts the wild-type (wt) data. The data have been generated with samples from 12 plants (n=12).

It was shown that after alkaline pretreatment, the tra2 mutant stems released 20% more glucose as compared to WT upon saccharification over 48 hours (see FIG. 10).

9. Analysis of the *A. thaliana* Double Mutant Transaldolase 2 KO-COMT KO

The comt1 tra2-1 line was generated with cross-pollination, whereafter, the dry siliques was collected and the seeds were regrown. The zygosity of the plants was confirmed with PCR. The seeds from the double heterozygote plants were harvested and these plants were grown. Again, the zygosity was confirmed and the plants were left to scenes and the double homozygous mutants dry stems as well as the plants only homozygous for the parental lines were selected for lignin quantification and saccharification.

It was shown that lignin was reduced in the comt tra2-1 mutant as compared to each of its parental lines (i.e., comt and tra2-1 mutants), see FIG. 11, Panel A.

The saccharification improved in the comt tra2 double mutant. The latter shows a synergistic effect when combining comt and tra2, see FIG. 11, Panel B, for the improved saccharification.

10. Promoter Sequences Used in the Construction of the Chimeric Genes of the Disclosure An example of a fiber-specific promoter that can be used in the context of the disclosure is the NST1/ANAC043-promoter (derived from the *Arabidopsis thaliana* entry At2g46770) and is depicted in SEQ ID NO:25.

A second example of a fiber-specific promoter that can be used in the context of the disclosure is the SND1/NST3/ANAC043-promoter (derived from the *Arabidopsis thaliana* entry At1g32770) and is depicted in SEQ ID NO:26.

An example of a vessel-specific promoter that can be used in the context of the disclosure is the VND6/ANAC101 promoter (derived from the *Arabidopsis thaliana* entry AT5G62380) and is depicted in SEQ ID NO:27.

A second example of a vessel-specific promoter that can be used in the context of the disclosure is the VND7/ANAC030 promoter (derived from the *Arabidopsis thaliana* entry AT1G71930) and is depicted in SEQ ID NO:28.

11. Orthologous Genes of the *Arabidopsis thaliana* Transaldolase Genes Present in Crops Using PLAZA 2.5 (available via the world wide web at bioinformatics.psb.ugent.be/plaza/), orthologous gene families of transaldolase have been identified in different plant species.

SEQ ID NO:1 depicts the *Arabidopsis thaliana* TRANSALDOLASE 2 (At5g13420) gene and SEQ ID NO:2 its corresponding amino acid sequence.

SEQ ID NO:3 depicts the *Arabidopsis thaliana* TRANSALDOLASE 1 (AT1G12230) gene and SEQ ID NO:4 its corresponding amino acid sequence.

SEQ ID NO:5 depicts the *Populus trichocarpa* AtTRANSALDOLASE 2 homolog #1 (PT01G12740) gene and its corresponding amino acid sequence is depicted in SEQ ID NO:6.

SEQ ID NO:7 depicts the *Populus trichocarpa* AtTRANSALDOLASE 2 homolog #2 (PT03G15080) and SEQ ID NO:8 depicts its corresponding amino acid sequence.

SEQ ID NO:9 depicts the *Oryza sativa* ssp. indica AtTRANSALDOLASE 2 homolog #1 (OSINDICA_01G66340) gene and SEQ ID NO:10 depicts its corresponding amino acid sequence.

SEQ ID NO:11 depicts the *Oryza sativa* ssp. indica AtTRANSALDOLASE 2 homolog #2 (OSINDICA_01G66360) gene and SEQ ID NO:12 depicts its corresponding amino acid sequence.

SEQ ID NO:13 depicts the *Zea Maize* AtTRANSALDOLASE 2 homolog #1 (ZM03G22330) nucleotide sequence and SEQ ID NO:14 depicts its corresponding amino acid sequence.

SEQ ID NO:15 depicts the *Zea Maize* AtTRANSALDOLASE 2 homolog #2 (ZM08G28550) nucleotide sequence and SEQ ID NO:16 depicts the corresponding amino acid sequence.

SEQ ID NO:17 depicts the *Populus trichocarpa* AtTRANSALDOLASE 1 homolog #1 (PT01G00070) nucleotide sequence and SEQ ID NO:18 depicts its corresponding amino acid sequence.

SEQ ID NO:19 depicts the *Populus trichocarpa* AtTRANSALDOLASE 1 homolog #2 (PT03G10250) nucleotide sequence and SEQ ID NO:20 depicts the corresponding amino acid sequence.

SEQ ID NO:21 depicts the *Oryza sativa* ssp. indica AtTRANSALDOLASE 1 homolog (OSINDICA_08G04630) nucleotide sequence and SEQ ID NO:22 depicts the corresponding amino acid sequence.

SEQ ID NO:23 depicts the *Zea Maize* AtTRANSALDOLASE 1 homolog (ZM04G07650) nucleotide sequence and SEQ ID NO:24 depicts the corresponding amino acid sequence.

12. Generation of Transgenic Plants Having a Down-Regulated Activity of Transaldolase *Arabidopsis thaliana*:

Several chimeric genes are constructed comprising the following elements: promoter (35S promoter or lignin-specific promoter or fiber-specific promoter or vessel-specific promoter), operably linked to an RNAi construct with specificity for the transaldolase 1 or 2 and a terminator. The resulting chimeric genes are incorporated in an *Arabidopsis thaliana* transformation vector and *A. thaliana* transformed plants are obtained. Cell wall (cellulose content, lignin composition and content, saccharification ability . . . ) are obtained and analyzed. Plant growth and development of the *Arabidopsis* line with reduced transaldolase expression is monitored.

In a next step, the effect on cell wall composition and plant development is monitored in double transformants of *Arabidopsis transaldolase1×transaldolase2*.

In a further step, the reduced transaldolase 1 or transaldolase 2 (or combined activity) is combined with other genetic modifications (mutations or transgenics) with improved saccharification (e.g., lignin mutants as comt, 4cl1 and c4h).

Poplar and Corn:

The effect on cell wall and plant growth and development of the down-regulation of transaldolase orthologs in poplar and corn are currently being investigated, which are relevant species for bio-fuel applications.

Materials and Methods
Plant Lines c4h-2 (ref3-2), c4h-3 (ref3-3) and f5h1-2 (fah1-2) are ethylmethane sulfonate (EMS)-generated mutants (Chapple et al., 1992; Meyer et al., 1996; Ruegger et al., 1999; Ruegger and Chapple, 2001; Schilmiller et al., 2009). Following T-DNA insertional mutants from SALK (Alonso et al., 2003), GABI-Kat (Rosso et al., 2003), SM/SLAT (Tissier et al., 1999) and SAIL collection (Sessions et al., 2002) were ordered via the European *Arabidopsis* Stock Centre (NASC): pal1-2 and -3, pal2-2 and -3, 4cl1-1 and -2, 4cl2-1, ccoaomt1-3, comt-1 and -4, f5h1-4, cad6-1 and -4, ccr1-6 and tra2 (in particular, the tra2-1 line SALK_094724). The mutants 4cl2-3 and ccoaomt1-5 were delivered as homozygotes by the GABI-Kat project. ccoaomt1-3, ccr1-3 (ccr1s) and ccr1-6 (ccr1g) were provided by Lise Jouanin as homozygous seed stocks (Mir Derikvand et al., 2008; Ruel et al., 2009). In case of c4h-2, segregating seed stocks of a heterozygous parental line were kept, due to sterility of the homozygous plant.

Growth Conditions

Plants (mutant lines and wild-type) were germinated on soil (Saniflor ref. 252020) supplemented with 10% (volume) vermiculite. All plants (except, for example, 9) were grown for 8 weeks in short day conditions (9 hours light/15 hours dark) and thereafter transferred to long day conditions (3 months). Plant experiments as outlined in Example 9 were carried out on plants that grew entirely on long day conditions until fully scenesced (approximately 4 months).

Biological Material

Inflorescence stems were flash-frozen in liquid nitrogen. The basal 1-9 cm of individual inflorescences was ground in 2 ml Eppendorf tubes using a Retsch mill (20 Hz, 5 mm bead). For metabolite profiling, 10 to 13 stems of each genotype/developmental stage were used individually. For microarray analysis, aliquots of minimum eight different samples of the same genotype/developmental stage were pooled to obtain one biological sample. For each genotype/developmental stage, two biological replicas were prepared for microarray analysis.

Metabolite Extraction

For each mutant and WT developmental stage, ground plant material was individually extracted with 500 µl MeOH (15 minutes, 70° C., 1000 rpm), containing internal standards (o-anisic acid, 2.4 mg/l; 4-hydroxyphenyl-2-butanon, 6 mg/l; methyl-5-acetylsalicylate, 10 mg/l; methyl nonadecanoate, 16 mg/l). The cooled extract was loaded on a 60 mg Varian Bond Elut Plexa™ (PS-DVB) column, pre-equilibrated with MeOH and subsequently washed with 400 µl MeOH. The combined phases were split into 200 µl for GC-MS analysis and 700 µl for UPLC-MS analysis. Both fractions were freeze-dried.

UPLC-MS Analysis

Samples were re-dissolved in 80 µl water and transferred to an injection vial. 15 µl of each sample was injected on a Waters Acquity UPLC® system equipped with an Acquity UPLC BEH C18 (2.1×100 mm, 1.7 µm) column. A gradient of two buffers was used: buffer A (100/1/0.1 $H_2O$/ACN/ammonium acetate (2M) pH5), buffer B (100/1/0.1 ACN/$H_2O$/ammonium acetate (2M) pH5); 95% A for 0.1 minute decreased to 55% A in 36.9 minutes (200 µl/minute, column temperature 40° C.). An UV/Vis absorption spectrum was measured (190-600 nm). Atmospheric Pressure Chemical Ionization, in the negative ionization mode, was used to couple UPLC with the ion trap MS instrument (LCQ Classic; ThermoQuest, vaporizer temperature 450° C., capillary temperature 150° C., source current 5 mA, sheath gas flow 21, aux gas flow 3, mass range 135-1000 amu).

Peaks were integrated and aligned using the MetAlign software (available on the world wide web at pri.wur.nl/UK/products/MetAlign; Lommen (2009)), with the following parameters: retention begin=1, retention end=2500, max amplitude=$10^9$, peak slope factor=1.0, peak threshold factor=1.5, average peak width at half height=10, no scaling, begin of $1^{st}$ region=0 (max shift 40), end of $1^{st}$ Region=2800 (max shift 60), no pre-align processing. In MS Excel®, peaks that were not present in all biological replicates of at least one single mutant were removed. Also the front signal (<3 minutes) was removed. Based on retention time and the intensity, an in-house R script grouped peaks that were derived from the same compound. The final list of compounds was manually correct. For phenolic profiling of the tra2 mutant and the targeted analysis of caffeoyl glucose and caffeoylmalate, similar buffers were used as above, but with 0.1 formic acid (pH2) instead of ammonium acetate. Separation was done as above on a Waters Acquity UPLC® system, but coupled to a Synapt Q-Tof™ (Waters Corporation, Milford, Mass., USA). For accurate mass data, one sample of each genotype and developmental stage was injected and analyzed via UPLC-Fourier Transform-Ion Cyclotron-MS (FT-ICR-MS; LTQ FT Ultra, Thermo Electron Corporation, Bremen, Germany) with ElectroSpray™ Ionization (ESI) in the negative mode according to Morreel et al. (2010a), but with 0.1 acetic acid (pH4) in buffers A and B instead of formic acid.

GC-MS Analysis

A procedure adapted from Roessner et al. (2000), was used. Samples were successively derivatized by methoxyamine hydrochloride (Meox) and N-Methyl-N-(trimethylsilyl)trifluoroacetamide (MSTFA): 40 µl Meox solution (48 mg Meox in 2.4 ml pyridine) was added to the dried extracts, and the samples were incubated for 1.5 hours at 30° C. 45 µl MSTFA mix (2400 µl MSTFA+300 µl alkane mixture) was added, and the samples were incubated for another 0.5 hours at 37° C. One µl was splitless injected in a HP6890 GC. Inlet temperature: 230° C. A constant He flow (1 ml/minute) was used on the Varian FactorFour™ capillary Column VF-5 ms (5% phenyl, 95% dimethylpolysiloxane). Oven temperature: 70° C. for the first 5 minutes, increased with 5° C./minute to 325° C. and kept for 1 minute. The HP5973 quadrupole mass detector coupled to the GC-performed EI ionization (60-600 amu; 7.8-68.8 minute). Integration and alignment was performed using the R×cms package (Smith et al., 2006) with following parameters for the integration: fwhm=3, max=300, snthresh=3, step=0.1, steps=2, mzdiff=0.5; and for the alignment: bw=2, minfac=0.3, max=300. Peakfilling was used. In MS Excel, peaks were manually curated. Peaks were manually annotated by use of the GMD@CSB.DB-library from the Max-Planck Institute for Plant Physiology (Golm, Germany) (Stein, 1999; Kopka et al., 2005) and AMDIS software (Davies, 1998).

RNA Isolation

Total RNA was prepared from 100 mg ground plant material (see "Biological Material") using the mirVana™ miRNA Isolation Kit (Ambion), recovering a fraction of miRNA, and a fraction of total RNA (200 bp cut off).

Microarray Design

Two-color full genome Agilent *Arabidopsis* 3 oligo arrays were used. These contain 32,221 unique probes, representing 25,094 genes. The MicroArray Quality Control (MAQC) consortium reported several times the good quality of the Agilent two-color arrays (Kuo et al., 2006; Patterson et al., 2006; Shi et al., 2006b). The transcripts of two independent biological replicates (pools; see "Biological Material") of 20 mutants and 4 WT developmental stages were measured. Each pool was measured twice (once Cy3- and once Cy5-labeled), except for WT 24 cm and WT 32 cm, which were measured six times. The samples were hybridized in two sets, both contained the two biological replicates of WT 24 cm, WT 32 cm and of one mutant allele for each gene of interest. The first set was further extended with the replicates of WT 8 cm and WT 16 cm. Preparation and labeling of the samples, hybridization, washing, scanning, and feature extraction of Agilent 60-mer oligonucleotide microarrays was conducted at the VIB Microarray Facility and conducted according to the manufacturer's instructions (Agilent).

Statistics Growth

The height of plants in the eight trays was measured daily. Two replicates of each mutant and 10 replicates of WT were grown in each tray. Data was analyzed with longitudinal statistics in R (version 2.6.2.). Data from 4 until 12 days was used to detect lines with different growth rate. For the covariance, an autoregressive structure with heterogeneity was chosen based on the Akaike information criterion (AIC); gls(height~time+line+time:line, correlation=corAR1 (form=~1 line), weights=varIdent(form=~1|T), data=data, na.action=na.exclude). Data from 27 until 44 days was used to detect lines with different final height. Again, based on AIC, an autoregressive structure fitted best, the following command was used: gls(height~time~line, correlation=corAR1 (form=~1|line), data=data, na.action=na.exclude). The Benjamini and Hochberg multiple test correction was calculated with the function mt.rawp2adjp(proc="BH") in the package multtest.

Microarray Analysis: Linear Mixed Model

For each array, standard Pearson correlations were calculated between background $\log_2$ ratios and foreground $\log_2$ ratios (Scharpf et al., 2007). Subsequently, Loess normalization was performed on $\log_2$ transformed signals using the SAS Loess procedure (v9.1.2). Loess normalized expression data was further analyzed using two interconnected ANOVA models according to Wolfinger et al. (2001). The SAS proc mixed procedure was used to fit the parameters. The normalization model was:

$$y_{gijklm} = \mu + L_m + A_i(L_m) + r_{gijklm}$$

where $y_{gijklm}$ is the $\log_2$ of the Loess normalized intensity measurements of probe g, array i, dye j, variety k, biological replicate l and loop m. $\mu$ represents an overall mean value, L is the (fixed) main loop effect, A is the (random) effect for arrays, nested within loop, and r is the error. $A_i(L_m)$ and $r_{gijklm}$ are assumed to be normally distributed random variables with zero and to be independent both across their indices and with each other. A random interaction effect between dye and array and a fixed main dye effect were left out of the model after testing the significance with a likelihood ratio test (LRT) and an F-test, respectively. The model adopted at the probe level was:

$$r_{ijklm} = \mu' + L_m + A_i(L_m) + V_k(L_m) + D_j + B_l(V_k) + \varepsilon_{ijklm}$$

where $\mu'$ represents the mean value per probe, L the probe-specific loop effect, A the probe-specific array effects reflecting the spot-to-spot variability inherent in spotted microarray data, D the probe-specific dye effects, V the probe-specific variety effects, nested under loop and B the probe-specific replicate effects, nested under variety. $A_i(L_m)$, $B_l(V_k)$ and $\varepsilon_{ijklm}$ are assumed to be normally distributed random variables and to be independent both across their indices and with each other. Restricted maximum likelihood (REML) was used to estimate the variance components. For the probe model, type III F-tests and p-values were calculated for the variety terms. The Kenward-Roger method (Kenward and Roger, 1997), recommended by Verbeke and Molenberghs (2009) when sample sizes are small at each level of the data set, was used to calculate denominator degrees of freedom for these approximate F-tests. False discovery rate (FDR) adjusted p-values, described by Benjamini and Hochberg (1995) were calculated. The estimates of primary interest are those of the variety ($V_k(L_m)$) effects. Differences of the estimates between all mutant lines and WT 24 cm for the variety effects along with mixed-model based t-tests and p-values were calculated for those probes that had a significant FDR adjusted p-value for the F-tests (fdr≤0.01). Given the design, there is a confounding effect between loop and variety. For WT 24 cm and WT 32 cm, two estimates were obtained, one for each loop. Lines from loop 1 were compared to WT 24 cm from loop 1 and lines from loop 2 were compared to WT 24 cm from loop 2.

On those probes that had a significant FDR adjusted p-value for the F-tests (fdr≤0.01), the balanced decision strategy (Moerkerke and Goetghebeur, 2006) was conducted. A target alternative of 1 was chosen for each probe. A probe signal was considered to be significantly differential between a mutant line and WT 24 cm when the R-ratio was >1. A weight ratio of 10 was used. When taking the average of two mutant lines, significances were calculated as follows: all significantly differential probe signals from one line that had a difference in least square means estimates of at least 0.3 in the same direction in the other line were retained as significant differential and vice-versa. The choice of −0.3 and +0.3 corresponds with the $90^{th}$ percentile of the absolute values of all differences in least square means estimates.

GC-MS and UPLC-MS Analysis: Linear Mixed Model

For both GC and UPLC-MS, peaks were normalized to dry weight. The following normalization model was adopted on the combined dataset of GC-MS and UPLC-MS:

$$y_{ijkl} = \mu + R_i + N_j(R_i) + r_{ijkl}$$

where $y_{ijkl}$ is the base-2 logarithm of the normalized peak area of metabolite 1 for run i, number in the run j, and mutant/WT developmental stage (here called variety) k. $\mu$ represents an overall mean value, R is the main run effect, N is the effect for the location in the run, nested within run and $\varepsilon$ the error term. $R_i$, $N_j(R_i)$ and $r_{ijkl}$ are assumed to be normally distributed random variables with zero means and to be independent both across their indices and with each other. The metabolite model is described as follows:

$$r_{ijk} = \mu' + R_i + Loc_j(R_i) + V_k + \gamma_{ijk}$$

where $r_{ijk}$ represents the conditional residual from the previous model, $\mu'$ the mean value per metabolite, R the metabolite-specific run effect, Loc the metabolite-specific effect for the location in the run, nested within run and V the metabolite-specific variety effects. Loc is an interval variable created from position within the run (position 1-9, 10-18, 19-27, 28-36) to avoid overparameterization of the model. $R_i$, $Loc_j(R_i)$ and $\gamma_{ijkl}$ are assumed to be normally distributed random variables with zero means and to be independent, both across their indices and with each other. They have different variances across the metabolite index l. Residual analysis showed many outliers. This was due to incorrect peak identification of the Metalign software, resulting in erroneous zero values. Therefore, all observations with a residual value less than −4 were set to zero, and subsequently estimated with the k-nearest neighbor procedure with k=10 (R package impute.knn). Further analysis including multiple testing correction, calculation of the differences of the least-squares means for the variety effects and balance test was performed as for the microarray analysis.

Hierarchical Clustering of Samples

Hierarchical clustering was performed with Ward's method using the dist and agnes function from the R cluster package. The distance metric used was the Euclidean distance. As input data, the differences in estimates between all lines and WT 24 cm for the significantly differential probes and metabolites were used.

Correlation Network

Because the correlation of profiles was often biased by extremely high or low expression/abundance values in a few mutants with a clear developmental effect (such as c4h-2 and ccr1-3), these samples were left out from the analysis. Despite its aberrant development, the weaker ccr1-6 allele was retained in the sample set to keep information of at least one ccr1 mutant. As the number of samples for c4h and ccr1 mutants was now reduced to one, and since bias toward certain samples during the correlation analysis needs to be avoided, data from the two alleles of all other mutants were merged by taking the average value of each transcript and each metabolite of both alleles. For pal1, pal2, 4cl1, 4cl2, ccoaomt1, comt and cad6 mutants, this was justified by their similarity, as demonstrated by the hierarchical clustering of samples (FIG. 4). As explained in the Supplementary Text online, f5h1-4 was left out. This selection procedure resulted in a set of eleven "samples": the average of both mutant alleles of pal1, pal2, 4cl1, 4cl2, ccoaomt1, comt and cad6, and additionally c4h-3, ccr1-6, f5h1-2 and the reference sample WT 24 cm.

The correlation network was constructed with transcripts and metabolites that were significantly different in at least one of the averaged values of the two mutant alleles of each gene, as compared to WT 24 cm, with the exception of transcripts of the f5h1 mutant, which were used if they were significantly different in f5h1-2 (in total 3,327 probes, 196 GC-MS and 324 UPLC-MS compounds). For those genes that were mutated, the expression in the corresponding mutant was replaced via the k-nearest neighbor procedure with k=10 (R package impute.knn), which led to 10 extra imputed probes. A relevance network was constructed using a statistically sound two-stage co-expression detection algorithm (Zhu et al., 2005). The following parameters were used: FDR α=0.05, minimal acceptable strength 0.7. Two measures of association were considered: the Pearson correlation and the Kendall's tau coefficient. Calculations were done with the R GeneNT package. The complete network was visualized with Cytoscape 2.6.1 bioinformatics software program (organic layout) (Shannon et al. (2003)). Subnetworks were generated by use of HCCA clustering (Mutwil et al., 2010). For BiNGO analysis (Maere et al., 2005), each subcluster was split in two sets (if appropriate) according to their relative expression profile (positively and negatively correlated nodes, respectively). A corrected p-value cutoff of 0.01 was used for enrichment, and the top 11 subclusters are presented in FIGS. 6 and 7.

Cell Wall Analysis

The acetyl bromide protocol published by Dence (1992), optimized for small sample quantities of *Arabidopsis* was used for lignin quantification. Cellulose amount was determined via the sulfuric acid-phenol colorimetric method based on the methods of DuBois et al. (1956) and Masuko et al. (2005).

REFERENCES

Alonso, J. M., Stepanova, A. N., Leisse, T. J., Kim, C. J., Chen, H., Shinn, P., Stevenson, D. K., Zimmerman, J., Barajas, P., Cheuk, R., Gadrinab, C., Heller, C., Jeske, A., Koesema, E., Meyers, C. C., Parker, H., Prednis, L., Ansari, Y., Choy, N., Deen, H., Geralt, M., Hazari, N., Hornm, E., Karnes, M., Mulholland, C., Ndubaku, R., Schmidt, I., Guzman, P., Aguilar-Henonin, L., Schmid, M., Weigel, D., Carter, D. E., Marchand, T., Risseeuw, E., Brogden, D., Zeko, A., Crosby, W. L., Berry, C. C., and Ecker, J. R. (2003). Genome-wide insertional mutagenesis of *Arabidopsis thaliana. Science* 305:653-657.

Baucher, M., Halpin, C., Petit-Conil, M., and Boerjan, W. (2003). Lignin: genetic engineering and impact on pulping. Crit. Rev. Biochem. Mol. 38: 305-350.

Benjamini, Y., and Hochberg, Y. (1995). Controlling the false discovery rate—a practical and powerful approach to multiple testing. J. R. Statist. Soc. Series B Stat. Methodol. 57: 289-300.

Berthet, S., Demont-Caulet, N., Pollet, B., Bidzinski, P., Cézard, L., Le Bris, P., Borrega, N., Hervé, J., Blondet, E., Balzergue, S., Lapierre, C., and Jouanin, L. (2011). Disruption of LACCASE4 and 17 results in tissue-specific alterations to lignification of *Arabidopsis thaliana* stems. Plant Cell 23: 1124-1137.

Boatright, J., Negre, F., Chen, X., Kish, C. M., Wood, B., Peel, G., Orlova, I., Gang, D., Rhodes, D., and Dudareva, N. (2004). Understanding in vivo benzenoid metabolism in *petunia* petal tissue. Plant Physiol. 135: 1993-2011.

Boerjan, W., Ralph, J., and Baucher, M. (2003). Lignin biosynthesis. Annu. Rev. Plant Biol. 54: 519-546.

Bonawitz, N. D., and Chapple, C. (2010). The genetics of lignin biosynthesis: connecting genotype to phenotype. Annu. Rev. Genet. 44: 337-363.

Bracher, P. J., Snyder, P. W., Bohall, B. R., and Whitesides, G. M. (2011). The relative rates of thiol-thioester exchange and hydrolysis for alkyl and aryl thioalkanoates in water. Orig. Life Evol. Biosph. 41: 399-412.

Brown, D. M., Zeef, L. A. H., Ellis, J., Goodacre, R., and Turner, S. R. (2005). Identification of novel genes in *Arabidopsis* involved in secondary cell wall formation using expression profiling and reverse genetics. Plant Cell 17: 2281-2295.

Caillau, M., and Quick, W. P. (2005). New insights into plant transaldolase. Plant J. 43: 1-16.

Caño-Delgado, A., Penfield, S., Smith, C., Catley, M., and Bevan, M. (2003). Reduced cellulose synthesis invokes lignification and defense responses in *Arabidopsis thaliana*. Plant J. 34: 351-362.

Chapple, C. C. S., Vogt, T., Ellis, B. E., and Somerville, C. R. (1992). An *Arabidopsis* mutant defective in the general phenylpropanoid pathway. Plant Cell 4: 1413-1424.

Chen, F., and Dixon, R. A. (2007). Lignin modification improves fermentable sugar yields for biofuel production. Nat. Biotechnol. 25: 759-761.

Chen, F., Srinivasa Reddy, M. S., Temple, S., Jackson, L., Shadle, G., and Dixon, R. A. (2006). Multi-site genetic modulation of monolignol biosynthesis suggests new routes for formation of syringyl lignin and wall-bound ferulic acid in alfalfa (*Medicago sativa* L.). Plant J. 48: 113-124.

Chen, H.-C., Li, Q., Shuford, C. M., Liu, J., Muddiman, D. C., Sederoff, R. R., and Chiang, V. L. (2011). Membrane protein complexes catalyze both 4- and 3-hydroxylation of cinnamic acid derivatives in monolignol biosynthesis. Proc. Natl. Acad. Sci. U.S.A 108: 21253-21258.

Coleman, J. O. D., Blake-Kalff, M. M. A., and Davies, T. G. E. (1997). Detoxification of xenobiotics by plants: Chemical modification and vacuolar compartmentation. Trends Plant Sci. 2: 144-151.

Costa, M. A., Collins, R. E., Anterola, A. M., Cochrane, F. C., Davin, L. B., and Lewis, N. G. (2003). An in silico assessment of gene function and organization of the phenylpropanoid pathway metabolic networks in *Arabidopsis thaliana* and limitations thereof. Phytochemistry 64: 1097-1112.

Dauwe, R., Morreel, K., Goeminne, G., Gielen, B., Rohde, A., Van Beeumen, J., Ralph, J., Boudet, A.-M., Kopka, J., Rochange, S. F., Halpin, C., Messens, E., and Boerjan, W. (2007). Molecular phenotyping of lignin-modified tobacco reveals associated changes in cell-wall metabolism, primary metabolism, stress metabolism and photorespiration. Plant J. 52: 263-285.

Davies, A. N. (1998). The new automated mass spectrometry deconvolution and identification system (AMDIS). Spectrosc. Eur. 10: 24-27.

Debeaujon, I., Nesi, N., Perez, P., Devic, M., Grandjean, O., Caboche, M., and Lepiniec, L. (2003). Proanthocyanidin-accumulating cells in *Arabidopsis testa*: regulation of differentiation and role in seed development. Plant Cell 15: 2514-2531.

Dence, C. W. (1992). The determination of lignin. In Methods in lignin chemistry, S. Y. Lin and C. W. Dence, eds (Berlin: Springer-Verlag), pp. 33-61.

Do, C.-T., Pollet, B., Thevenin, J., Sibout, R., Denoue, D., Barriere, Y., Lapierre, C., and Jouanin, L. (2007). Both caffeoyl Coenzyme A 3-O-methyltransferase 1 and caffeic acid O-methyltransferase 1 are involved in redundant functions for lignin, flavonoids and sinapoyl malate biosynthesis in *Arabidopsis*. Planta 226: 1117-1129.

DuBois, M., Gilles, K. A., Hamilton, J. K., Rebers, P. A., and Smith, F. (1956). Colorimetric method for determination of sugars and related substances. Anal. Chem. 28: 350-356.

Ellis, C., Karafyllidis, I., Wasternack, C., and Turner, J. G. (2002). The *Arabidopsis* mutant cev1 links cell wall signaling to jasmonate and ethylene responses. Plant Cell 14: 1557-1566.

Escamilla-Treviio, L. L., Chen, W., Card, M. L., Shih, M.-C., Cheng, C.-L., and Poulton, J. E. (2006). *Arabidopsis thaliana* β-Glucosidases BGLU45 and BGLU46 hydrolyse monolignol glucosides. Phytochemistry 67: 1651-1660.

Fernie, A. R., Trethewey, R. N., Krotzky, A. J., and Willmitzer, L. (2004). Metabolite profiling: from diagnostics to systems biology. Nat. Rev. Mol. Cell Biol. 5: 763-769.

Franke, R., Humphreys, J. M., Hemm, M. R., Denault, J. W., Ruegger, M. O., Cusumano, J. C., and Chapple, C. (2002). The *Arabidopsis* REF8 gene encodes the 3-hydroxylase of phenylpropanoid metabolism. Plant J. 30: 33-45.

Fraser, C. M., Thompson, M. G., Shirley, A. M., Ralph, J., Schoenherr, J. A., Sinlapadech, T., Hall, M. C., and Chapple, C. (2007). Related *Arabidopsis* serine carboxypeptidase-like sinapoylglucose acyltransferases display distinct but overlapping substrate specificities. Plant Physiol. 144: 1986-1999.

Fu, J., Keurentjes, J. J. B., Bouwmeester, H., America, T., Verstappen, F. W. A., Ward, J. L., Beale, M. H., de Vos, R. C. H., Dijkstra, M., Scheltema, R. A., Johannes, F., Koornneef, M., Vreugdenhil, D., Breitling, R., and Jansen, R. C. (2009). System-wide molecular evidence for phenotypic buffering in *Arabidopsis*. Nat. Genet. 41: 166-167.

Goujon, T., Sibout, R., Eudes, A., MacKay, J., and Joulanin, L. (2003a). Genes involved in the biosynthesis of lignin precursors in *Arabidopsis thaliana*. Plant Physiol. Biochem. 41: 677-687.

Goujon, T., Sibout, R., Pollet, B., Maba, B., Nussaume, L., Bechtold, N., Lu, F., Ralph, J., Mila, I., Barrière, Y., Lapierre, C., and Jouanin, L. (2003b). A new *Arabidopsis thaliana* mutant deficient in the expression of O-methyltransferase impacts lignins and sinapoyl esters. Plant Mol. Biol. 51: 973-989.

Grace, S. C., and Logan, B. A. (2000). Energy dissipation and radical scavenging by the plant phenylpropanoid pathway. Philos. Trans. R. Soc. Lond., B, Biol. Sci. 355: 1499-1510.

Graindorge, M., Giustini, C., Jacomin, A. C., Kraut, A., Curien, G., and Matringe, M. (2010). Identification of a plant gene encoding glutamate/aspartate-prephenate aminotransferase: The last homeless enzyme of aromatic amino acids biosynthesis. FEBS Lett. 584: 4357-4360.

Guo, B., Jin, Y., Wussler, C., Blancaflor, E. B., Motes, C. M., and Versaw, W. K. (2008). Functional analysis of the *Arabidopsis* PHT4 family of intracellular phosphate transporters. New Phytol. 177: 889-898.

Guo, D., Chen, F., Inoue, K., Blount, J. W., and Dixon, R. A. (2001). Down-regulation of caffeic acid 3-O-methyltransferase and caffeoyl CoA 3-O-methyltransferase in transgenic alfalfa: impacts on lignin structure and implications for the biosynthesis of G and S lignin. Plant Cell 13: 73-88.

Henkes, S., Sonnewald, U., Badur, R., Flachmann, R., and Stitt, M. (2001). A small decrease of plastid transketolase activity in antisense tobacco transformants has dramatic effects on photosynthesis and phenylpropanoid metabolism. Plant Cell 13: 535-551.

Hertweck, C., Jarvis, A. P., Xiang, L., Moore, B. S., and Oldham, N. J. (2001). A mechanism of benzoic acid biosynthesis in plants and bacteria that mirrors fatty acid β-oxidation. Chem Bio Chem 2: 784-786.

Hirai, M. Y., Sugiyama, K., Sawada, Y., Tohge, T., Obayashi, T., Suzuki, A., Araki, R., Sakurai, N., Suzuki, H., Aoki, K., Goda, H., Nishizawa, O. I., Shibata, D., and Saito, K. (2007). Omics-based identification of *Arabidopsis* Myb transcription factors regulating aliphatic glucosinolate biosynthesis. Proc. Natl. Acad. Sci. U.S.A 104: 6478-6483.

Hu, W.-J., Harding, S. A., Lung, J., Popko, J. L., Ralph, J., Stokke, D. D., Tsai, C.-J., and Chiang, V. L. (1999). Repression of lignin biosynthesis promotes cellulose accumulation and growth in transgenic trees. Nat. Biotechnol. 17: 808-812.

Ideker, T., Galitski, T., and Hood, L. (2001). A new approach to decoding life: systems biology. Annu. Rev. Genomics Hum. Genet. 2: 343-372.

Jarvis, A. P., Schaaf, O., and Oldham, N. J. (2000). 3-Hydroxy-3-phenylpropanoic acid is an intermediate in the biosynthesis of benzoic acid and salicylic acid but benzaldehyde is not. Planta 212: 119-126.

Jones, L., Ennos, A. R., and Turner, S. R. (2001). Cloning and characterization of irregular xylem4 (irx4): a severely lignin-deficient mutant of *Arabidopsis*. Plant J. 26: 205-216.

Jouanin, L., Goujon, T., de Nadaï, V., Martin, M.-T., Mila, I., Vallet, C., Pollet, B., Yoshinaga, A., Chabbert, B., Petit-Conil, M., and Lapierre, C. (2000). Lignification in transgenic poplars with extremely reduced caffeic acid O-methyltransferase activity. Plant Physiol. 123: 1363-1373.

Kaneda, M., Rensing, K. H., Wong, J. C. T., Banno, B., Mansfield, S. D., and Samuels, A. L. (2008). Tracking monolignols during wood development in lodgepole pine. Plant Physiol. 147: 1750-1760.

Kenward, M. G., and Roger, J. H. (1997). Small sample inference for fixed effects from restricted maximum likelihood. Biometrics 53: 983-997.

Kopka, J., Schauer, N., Krueger, S., Birkemeyer, C., Usadel, B., Bergmuiller, E., Dormann, P., Weckwerth, W., Gibon, Y., Stitt, M., Willmitzer, L., Fernie, A. R., and Steinhauser, D. (2005). GMD@CSB.DB: the Golm Metabolome Database. Bioinformatics 21: 1635-1638.

Kruger, N. J., and von Schaewen, A. (2003). The oxidative pentose phosphate pathway: structure and organisation. Curr. Opin. Plant Biol. 6: 236-246.

Kuo, W. P., Liu, F., Trimarchi, J., Punzo, C., Lombardi, M., Sarang, J., Whipple, M. E., Maysuria, M., Serikawa, K., Lee, S. Y., McCrann, D., Kang, J., Shearstone, J. R., Burke, J., Park, D. J., Wang, X., Rector, T. L., Ricciardi-Castagnoli, P., Perrin, S., Choi, S., Bumgarner, R., Kim, J. H., Short, G. F., III, Freeman, M. W., Seed, B., Jensen, R., Church, G. M., Hovig, E., Cepko, C. L., Park, P., Ohno-Machado, L., and Jenssen, T.-K. (2006). A sequence-oriented comparison of gene expression measurements across different hybridization-based technologies. Nat. Biotechnol. 24: 832-840.

Lanot, A., Hodge, D., Jackson, R. G., George, G. L., Elias, L., Lim, E.-K., Vaistij, F. E., and Bowles, D. J. (2006). The glucosyltransferase UGT72E2 is responsible for monolignol 4-O-glucoside production in *Arabidopsis thaliana*. Plant J. 48: 286-295.

Lee, I., Ambaru, B., Thakkar, P., Marcotte, E. M., and Rhee, S. Y. (2010). Rational association of genes with traits using a genome-scale gene network for *Arabidopsis thaliana*. Nat. Biotechnol. 28: 149-156.

Leplé, J.-C., Dauwe, R., Morreel, K., Storme, V., Lapierre, C., Pollet, B., Naumann, A., Kang, K.-Y., Kim, H., Ruel, K., Lefèbvre, A., Joseleau, J.-P., Grima-Pettenati, J., De Rycke, R., Andersson-Gunneris, S., Erban, A., Fehrle, I., Petit-Conil, M., Kopka, J., Polle, A., Messens, E., Sundberg, B., Mansfield, S. D., Ralph, J., Pilate, G., and Boerjan, W. (2007). Down-regulation of cinnamoyl-coenzyme A reductase in poplar: multiple-level phenotyping reveals effects on cell wall polymer metabolism and structure. Plant Cell 19: 3669-3691.

Li, L., Zhou, Y., Cheng, X., Sun, J., Marita, J. M., Ralph, J., and Chiang, V. L. (2003). Combinatorial modification of multiple lignin traits in trees through multigene cotransformation. Proc. Natl. Acad. Sci. U.S.A 100: 4939-4944.

Lim, E.-K., Jackson, R. G., and Bowles, D. J. (2005). Identification and characterisation of *Arabidopsis* glycosyltransferases capable of glucosylating coniferyl aldehyde and sinapyl aldehyde. FEBS Lett. 579: 2802-2806.

Liu, C.-J., Miao, Y.-C., and Zhang, K.-W. (2011). Sequestration and transport of lignin monomeric precursors. Molecules 16: 710-727.

Lommen, A. (2009). MetAlign: interface-driven, versatile metabolomics tool for hyphenated full-scan mass spectrometry data preprocessing. Anal. Chem. 81: 3079-3086.

Maere, S., Heymans, K., and Kuiper, M. (2005). *BiNGO*: a Cytoscape plugin to assess overrepresentation of gene ontology categories in biological networks. Bioinformatics 21: 3448-3449.

Malitsky, S., Blum, E., Less, H., Venger, I., Elbaz, M., Morin, S., Eshed, Y., and Aharoni, A. (2008). The transcript and metabolite networks affected by the two clades of *Arabidopsis* glucosinolate biosynthesis regulators. Plant Physiol. 148: 2021-2049.

Masuko, T., Minami, A., Iwasaki, N., Majima, T., Nishimura, S.-I., and Lee, Y. C. (2005). Carbohydrate analysis by a phenol-sulfuric acid method in microplate format. Anal. Biochem. 339: 69-72.

Meyer, K., Cusumano, J. C., Somerville, C., and Chapple, C. C. S. (1996). Ferulate-5-hydroxylase from *Arabidopsis thaliana* defines a new family of cytochrome P450-dependent monooxygenases. Proc. Natl. Acad. Sci. U.S.A 93: 6869-6874.

Meyermans, H., Morreel, K., Lapierre, C., Pollet, B., De Bruyn, A., Busson, R., Herdewijn, P., Devreese, B., Van Beeumen, J., Marita, J. M., Ralph, J., Chen, C., Burggraeve, B., Van Montagu, M., Messens, E., and Boerjan, W. (2000). Modifications in lignin and accumulation of phenolic glucosides in poplar xylem upon down-regulation of caffeoyl-coenzyme A O-methyltransferase, an enzyme involved in lignin biosynthesis. J. Biol. Chem. 275: 36899-36909.

Mir Derikvand, M., Berrio Sierra, J., Ruel, K., Pollet, B., Do, C.-T., Thevenin, J., Buffard, D., Jouanin, L., and Lapierre, C. (2008). Redirection of the phenylpropanoid pathway to feruloyl malate in *Arabidopsis* mutants deficient for cinnamoyl-CoA reductase 1. Planta 227: 943-956.

Mochida, K., and Shinozaki, K. (2011). Advances in omics and bioinformatics tools for systems analyses of plant functions. Plant Cell Physiol. 52: 2017-2038.

Moerkerke, B., and Goetghebeur, E. (2006). Selecting "significant" differentially expressed genes from the combined perspective of the null and the alternative. J. Comput. Biol. 13: 1513-1531.

Morreel, K., Ralph, J., Kim, H., Lu, F., Goeminne, G., Ralph, S., Messens, E., and Boerjan, W. (2004). Profiling of oligolignols reveals monolignol coupling conditions in lignifying poplar xylem. Plant Physiol. 136: 3537-3549.

Morreel, K., Kim, H., Lu, F., Dima, O., Akiyama, T., Vanholme, R., Niculaes, C., Goeminne, G., Inzé, D., Messens, E., Ralph, J., and Boerjan, W. (2010a). Mass spectrometry-based fragmentation as an identification tool in lignomics. Anal. Chem. 82: 8095-8105.

Morreel, K., Dima, O., Kim, H., Lu, F., Niculaes, C., Vanholme, R., Dauwe, R., Goeminne, G., Inzé, D., Messens, E., Ralph, J., and Boerjan, W. (2010b). Mass spectrometry-based sequencing of lignin oligomers. Plant Physiol. 153: 1464-1478.

Mutwil, M., Øbro, J., Willats, W. G. T., and Persson, S. (2008). GeneCAT—novel webtools that combine BLAST and co-expression analyses. Nucleic Acids Res. 36: W320-W326.

Mutwil, M., Usadel, B., Schütte, M., Loraine, A., Ebenhöh, O., and Persson, S. (2010). Assembly of an interactive correlation network for the *Arabidopsis* genome using a novel heuristic clustering algorithm. Plant Physiol. 152: 29-43.

Nair, R. B., Bastress, K. L., Ruegger, M. O., Denault, J. W., and Chapple, C. (2004). The *Arabidopsis thaliana* REDUCED EPIDERMAL FLUORESCENCE1 gene encodes an aldehyde dehydrogenase involved in ferulic acid and sinapic acid biosynthesis. Plant Cell 16: 544-554.

Nieminen, K. M., Kauppinen, L., and Helariutta, Y. (2004). A weed for wood? *Arabidopsis* as a genetic model for xylem development. Plant Physiol. 135: 653-659.

Oksman-Caldentey, K.-M., and Saito, K. (2005). Integrating genomics and metabolomics for engineering plant metabolic pathways. Curr. Opin. Biotechnol. 16: 174-179.

Patterson, T. A., Lobenhofer, E. K., Fulmer-Smentek, S. B., Collins, P. J., Chu, T.-M., Bao, W., Fang, H., Kawasaki, E. S., Hager, J., Tikhonova, I. R., Walker, S. J., Zhang, L., Hurban, P., de Longueville, F., Fuscoe, J. C., Tong, W., Shi, L., and Wolfinger, R. D. (2006). Performance comparison of one-color and two-color platforms within the MicroArray Quality Control (MAQC) project. Nat. Biotechnol. 24: 1140-1150.

Pilate, G., Guiney, E., Holt, K., Petit-Conil, M., Lapierre, C., Leple, J.-C., Pollet, B., Mila, I., Webster, E. A., Marstorp, H. G., Hopkins, D. W., Jouanin, L., Boerjan, W., Schuch, W., Cornu, D., and Halpin, C. (2002). Field and pulping performances of transgenic trees with altered lignification. Nat. Biotechnol. 20: 607-612.

Raes, J., Rohde, A., Christensen, J. H., Van de Peer, Y., and Boerjan, W. (2003). Genome-wide characterization of the lignification toolbox in *Arabidopsis*. Plant Physiol. 133: 1051-1071.

Ralph, J., Lundquist, K., Brunow, G., Lu, F., Kim, H., Schatz, P. F., Marita, J. M., Hatfield, R. D., Ralph, S. A., Christensen, J. H., and Boerjan, W. (2004). Lignins: Natural polymers from oxidative coupling of 4-hydroxyphenylpropanoids. Phytochem. Rev. 3: 29-60.

Raybould, A. F., and Moyes, C. L. (2001). The ecological genetics of aliphatic glucosinolates. Heredity 87: 383-391.

Roessner, U., Wagner, C., Kopka, J., Trethewey, R. N., and Willmitzer, L. (2000). Simultaneous analysis of metabolites in potato tuber by gas chromatography-mass spectrometry. Plant J. 23: 131-142.

Rohde, A., Morreel, K., Ralph, J., Goeminne, G., Hostyn, V., De Rycke, R., Kushnir, S., Van Doorsselaere, J., Joseleau, J.-P., Vuylsteke, M., Van Driessche, G., Van Beeumen, J., Messens, E., and Boerjan, W. (2004). Molecular phenotyping of the pal1 and pal2 mutants of *Arabidopsis thaliana* reveals far-reaching consequences on phenylpropanoid, amino acid, and carbohydrate metabolism. Plant Cell 16: 2749-2771.

Rosso, M. G., Li, Y., Strizhov, N., Reiss, B., Dekker, K., and Weisshaar, B. (2003). An *Arabidopsis thaliana* T-DNA mutagenized population (GABI-Kat) for flanking sequence tag-based reverse genetics. Plant Mol. Biol. 53: 247-259.

Ruegger, M., and Chapple, C. (2001). Mutations that reduce sinapoylmalate accumulation in *Arabidopsis thaliana* define loci with diverse roles in phenylpropanoid metabolism. Genetics 159: 1741-1749.

Ruegger, M., Meyer, K., Cusumano, J. C., and Chapple, C. (1999). Regulation of ferulate-5-hydroxylase expression in *Arabidopsis* in the context of sinapate ester biosynthesis. Plant Physiol. 119: 101-110.

Ruel, K., Berrio-Sierra, J., Mir Derikvand, M., Pollet, B., Thevenin, J., Lapierre, C., Jouanin, L., and Joseleau, J.-P. (2009). Impact of CCR1 silencing on the assembly of lignified secondary walls in *Arabidopsis thaliana*. New Phytol. 184: 99-113.

Saito, K., Hirai, M. Y., and Yonekura-Sakakibara, K. (2008). Decoding genes with coexpression networks and metabolomics—"majority report by precogs." Trends Plant Sci. 13: 36-43.

Samuels, A. L., Rensing, K. H., Douglas, C. J., Mansfield, S. D., Dharmawardhana, D. P., and Ellis, B. E. (2002). Cellular machinery of wood production: differentiation of secondary xylem in *Pinus contorta* var. *latifolia*. Planta 216: 72-82.

Scharpf, R. B., Iacobuzio-Donahue, C. A., Sneddon, J. B., and Parmigiani, G. (2007). When should one subtract background fluorescence in 2-color microarrays? Biostatistics 8: 695-707.

Schilmiller, A. L., Stout, J., Weng, J.-K., Humphreys, J., Ruegger, M. O., and Chapple, C. (2009). Mutations in the cinnamate 4-hydroxylase gene impact metabolism, growth and development in *Arabidopsis*. Plant J. 60: 771-782.

Schmid, M., Davison, T. S., Henz, S. R., Pape, U. J., Demar, M., Vingron, M., Scholkopf, B., Weigel, D., and Lohmann, J. U. (2005). A gene expression map of *Arabidopsis thaliana* development. Nat. Genet. 37: 501-506.

Schoch, G., Goepfert, S., Morant, M., Hehn, A., Meyer, D., Ullmann, P., and Werck-Reichhart, D. (2001). CYP98A3 from *Arabidopsis thaliana* is a 3'-hydroxylase of phenolic esters, a missing link in the phenylpropanoid pathway. J. Biol. Chem. 276: 36566-36574.

Sessions, A., Burke, E., Presting, G., Aux, G., McElver, J., Patton, D., Dietrich, B., Ho, P., Bacwaden, J., Ko, C., Clarke, J. D., Cotton, D., Bullis, D., Snell, J., Miguel, T., Hutchison, D., Kimmerly, B., Mitzel, T., Katagiri, F., Glazebrook, J., Law, M., and Goff, S. A. (2002). A high-throughput *Arabidopsis* reverse genetics system. Plant Cell 14: 2985-2994.

Shannon, P., Markiel, A., Ozier, O., Baliga, N. S., Wang, J. T., Ramage, D., Amin, N., Schwikowski, B., and Ideker, T. (2003). Cytoscape: a software environment for integrated models of biomolecular interaction networks. Genome Res. 13: 2498-2504.

Sharma, S. B., and Dixon, R. A. (2005). Metabolic engineering of proanthocyanidins by ectopic expression of transcription factors in *Arabidopsis thaliana*. Plant J. 44: 62-75.

Shi, C., Koch, G., Ouzunova, M., Wenzel, G., Zein, I., and Lübberstedt, T. (2006a). Comparison of maize brown-midrib isogenic lines by cellular UV-microspectrophotometry and comparative transcript profiling. Plant Mol. Biol. 62: 697-714.

Shi, L., Reid, L. H., Jones, W. D., Shippy, R., Warrington, J. A., Baker, S. C., Collins, P. J., de Longueville, F., Kawasaki, E. S., Lee, K. Y., Luo, Y., Sun, Y. A., Willey, J. C., Setterquist, R. A., Fischer, G. M., Tong, W., Dragan, Y. P., Dix, D. J., Frueh, F. W., Goodsaid, F. M., Herman, D., Jensen, R. V., Johnson, C. D., Lobenhofer, E. K., Purl, R. K., Scherf, U., Thierry-Mieg, J., Wang, C., Wilson, M., Wolber, P. K., Zhang, L., Amur, S., Bao, W., Barbacioru, C. C., Lucas, A. B., Bertholet, V., Boysen, C., Bromley, B., Brown, D., Brunner, A., Canales, R., Cao, X. M., Cebula, T. A., Chen, J. J., Cheng, J., Chu, T.-M., Chudin, E., Corson, J., Corton, J. C., Croner, L. J., Davies, C., Davison, T. S., Delenstarr, G., Deng, X., Dorris, D., Eklund, A. C., Fan, X.-h., Fang, H., Fulmer-Smentek, S., Fuscoe, J. C., Gallagher, K., Ge, W., Guo, L., Guo, X., Hager, J., Haje, P. K., Han, J., Han, T., Harbottle, H. C., Harris, S. C., Hatchwell, E., Hauser, C. A., Hester, S., Hong, H., Hurban, P., Jackson, S. A., Ji, H., Knight, C. R., Kuo, W. P., LeClerc, J. E., Levy, S., Li, Q.-Z., Liu, C., Liu, Y., Lombardi, M. J., Ma, Y., Magnuson, S. R., Maqsodi, B., McDaniel, T., Mei, N., Myklebost, O., Ning, B., Novoradovskaya, N., Orr, M. S., Osborn, T. W., Papallo, A., Patterson, T. A., Perkins, R. G., Peters, E. H., Peterson, R., Philips, K. L., Pine, P. S., Pusztai, L., Qian, F., Ren, H., Rosen, M., Rosenzweig, B. A., Samaha, R. R., Schena, M., Schroth, G. P., Shchegrova, S., Smith, D. D., Staedtler, F., Su, Z., Sun, H., Szallasi, Z., Tezak, Z., Thierry-Mieg, D., Thompson, K. L., Tikhonova, I., Turpaz, Y., Vallanat, B., Van, C., Walker, S. J., Wang, S. J., Wang, Y., Wolfinger, R., Wong, A., Wu, J., Xiao, C., Xie, Q., Xu, J., Yang, W., Zhang, L., Zhong, S., Zong, Y., and Slikker, W., Jr. (2006b). The MicroArray Quality Control (MAQC) project shows inter- and intraplatform reproducibility of gene expression measurements. Nat. Biotechnol. 24: 1151-1161.

Sibout, R., Eudes, A., Mouille, G., Pollet, B., Lapierre, C., Jouanin, L., and Séguin, A. (2005). CINNAMYL ALCOHOL DEHYDROGENASE-C and -D are the primary genes involved in lignin biosynthesis in the floral stem of Arabidopsis. Plant Cell 17: 2059-2076.

Sinlapadech, T., Stout, J., Ruegger, M. O., Deak, M., and Chapple, C. (2007). The hyper-fluorescent trichome phenotype of the brt1 mutant of Arabidopsis is the result of a defect in a sinapic acid: UDPG glucosyltransferase. Plant J. 49: 655-668.

Smith, C. A., Want, E. J., O'Maille, G., Abagyan, R., and Siuzdak, G. (2006). XCMS: processing mass spectrometry data for metabolite profiling using nonlinear peak alignment, matching, and identification. Anal. Chem. 78: 779-787.

Stein, S. E. (1999). An integrated method for spectrum extraction and compound identification from gas chromatography/mass spectrometry data. J. Am. Soc. Mass Spectrom. 10: 770-781.

Tissier, A. F., Marillonnet, S., Klimyuk, V., Patel, K., Torres, M. A., Murphy, G., and Jones, J. D. G. (1999). Multiple independent defective Suppressor-mutator transposon insertions in Arabidopsis: a tool for functional genomics. Plant Cell 11: 1841-1852.

Vandepoele, K., Quimbaya, M., Casneuf, T., De Veylder, L., and Van de Peer, Y. (2009). Unraveling transcriptional control in Arabidopsis using cis-regulatory elements and coexpression networks. Plant Physiol. 150: 535-546.

Vanholme, R., Van Acker, R., and Boerjan, W. (2010a). Potential of Arabidopsis systems biology to advance the biofuel field. Trends Biotechnol. 28: 543-547.

Vanholme, R., Morreel, K., Ralph, J., and Boerjan, W. (2008). Lignin engineering. Curr. Opin. Plant Biol. 11: 278-285.

Vanholme, R., Demedts, B., Morreel, K., Ralph, J., and Boerjan, W. (2010b). Lignin biosynthesis and structure. Plant Physiol. 153: 895-905.

Vanholme, R., Ralph, J., Akiyama, T., Lu, F., Pazo, J. R., Kim, H., Christensen, J. H., Van Reusel, B., Storme, V., De Rycke, R., Rohde, A., Morreel, K., and Boerjan, W. (2010c). Engineering traditional monolignols out of lignin by concomitant up-regulation of F5H1 and down-regulation of COMT in Arabidopsis. Plant J. 64: 885-897.

Verbeke, G., and Molenberghs, G. (2009). Linear mixed models for longitudinal data. (New York: Springer Verlag).

Vermerris, W., Saballos, A., Ejeta, G., Mosier, N. S., Ladisch, M. R., and Carpita, N. C. (2007). Molecular breeding to enhance ethanol production from corn and sorghum stover. Crop Sci. 47: S142-S153.

Versaw, W. K., and Harrison, M. J. (2002). A chloroplast phosphate transporter, PHT2; 1, influences allocation of phosphate within the plant and phosphate-starvation responses. Plant Cell 14: 1751-1766.

Wolfinger, R. D., Gibson, G., Wolfinger, E. D., Bennett, L., Hamadeh, H., Bushel, P., Afshari, C., and Paules, R. S. (2001). Assessing gene significance from cDNA microarray expression data via mixed models. J. Comput. Biol. 8: 625-637.

Zhong, R., Kays, S. J., Schroeder, B. P., and Ye, Z.-H. (2002). Mutation of a chitinase-like gene causes ectopic deposition of lignin, aberrant cell shapes, and overproduction of ethylene. Plant Cell 14: 165-179.

Zhong, R., Lee, C., Zhou, J., McCarthy, R. L., and Ye, Z.-H. (2008). A battery of transcription factors involved in the regulation of secondary cell wall biosynthesis in Arabidopsis. Plant Cell 20: 2763-2782.

Zhou, J., Lee, C., Zhong, R., and Ye, Z.-H. (2009). MYB58 and MYB63 are transcriptional activators of the lignin biosynthetic pathway during secondary cell wall formation in Arabidopsis. Plant Cell 21: 248-266.

Zhu, D., Hero, A. O., Qin, Z. S., and Swaroop, A. (2005). High throughput screening of co-expressed gene pairs with controlled false discovery rate (FDR) and minimum acceptable strength (MAS). J. Comput. Biol. 12: 1029-1045.

The invention claimed is:

1. A method of producing a plant with a reduced lignin amount or altered lignin composition, wherein the plant has no yield penalty and wherein altered lignin composition is an increased ratio of syringyl to guaiacyl units in lignin polymers, the method comprising:
   a) providing a plant cell with a chimeric gene to create a transgenic plant cell, wherein the chimeric gene comprises:
      i. a plant-expressible promoter,
      ii. a DNA region that, when transcribed, yields a transaldolase inhibitory RNA molecule, and
      iii. a 3' end region involved in transcription termination and polyadenylation;
   b) regenerating a population of transgenic plant lines from said transgenic plant cell;
   c) quantifying the lignin amount or lignin composition of the transgenic plant lines; and
   d) isolating a plant from the population of transgenic plant lines with a reduced lignin amount or altered lignin composition; the plant having no yield penalty in comparison to a plant without the chimeric gene.

2. The method of claim 1, wherein the inhibitory transaldolase RNA molecule of the chimeric gene comprises at least 19 out of 20 consecutive nucleotides of the nucleotide sequence of a transaldolase gene present in said plant cells.

3. The method of claim 1, wherein the inhibitory transaldolase RNA molecule of the chimeric gene comprises at least 19 out of 20 consecutive nucleotides of the complement of the nucleotide sequence of a transaldolase gene present in said plant cells.

4. The method of claim 1, wherein the inhibitory transaldolase RNA molecule of the chimeric gene comprises a sense region comprising a polynucleotide of at least 19 out of 20 consecutive nucleotides of the nucleotide sequence of the transaldolase gene present in said plant cells and an antisense region comprising a polynucleotide of at least 19 out of 20 consecutive nucleotides of the complement of the nucleotide sequence of the transaldolase gene present in said plant cells, wherein said sense and antisense region are able to form a double stranded RNA region comprising said at least 19 out of 20 consecutive nucleotides.

5. A method of producing a plant with a reduced lignin amount or altered lignin composition, wherein the plant has no yield penalty and wherein altered lignin composition is an increased ratio of syringyl to guaiacyl units in lignin polymers, the method comprising:
   a) subjecting a plant cell line or a plant to mutagenesis;
   b) isolating a mutagenized plant cell or plant that has a mutation in an endogenous transaldolase gene resulting in a reduction of transaldolase activity in the plant cell or plant;
   c) quantifying the lignin amount or lignin composition of the mutagenized plant cell or plant; and
   d) isolating a mutagenized plant cell or plant with a reduced lignin amount or altered lignin composition; the plant having no yield penalty.

6. The method according to claim 1, wherein the DNA region comprises a polynucleotide selected from the group consisting of:
- a polynucleotide of at least 19 out of 20 consecutive nucleotides from a polynucleotide encoding a protein comprising SEQ ID NO: 2, 4, 6, 8, 10, 12, 14, 16, 18, 20, 22, or 24;
- a polynucleotide of at least 19 out of 20 consecutive nucleotides from the complement of a polynucleotide encoding a protein comprising SEQ ID NO: 2, 4, 6, 8, 10, 12, 14, 16, 18, 20, 22, or 24;
- a polynucleotide of at least 19 out of 20 consecutive nucleotides of SEQ ID NO: 1, 3, 5, 7, 9, 11, 13, 15, 17, 19, 21, or 23; and
- a polynucleotide of at least 19 out of 20 consecutive nucleotides of the complement of SEQ ID NO: 1, 3, 5, 7, 9, 11, 13, 15, 17, 19, 21, or 23.

7. The method according to claim 2, wherein the transaldolase gene present in the plant cells comprises SEQ ID NO: 1, 3, 5, 7, 9, 11, 13, 15, 17, 19, 21, or 23.

8. The method according to claim 2, wherein the transaldolase gene present in the plant cells comprises SEQ ID NO: 2, 4, 6, 8, 10, 12, 14, 16, 18, 20, 22, or 24.

9. The method according to claim 3, wherein the transaldolase gene present in the plant cells comprises SEQ ID NO: 1, 3, 5, 7, 9, 11, 13, 15, 17, 19, 21 or 23.

10. The method according to claim 3, wherein the transaldolase gene present in the plant cells comprises SEQ ID NO: 2, 4, 6, 8, 10, 12, 14, 16, 18, 20, 22 or 24.

11. The method according to claim 1, wherein the plant-expressible promoter is selected from the group consisting of a constitutive promoter, a lignin specific promoter, a fiber specific promoter, and a vessel specific promoter.

12. A plant comprising a chimeric gene, wherein the chimeric gene comprises:
   i. a plant-expressible promoter;
   ii. a DNA region that, when transcribed, yields a transaldolase inhibitory RNA molecule, wherein the DNA region comprises a polynucleotide selected from the group consisting of:
   - a polynucleotide fragment of at least twenty-five (25) contiguous nucleotides of a polynucleotide encoding a protein comprising SEQ II) NO: 4, 6, 8, 10, 12, 14, 16, 18, 20, 22, or 24,
   - a polynucleotide fragment of at least twenty-five (25) contiguous nucleotides of the complement of a polynucleotide encoding a protein comprising SEQ ID NO: 4, 6, 8, 10, 12, 14, 16, 18, 20, 22, or 24,
   - a polynucleotide fragment of at least twenty-five (25 contiguous nucleotides of SEQ ID NO: 3, 5, 7, 9, 11, 13, 15, 17, 19, 21, or 23, and
   - a polynucleotide fragment of at least twenty-five (25) contiguous nucleotides of the complement of SEQ II) NO: 3, 5, 7, 9, 11, 13, 15, 17, 19, 21, or 23; and
   iii. a 3' end region involved in transcription termination and polyadenylation.

13. The plant of claim 12, wherein the plant-expressible promoter of the chimeric gene is selected from the group consisting of a constitutive promoter, a lignin specific promoter, a fiber specific promoter, and a vessel specific promoter.

* * * * *

UNITED STATES PATENT AND TRADEMARK OFFICE
CERTIFICATE OF CORRECTION

PATENT NO. : 10,006,041 B2
APPLICATION NO. : 14/421796
DATED : June 26, 2018
INVENTOR(S) : Wout Boerjan, Ruben Vanholme and Lisa Sundin Page 1 of 1

It is certified that error appears in the above-identified patent and that said Letters Patent is hereby corrected as shown below:

In the Claims
Claim 12, Column 106, Line 23, change "II) NO: 3, 5, 6, 9," to --ID NO: 3, 5, 6, 9,--

Signed and Sealed this
Twenty-fifth Day of September, 2018

Andrei Iancu
*Director of the United States Patent and Trademark Office*